United States Patent [19]

Egelrud et al.

[11] Patent Number: 5,834,290
[45] Date of Patent: Nov. 10, 1998

[54] RECOMBINANT STRATUM CORNEUM CHYMOTRYPTIC ENZYME (SCCE)

[75] Inventors: Torbjörn Egelrud; Lennart Hansson, both of Umeå, Sweden

[73] Assignee: Astra Aktiebolag, Sodertalje, Sweden

[21] Appl. No.: 557,146

[22] PCT Filed: Jun. 20, 1994

[86] PCT No.: PCT/IB94/00166

§ 371 Date: Dec. 14, 1995

§ 102(e) Date: Dec. 14, 1995

[87] PCT Pub. No.: WO95/00651

PCT Pub. Date: Jan. 5, 1995

[30]     Foreign Application Priority Data

Jun. 18, 1993 [DK]  Denmark .................................. 0725/93

[51] Int. Cl.[6] .............................. C12N 9/64; C12N 15/57; C12N 15/70; C12N 15/85
[52] U.S. Cl. ..................... 435/226; 435/69.1; 435/252.3; 435/252.33; 435/320.1; 536/23.2; 536/23.5; 935/14; 935/29; 935/32; 935/70; 935/73
[58] Field of Search .............................. 424/78.02, 94.64; 435/23, 69.1, 172.1, 213, 320.1, 67.1, 252.3, 252.33, 226; 536/23.2, 23.5

[56]          References Cited

U.S. PATENT DOCUMENTS 4,652,639  3/1987  Stabinsky ................................. 536/27

FOREIGN PATENT DOCUMENTS 9319732  10/1993  WIPO .

OTHER PUBLICATIONS

Egelrud et al. "A chymotrypsin–like proteinase that may be involved in desquamation in plantar stratum corneum," Archiv. Dermatol. Res. 283:108–112, 1991.

Lundstrom et al. "Stratum corneum chymotryptic enzyme . . . ", Act Derm. Venereol. (Stockh) 71:471–474, 1991.

Egelrud et al. "The dependence of detergent–induced cell dissociation in non–palmo–plantar stratum corneum on endogenous proteolysis," Soc. Invest. Dermatol. 95:456–459, 1990.

Lundstrom et al. "Cell shedding from human plantar skin in vitro: Evidence of its dependence on endogenous proteolysis" Soc. Invest. Dermatol. 91:340–343, 1988.

Lundstrom et al. "Cell shedding from human plantar skin in vitro . . . ", Dermatol. Res. 282:234–237, 1990.

Lundstrom et al. "Evidence that cell shedding from plantar stratum corneum in vitro involves endogenous proteolysis," Soc. Invest. Dermatol. 94:216–220, 1990.

(List continued on next page.)

*Primary Examiner*—Keith D. Hendricks
*Assistant Examiner*—William W. Moore
*Attorney, Agent, or Firm*—White & Case L.L.P.

[57]           ABSTRACT

The present invention relates to a polypeptide having the amino acid sequence SEQ ID NO:2 or an analogue or variant thereof having SCCE activity as defined in the present application, such as a polypeptide having a subsequence of the amino acid sequence SEQ ID NO:2. Furthermore, the present invention relates to nucleotide sequences encoding polypeptides having SCCE activity as well as to expression systems, expression vectors, plasmids and non-human organisms comprising said nucleotide sequences. Important aspects of the present invention relate to pharmaceutical, cosmetic and skin care compositions comprising a polypeptide having SCCE activity, and the use of a polypeptide having SCCE activity for the treatment or prophylaxis of various diseases such as acne, xeroderma or other hyperkeratotic conditions such as callosities and keratosis pilaris as well as the various ichthyoses, psoriasis and other inflammatory skin diseases such as eczemas. Moreover, the present invention relates to the use of a compound which has an inhibitory effect on the enzymatic activity of native SCCE for the manufacture of a pharmaceutical composition for treatment or prophylaxis of autoimmune pemphigus diseases or acantholytic diseases such as familiar pemphigus and Darier's disease.

12 Claims, 22 Drawing Sheets

OTHER PUBLICATIONS

Lin et al (1989), –geneseq 25 database, Seq 10 p. 95121 (from EP 297913 A).

Hannson et al (1994) J Biol Chem 269:19420–426. "Cloning, Expression and Characterization of Stratum Corneum Chymotyptic Enzyme: A Skin–Specific Human Serine Proteinase".

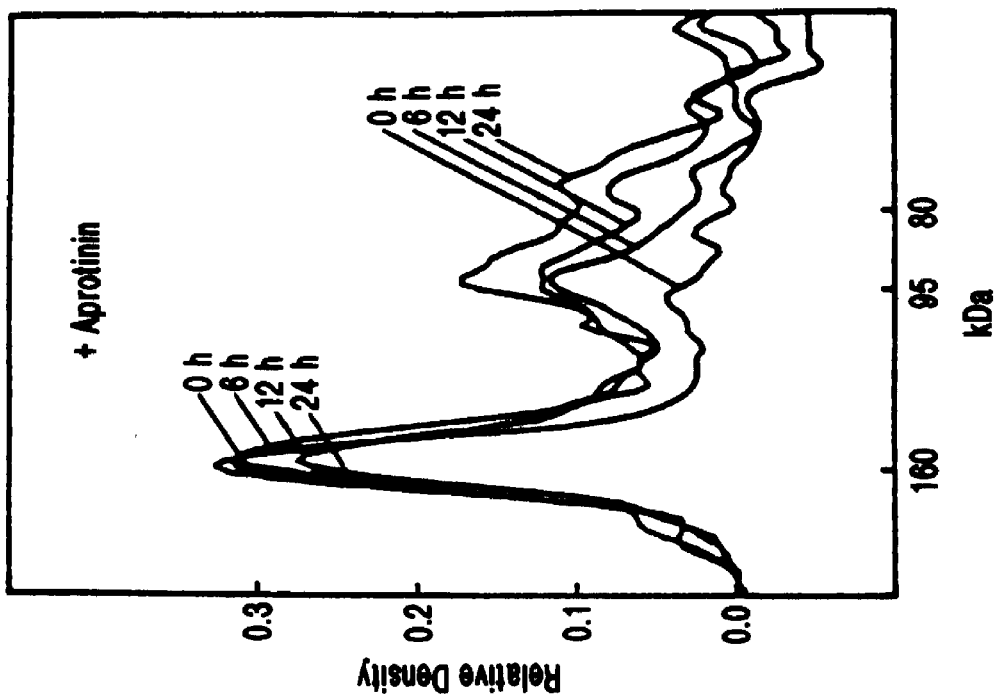
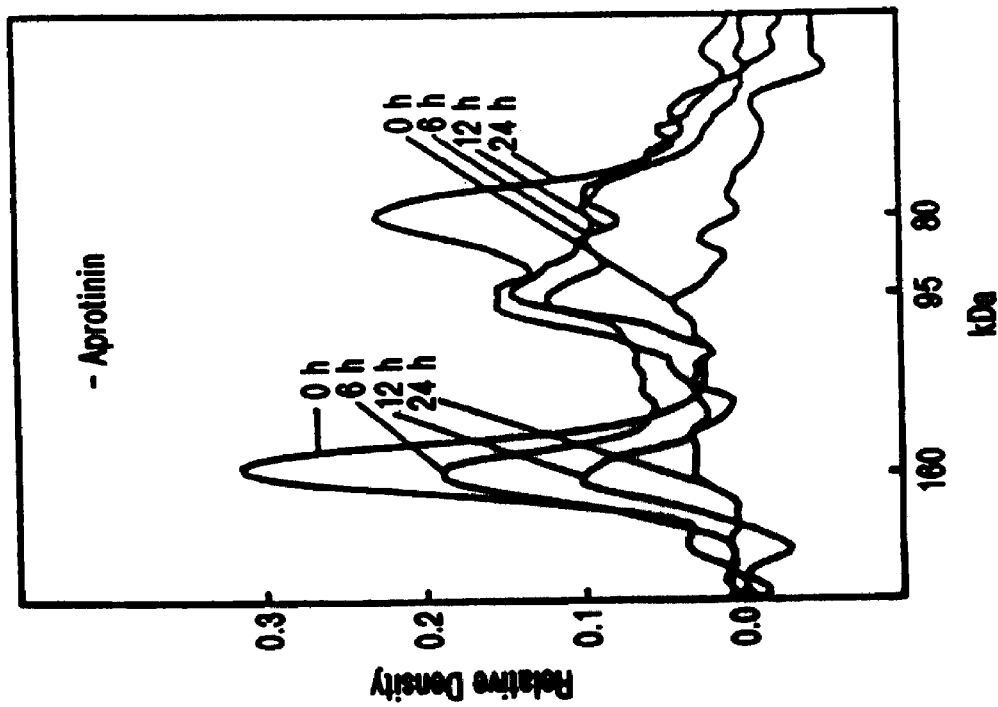
Fig. 4A
Fig. 4B

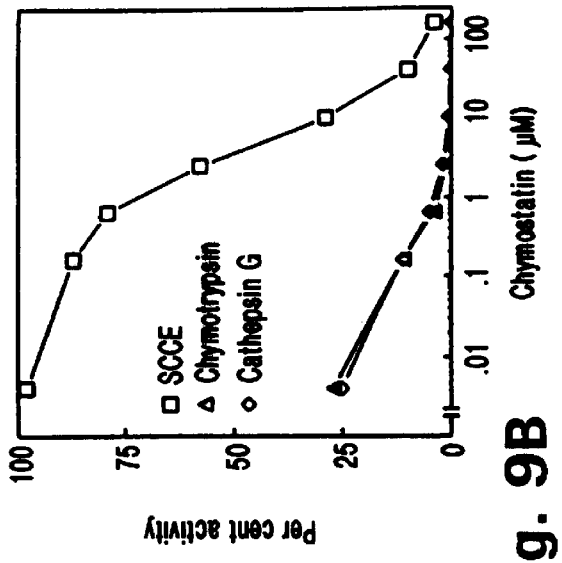
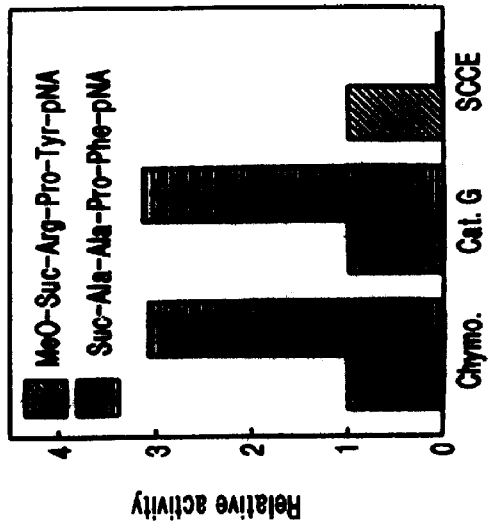
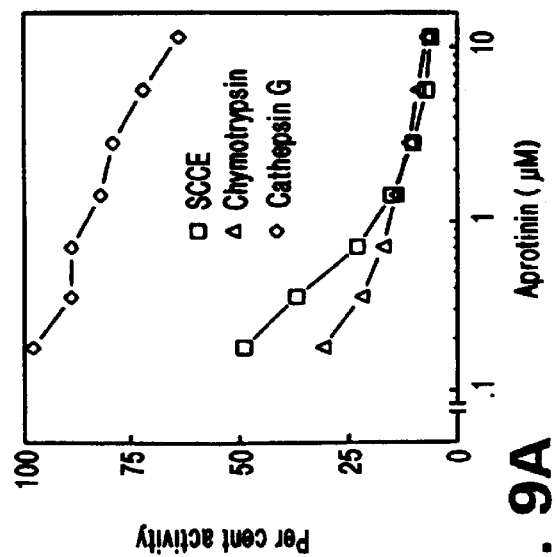
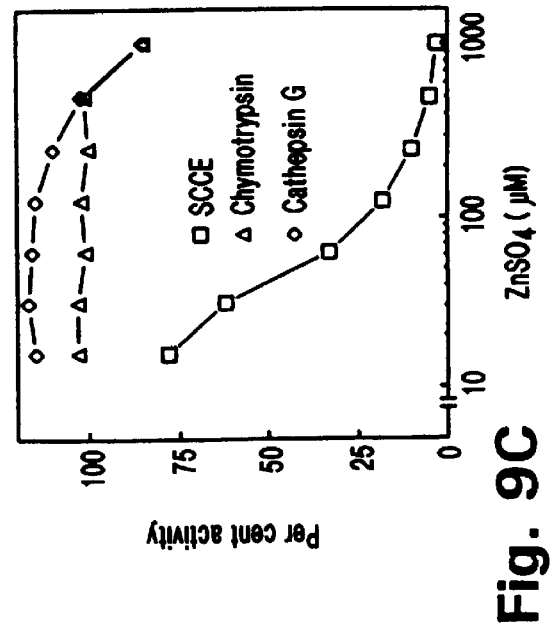
Fig. 9A
Fig. 9B
Fig. 9C
Fig. 9D

RECOMBINANT STRATUM CORNEUM CHYMOTRYPTIC ENZYME (SCCE)

The present invention relates to a recombinant polypeptide and to a nucleotide sequence encoding the polypeptide, to an expression system capable of expressing the polypeptide as well as to pharmaceutical and cosmetic compositions comprising the polypeptide and to the use of the polypeptide for various cosmetic or therapeutic purposes.

BRIEF DESCRIPTION OF THE INVENTION

The skin as an organ is of interest from biological, medical, and cosmetological points of view. There are a large number of skin diseases that are either organ-specific, e.g. psoriasis and eczemas, or are manifestations of general disease, such as general allergic reactions. The fact that there are skin-specific diseases can be considered as a proof of the existence of molecular mechanisms that are unique for the skin. Analogously, studies on skin-specific molecular processes are of importance for the understanding and treatment of skin disorders. It seems reasonable to assume that several of these processes in one way or another are related to the most specialized function of the skin, that is the formation of a physico-chemical barrier between body exterior and interior. The physico-chemical skin barrier is localized in the outermost layer of the skin, the stratum corneum.

The stratum corneum is the most specialized structure of the skin. It is the end product of the differentiation process of the epidermis, that is the stratified squamous epithelium which accounts for the outermost portion of the skin. The majority of the cells of the epidermis consist of keratinocytes in various states of differentiation. The lowermost keratinocytes, the basal cells, reside on a basal membrane in contact with the dermis, that is the connective tissue of the skin, and are the only keratinocytes that have dividing capability. A fraction of the basal cells continuously leaves the basal membrane and goes through a differentiation process which eventually makes the cells become building blocks of the stratum corneum. In this process the keratinocytes go through a number of adaptive changes. There is an increased content of cytoskeleton consisting of epidermis-specific cytokeratins. The intermediate filaments of contiguous cells are joined to a functional unit by an increased number of desmosomes. The most dramatic changes take place during the transition from the uppermost living cell layer, the stratum granulosum, to the non-viable stratum corneum in a process usually called keratinization. Covalently cross-linked proteins are deposited close to the inner aspect of the plasma membrane, forming a very resistant cell envelope. Furthermore a lipid-rich substance, originating in a keratinocyte-specific cell organel, is secreted to the extracellular space and, by forming lipid lamellae which surround the cells of the stratum corneum, constitutes the permeability barrier to hydrophilic substances. Finally all intracellular structures except the densely packed cytokeratin filaments disappear.

The cells of the stratum corneum, the corneocytes, are thus non-viable. This means that the regulation of various processes in the stratum corneum must be the result of a "programming" at a state where the keratinocytes are still viable. The turnover of the epidermis, which normally proceeds in about four weeks during which the cells are part of the stratum corneum for about two weeks, is ended by means of cell shedding from the skin surface in the process of desquamation. This process is an example of "programming" of the stratum corneum. A prerequisite for the function of the stratum corneum as a physico-chemical barrier is that its individual cells are held together by mechanically resistant structures, that is desmosomes. The degradation of desmosomes, which is a prerequisite for desquamation, must be regulated so as to give a cell shedding from the skin surface which balances de novo production of the stratum corneum without interfering with the barrier functions of the tissue.

Disorders of keratinization

Under a large number of pathological conditions in the skin of varying severity, there are disturbances in the keratinization process. In psoriasis there is, in addition to a typical chronic inflammation, overproduction of an immature stratum corneum resulting in the typical scaling of this disease. There is a group of inherited skin diseases characterized by a thickened stratum corneum which leads to the formation of "fish scales", the so-called ichthyoses. In several of the ichthyoses there is a decreased rate of desquamation. Although less severe than the ichthyoses, "dry skin" (xeroderma) is also characterized by a stratum corneum from which corneocytes are shed, not as under normal conditions as single cells or as small aggregates of cells, but as large, macroscopically visible scales. This disorder is very common among elderly people and among atopics, that is individuals with a decreased resistance to skin irritants and a disposition to develop a characteristic form of endogenous eczema. In the acne diseases there is a disturbed keratinization in the ducts of the sebaceous glands which leads to the formation of comedones and plugging. The formation of comedones precedes and is believed to provoke the inflammatory acne lesion.

Proteolytic enzymes are involved in keratinization

There are several stages in the keratinization process and during the turnover of the stratum corneum where proteolytic enzymes seem to play important roles. Certainly the disappearance of all intracellular structures except for the cytokeratin filaments occurring during the transition between viable and cornified epidermal layers must involve proteolysis. The transformation of profilaggrin to filaggrin, a protein which is believed to function in the special type of aggregation of cytokeratin filaments during keratinization, may be catalyzed by a specific proteinase. In the stratum corneum filaggrin is further degraded to low-molecular weight components which are probably important as "natural moisturizers". Furthermore there are proteolytic modifications of cytokeratin polypeptides during the keratinization process. Finally, proteolytic events are likely to play crucial roles in the degradation of intercellular cohesive structures in the stratum corneum in processes eventually leading to desquamation.

Stratum corneum cell cohesion and desquamation. The role of desmosomes

Intercellular cohesion in the stratum corneum as well as in the viable parts of the epidermis is mediated to a significant extent by desmosomes. A desmosome consists of two symmetrical halves, each of which is formed by two contiguous cells. Each desmosomal half has one intracellular part linked to the cytokeratin filaments and one part made up by glycoproteins anchored intracellularly and with transmembranal and extracellular parts. The extracellular parts of these proteins, the desmogleins, are adhesion molecules, and through their interaction with each other in the extracellular space a cohesive structure is formed. The degradation of desmosomes seems to follow somewhat different routes in the stratum corneum of palms and soles as compared to non-palmo-plantar stratum corneum. In the latter tissue around 85% of the desmosomes disappear soon after the cells have become fully cornified. The remaining desmosomes, which are preferentially located at the villous edges of the extremely flattened cells, apparently remain intact up to the level where desquamation takes place. In palmo-plantar stratum corneum the corneocytes are much less flattened, and there is no extensive degradation of desmosomes in deeper layers of the tissue. In both tissues desquamation is associated with desmosomal degradation. In ichthyotic skin as well as in "dry skin", the number of desmosomes in the superficial layers of the stratum corneum has been shown to be increased.

Stratum corneum intercellular lipids

The difference in desmosomal degradation between palmo-plantar and non-palmo-plantar stratum corneum may be related to the difference in amounts of extracellular lipids in the two types of tissue. The lipid content is considerably higher in non-palmo-plantar stratum corneum. As a corollary the efficiency of this tissue as a permeability barrier to water and other hydrophilic substances is superior to the stratum corneum of palms and soles. Since desmosomes occupy significant volume and since intact desmosomes prevent a widening of the extracellular space, desmosomal degradation may be a mechanism by which more extracellular space is made available for lipids. The extracellular lipids of the stratum corneum are related to desquamation also in several other ways. Since they are major constituents of the extracellular space they may be expected to have important influences on the activities of enzymes with function at this localization, e.g. enzymes responsible for desmosomal degradation. Indeed, various disturbances in lipid metabolism have been shown to be the likely causes of several types of ichthyoses. It is also likely that lipids themselves contribute to some extent to stratum corneum cell cohesion. Moreover, the secretion of lipids to the stratum corneum extracellular space is likely to be associated with the secretion also of a number of enzymes. Precursors of the lipids are stored in the upper viable keratinocytes in specific organelles. These so-called lamellar bodies have been shown to contain a number of hydrolytic enzymes. It is thus contemplated that an enzyme responsible for desmosomal degradation in the stratum corneum is synthesized, possibly in an inactive pro-form, by the keratinocytes, stored in lamellar bodies, and secreted to the stratum corneum extracellular space during keratinization where it may be activated and its activity further regulated by, among other factors, the composition of the extracellular lipids.

Disorders of cell cohesion in viable epidermis

There are a number of skin diseases where there is impaired cohesion between keratinocytes in the non-cornified, viable epidermal layers. These diseases are characterized by a phenomenon called acantholysis, that is a breakdown of desmosomal contacts between otherwise apparently normal keratinocytes. The process is likely to be mediated by proteinases, which have so far not been fully identified. Acantholysis, which when extensive leads to blister formation, is a characteristic of the autoimmune diseases pemphigus vulgaris and pemphigus foliaceus, the inherited benign familiar pemphigus (Hayley-Hayley's disease), and the inherited dyskeratosis follicularis (Darier's disease).

Epidermis takes an active part in immunological and inflammatory reactions

In addition to its function as the producer of the physicochemical barrier between body interior and exterior, the epidermis also functions as an active immunological barrier. The keratinocytes have the ability to produce as well as respond to a large number of cytokines and other inflammatory mediators through which they communicate and interact with cells of the immunological and inflammatory systems. This is of major importance in the host defence against microbial infections and in wound healing. Modern research has also shown that the keratinocytes are likely to take an active part in many inflammatory skin diseases such as psoriasis and eczemas.

Epidermal proteinases may be important in inflammation

One of the cytokines produced by keratinocytes is interleukin 1 (Il-1). Il-1 exists in two forms, Il-1α and Il-1β, both of which are present in the epidermis. Whereas Il-1α is fully active as synthesized, Il-1β is synthesized as an inactive 31 kD pro-form. Pro-Il-1β is converted to the active 17 kD form by a specific proteinase present e.g. in monocytes but so far not detected in normal epidermis. A number of serine proteinases with chymotrypsin-like substrate specificity (pancreatic chymotrypsin and cathepsin G of neutrophilic granulocytes) can, however, also serve as pro-Il-1β activators.

As suggested by Norris (1990), proteolytical enzymes present in the stratum corneum intracellular space may under certain conditions be able to convert inactive forms of cytokines to active forms. Of particular interest in this context is the biologically inactive pro-interleukin-1β, which has been shown to be produced by keratinocytes (Mizutani et al., 1991). So far no epidermal enzymes with the ability to convert pro-interleukin-1β to active interleukin-1β have been found. Since, however, chymotrypsin and cathepsin G (a chymotrypsin-like enzyme) have the ability to catalyze the conversion of inactive 31 kD recombinant pro-interleukin 1β to a fully active 17 kD form, it is possible that also epidermal chymotrypsin-like enzymes can catalyze this conversion.

Figure 1:
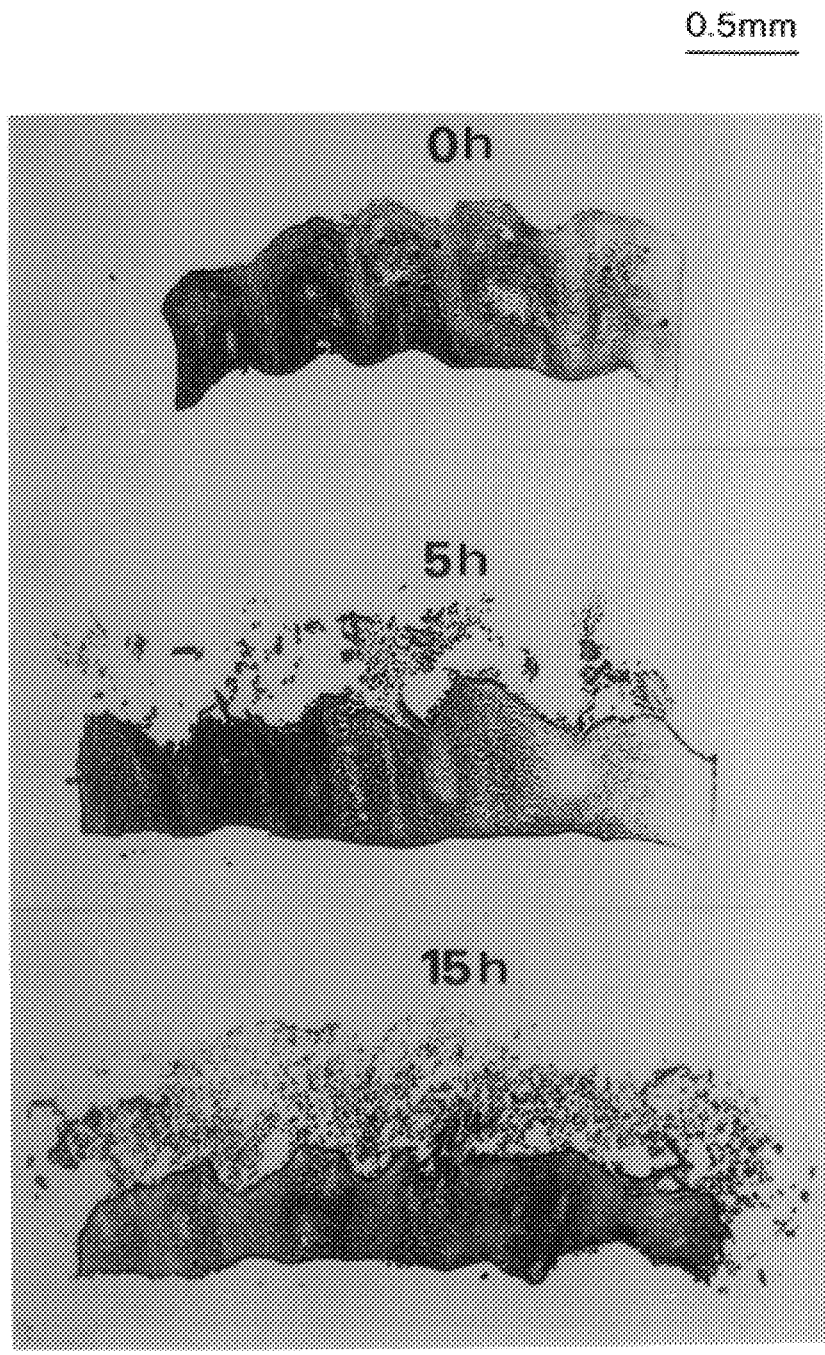
FIG. 1.

Unipolar cell shedding from plantar stratum corneum in vitro. The tissue surface that had faced outwards in vivo is upwards in the figure. Note that there was a progressive cell dissociation at this surface during the incubation, but no cell dissociation at the other surfaces.

FIG. 2.

Time course and the effect of aprotinin on cell release from plantar stratum corneum incubated without (circles) and with (triangles) aprotinin. Mean (cumulative values for four tissue pieces) and range are given.

FIG. 3.

Anti-desmoglein (anti-DG I) reactive components in coherent plantar stratum corneum and in dissociated cells. A. Coomassie blue-stained SDS-PAGE. B. Immunoblot. 1–3: Coherent tissue, undiluted (1), diluted ⅓ (2), diluted ⅑ (3). 4–5: Dissociated cells, undiluted (4), diluted ⅓ (5). Note only apparently intact DG I with Mr 160 kD in coherent tissue, and only degradation products of DG I with Mr 95 and 80 kD in dissociated cells.

FIG. 4.

Time course and the effect of aprotinin on the degradation of desmoglein I (DG I) in plantar stratum corneum undergoing cell shedding in vitro. Densitometric scannings of immunoblots of extracts of plantar stratum corneum incubated in the absence (A) and presence (B) of aprotinin (15 μM). The peak at 160 kD corresponds to intact DG I. The peaks at 95 and 80 kD corresponds to degradation products of this protein (cf. FIG. 3). Note efficient inhibition by aprotinin on the degradation dation of DG I.

FIG. 5.

The effect of zinc ion (A), chymostatin and leupeptin (B) on the degradation of desmoglein I (DG I) in plantar stratum corneum during cell shedding in vitro. Note inhibition of the transformation of the anti-DG I positive components from 160 kD to 95 and 80 kD by zinc ions and chymostatin, but not by leupeptin.

FIG. 6.

Peptide hydrolyzing activity associated with plantar stratum corneum cells. Hydrolysis of the two substrates were followed by means of measuring the change in absorbance at 405 nm. Means of incubations in triplicate. Squares=S-2586; Circles =S-2288.

FIG. 7.

pH-dependence of the corneocyte-associated S-2586 hydrolysing activity. Means of incubations in triplicate. Squares=sodium acetate, circles =sodium phosphate, triangles=Tris-HCl.

FIG. 8.

Zymography, showing caseinolytic activity in extracts of dissociated plantar stratum corneum cell. See also text under Example 2.2 for experimental details.

A: Comparison of the enzyme from plantar corneocytes extracted with Laemmli's sample buffer without reducing agent (sc/s) and KCl (sc/k) with bovine chymotrypsin, 0.125 ng (c) and bovine trypsin, 0.5 ng (t). Before electrophoresis the KCl extract was dialysed against 5 mM Tris-HCl, pH 6.8, and SDS and glycerol added to give final concentrations as in the sample buffer; 10 µl added to all lanes. Molecular weight markers to the left.

B: The dependence on pH in the incubation buffer. Enzyme source =SDS-extracts of dissociated plantar corneocytes. Buffers for pretreatment with Triton X-100 and incubation: 0.1 M sodium acetate (pH 4.0 and pH 5.5), and 0.1 M Tris-HCl (pH 7.0 and pH 8.0). Other conditions as in A.

C: The effect of inhibitors. sc=SDS-extract of plantar corneocytes; c=bovine chymotrypsin; t=bovine trypsin. The inhibitors were present during pretreatment with Triton X-100 and the subsequent incubation. The final concentration of leupeptin was 160 µM, of aprotinin 15 µM, of chymostatin 40 µM, and of zinc ions (as sulphate) 100 µM. Leupeptin and chymostatin were added as solutions in dimethylsulphoxide (DMSO). Buffer for pretreatment and incubation=0.1 M Tris-HCl pH 8 with final concentration of DMSO 1% (v/v). Other conditions as in A.

FIG. 9.

Comparison of SCCE, bovine chymotrypsin, and human cathepsin G as regards effects of inhibitors (A; aprotinin, B; chymostatin, C; zinc sulphate) and substrate specificity (D). In A–C the enzyme activity with no inhibitor present was standardized to 100%. In D the enzyme activity with MeO-Suc-Arg-Pro-Tyr-pNA was standardized to 1 arbitrary unit.

FIG. 10.

Affinity chromatography on covalently linked soybean trypsin inhibitor (SBTI). Dotted line: Absorbance at 280 nm, reflecting protein concentration of the eluate. Solid line with unfilled squares: Peptide hydrolysing activity with S-2586 as substrate, given as change in absorbance at 405 nm. Solid line with unfilled circles: Peptide hydrolysing activity with S-2288 as substrate, given as change in absorbance at 405 nm multiplied ten-fold.

FIG. 11.

Figure 10:
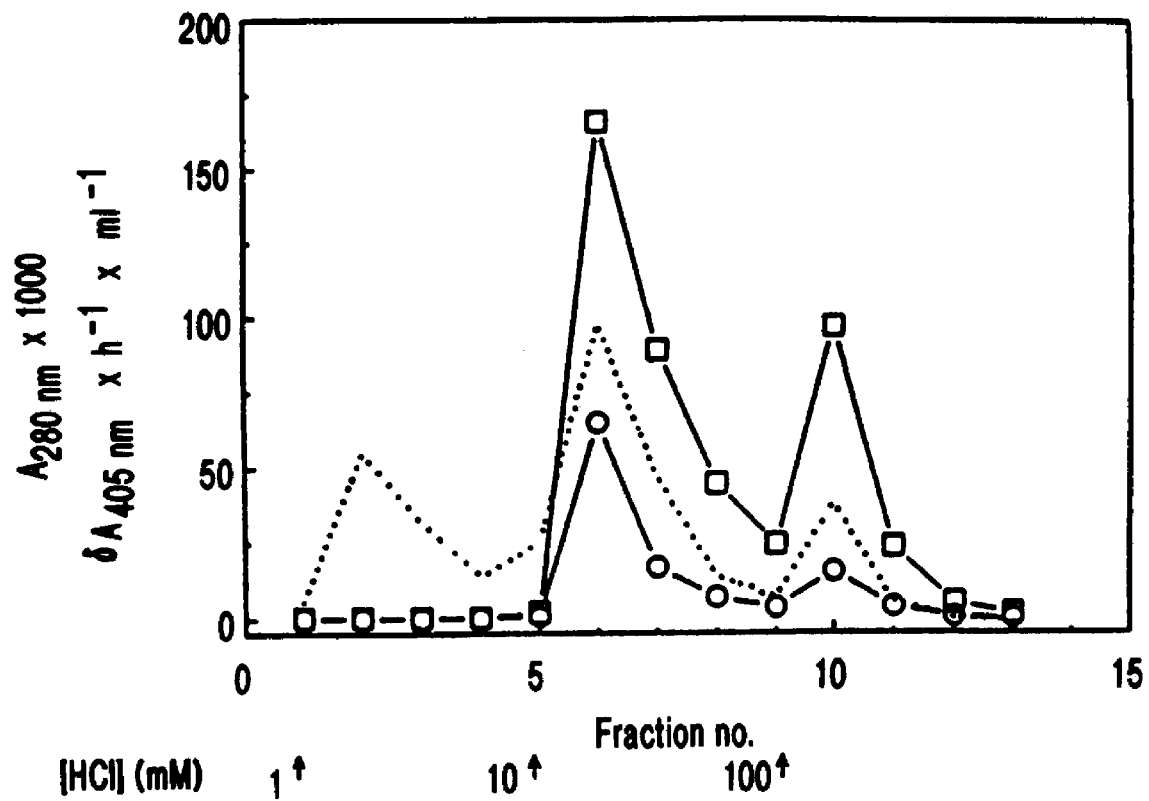

SDS-PAGE and Coomassie blue-staining (A) and zymography after SDS-PAGE with co-polymerized casein (B) of fractions 2, 6, and 10 from the chromatogram shown in FIG. 10. Molecular weight markers to the left. In B: l: Group of caseinolytic components that could be inhibited by leupeptin (160 µM). c: Group of caseinolytic components that could be inhibited by chymostatin (40 µM).

FIG. 12.

SDS-PAGE of SCCE purified by affinity chromatography on SBTI-Affigel 15. 12.5% gel. 1: Unreduced sample. 2: Reduced sample. Molecular weight markers to the left.

FIG. 13.

N-terminal amino acid sequence of SCCE. Asterisks denote uncertainties for the assumed cystines in positions 7 and 9. Question marks denote positions where no amino acid derivatives could be detected but with no drops in yields in subsequent steps.

FIG. 14.

Characterization of monoclonal antibodies TE4b and TE9b by means of immunoprecipitation and immunoblotting.

a: Coomassie-stained 12.5% SDS-PAGE, non-reducing conditions.

Lane 1: Molecular weight markers.
Lane 2: KCl-extract prepared as described in Example 3.1 of dissociated plantar corneocytes.
Lane 3: SCCE purified as described in Example 4.1 by affinity chromatography on insolubilized soybean trypsin inhibitor.

b: Zymography of immunoprecipitates in 12.5% SDS-PAGE with 0.1% co-polymerized heat denatured casein, Coomassie-stained gel.

Lane 1: Molecular weight markers.
Lane 2: KCl-extract, dialyzed as in a.
Lanes 3–6: Solubilized immunoprecipitates with (from left to right) moab TE4b (20 µg), moab TE9b (10 µg), moab PZ (10 µg), and phosphate buffered saline. Moab PZ is a mouse monoclonal antibody of IgG1-kappa type to pregnancy zone protein and was used as a n unrelated negative control.

c: Immunoblot from 12.5% SDS-PAGE (non-reducing conditions).

Lane 1: biotinylated molecular weight markers detected with alkaline phosphatase-conjugated avidin (BioRad). Electrophoresed sample in lanes 2, 4, and 6 the same as in lane 2 in a, and in lanes 3, 5 and 7 the same as in lane 3 in a.
Lanes 2 and 3: First antibody=moab TE4b, 0.2 µg per ml.
Lanes 4 and 5: First antibody=moab TE9b, 0.1 µg per ml.
Lanes 6 and 7: First antibody =moab PZ, 0.1 µg per ml .
Arrowheads in a–c denote relative molecular weights (from top to bottom) 93, 66, 45, 31, 22, and 14 kD, respectively.

FIG. 15.

Figure 15:
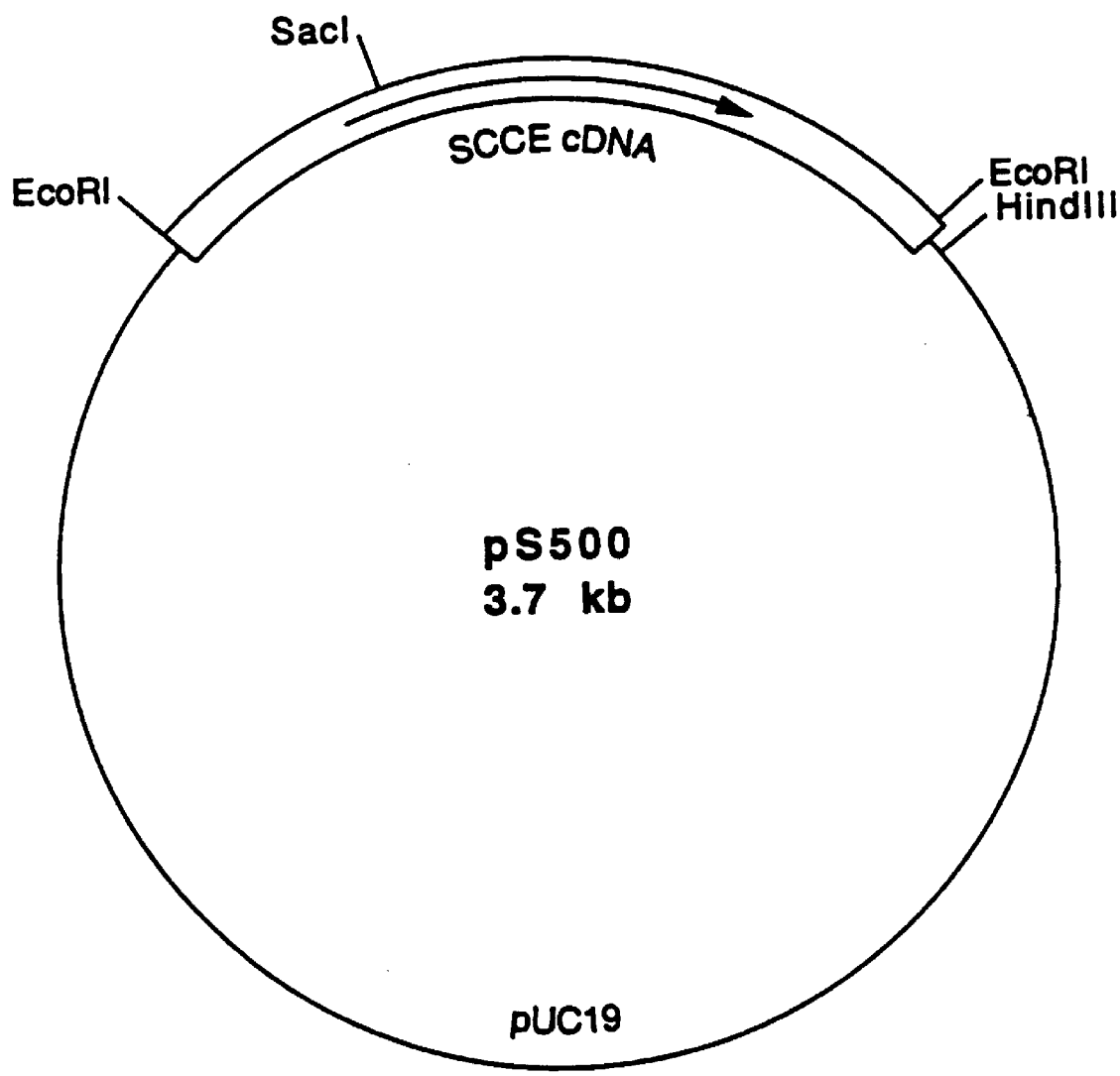

FIG. 15 shows the plasmid pS500. This plasmid contains the full-length human SCCE cDNA cloned into pUC19. For details see Example 6.

FIG. 16.

Northern blots with mRNA prepared from human epidermis. Poly-T-purified RNA corresponding to approximately 100 g of total RNA was applied in each lane. 1: Hybridization carried out with a probe prepared from a 1070 bp Hinc 2/Hinc 2 fragment of SCCE-cDNA. 2: Hybridization carried out with a probe prepared from a 655 bp Hinc 2/Bgl 2 fragment of SCCE-cDNA.

FIG. 17.

a Coomassie-stained SDS-PAGE, 12.5% gel. 1 and 2: PBS-Triton X-100 insoluble pellets of sonicated TG 2 cells transformed with PSS10and pS511 respectively and induced with IPTG. 3: SCCE purified from human plantar stratum corneum.

b Immunoblots with chicken pre-immuneserum (1–3) and chicken anti-SCCE (4–6). 1 and 4: TG 2-cells transformed with pS510 and induced with IPTG. 2 and 5: TG 2-cells transformed with pS511 and induced with IPTG. 3 and 6: SCCE purified from human plantar stratum corneum.

Samples were prepared by boiling in sample buffer with mercaptoethanol.

FIG. 18.

Figure 18:
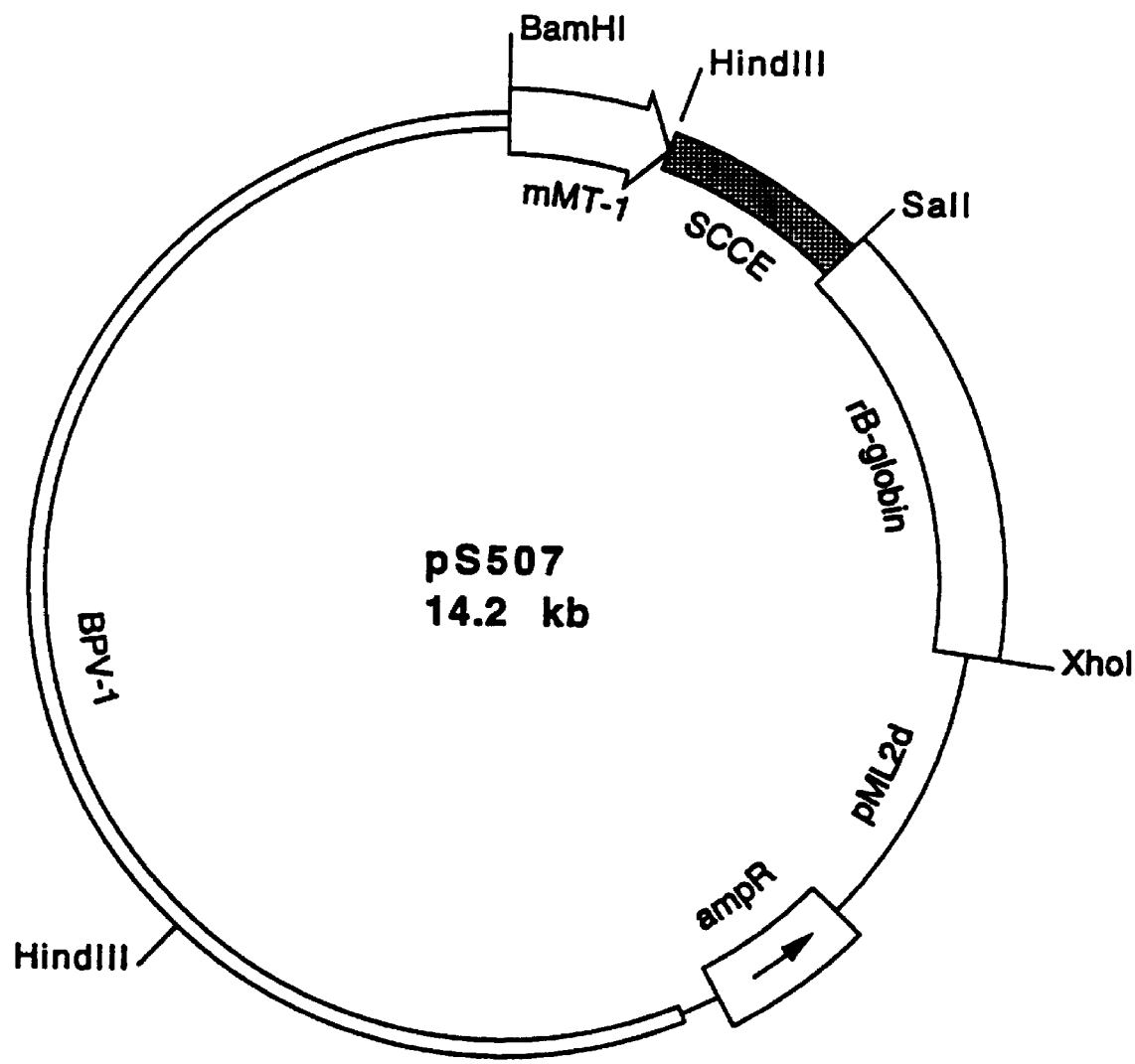

FIG. 18 shows a circular map of the expression vector pS507, constructed as described in Example 9. The vector pS507 mediates expression of recombinant human SCCE in mammalian cells.

FIG. 19.

Figure 19:
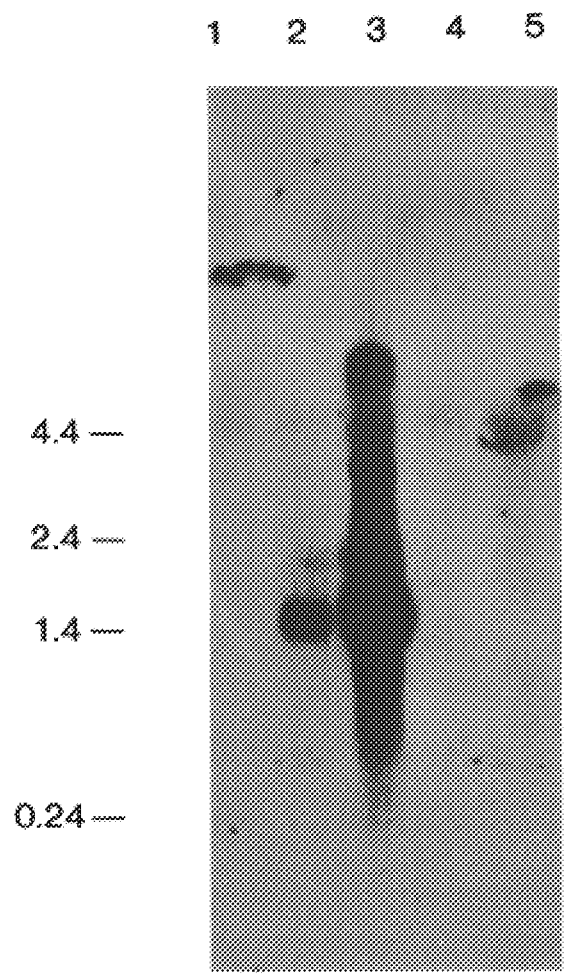

FIG. 19 shows analysis of expression of the recombinant human SCCE gene of pS507 in mammalian cells.

Lane 1: RNA from C127 cells.

Lane 2: RNA from an isolated clone, 1:24, of C127 cells transfected with pS507.

Lane 3: RNA from a population mixture of C127 clones transfected with pS507.

Lanes 4 and 5: RNA from C127 cells transfected with an expression vector, pS147, which is identical to pS507 except that it lacks the SCCE cDNA sequence. Size markers are indicated to the left.

FIG. 20.

SDS-PAGE followed by immunoblotting of SCCE expressed in C127 cells.

Lanes 1 and 6: Prestained molecular weight marker (Bio-Rad, 106, 80, 49.5, 32.5, 27.5 and 18.5 kDa)

Lane 2: pS507/C127, mix, T-flask

Lane 3: pS507/C127, mix, roller A

Lane 4: pS507/C127, mix, roller B

Lane 5: Negative control pS522/C127

Lane 7: Native SCCE prepared from stratum corneum

Lane 8: pS507/C127, clone 24, T-flask

Lane 9: pS507/C127, clone 24, roller A

Lane 10: pS507/C127, clone 24, roller B

FIG. 21.

SDS-PAGE (A) and immunoblotting (B) of recombinant SCCE purified from C127 cell culture medium with cells carrying the plasmid pS507.

Lanes 1 and 5: Prestained molecular weight marker (Bio-Rad, 106, 80, 49.5, 32.5, 27.5 and 18.5 kDa)

Lane 2: Cell medium before purification

Lane 3: Unbound material collected from the chromatography

Lane 4: Bound material eluted with the low pH buffer

FIG. 22.

Native SCCE and activated recombinant SCCE assayed for activity on a casein polyacrylamide gel.

Lanes 1 and 10: Molecular weight markers (Pharmacia 14–94 kDa).

Lane 2: Native SCCE.

Lane 3: Native SCCE.

Lanes 4–6: Recombinant SCCE cleaved for 1 hour, 3 hours and overnight, respectively (460 ng/well).

Lane 7: Trypsin at the same amount as in the samples in lanes 4–6, but in the absence of APMSF.

Lane 8: Trypsin at the same amount as in the samples in lanes 4–6 in the presence of the same amount of APMSF as in the samples.

Lane 9: Same as lane 3.

FIG. 23.

Immunoblot of N-Glycosidase F® treated native and recombinant SCCE. Samples were separated on 8–18% SDS-PAGE and immunoblotted as described above.

Lane 1: Molecular weight marker. Molecular masses, from the top: 106, 80, 49.5, 32.5, 27.5, and 18.5 kDa.

Lanes 2 and 3: Recombinant SCCE, 0.3 and 3 µg, respectively.

Lanes 4 and 5: Native SCCE, 1.5 and 1.8 µg, respectively. Samples in lanes 3 and 5 were treated with N-Glycosidase F®.

DETAILED DESCRIPTION OF THE INVENTION

The present invention relates to an enzyme which has been termed stratum corneum chymotryptic enzyme (SCCE) which is contemplated to be responsible for desmosomal degradation in the stratum corneum. Evidence is presented in Example 1 showing that cell shedding from the surface of the cornified surface layer of the skin involves degradation of desmosomal proteins and that the responsible enzyme seems to be a chymotrypsin-like serine proteinase which can be inhibited by zinc ions.

Example 2 describes the discovery of stratum corneum chymotryptic enzyme (SCCE); a proteinase which fulfils criteria of being responsible for the degradation of intracellular cohesive structures in the stratum corneum in vitro and possibly also in vivo. Example 3 describes the partial characterization of stratum corneum chymotryptic enzyme (SCCE) activity using chromogenic substrates.

The results demonstrate that SCCE differs enzymologically from other chymotryptic proteinases. The inhibitor profile and the ability to degrade two different substrates of chymotrypsin-like enzymes is significantly different for SCCE as compared to bovine chymotrypsin and human cathepsin G. SCCE also seems to differ from human mast cell chymase. The latter enzyme catalyses the degradation of Suc-Ala-Ala-Pro-Phe-pNA (SEQ ID NO:11) efficiently (see Schwartz et al., 1987 and Schechter et al., 1989)—which SCCE does not—and is not inhibited by aprotinin or SBTI (Schechter et al., 1983 and Wintroub et al., 1986) which SCCE is.

Figure 13:
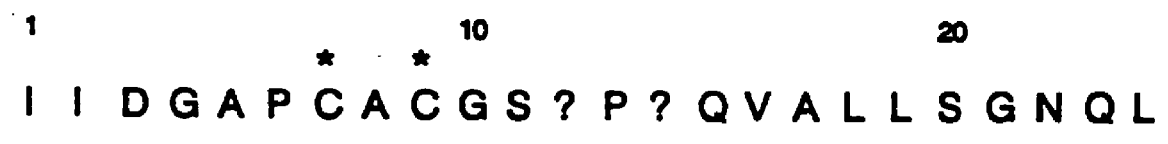

Example 4 describes the partial purification of SCCE from KCl-extracts of corneocytes by means of affinity chromatography on insolubilized soybean trypsin inhibitor (SBTI) and determination of the N-terminal amino acid sequence of SCCE. With unreduced samples yields were good in steps 1–6, but dropped to zero in steps 7 and 9 and the yields in subsequent steps were markedly decreased. Also with reduced samples no amino acid derivatives could be detected in steps 7 and 9, but for subsequent steps where derivatives could be detected there were no steep drops in yields. These results suggest that there are cysteines in positions 7 and 9. It was not possible, however, to detect carboxymethylated cystein in steps 7 and 9 after reduction and treatment with iodoacetic acid (100 mM). The sequence obtained (FIG. 13, SEQ ID NO:3) was identical for reduced and unreduced samples.

Example 5 describes the preparation of SCCE-specific monoclonal antibodies and polyclonal SCCE-specific chicken and rabbit antibodies as well as immunohistochemical studies with the monoclonal antibodies.

Example 6 describes the cloning and sequencing of a cDNA encoding human SCCE. Initially, a cDNA library prepared from mRNA derived from adult human keratinocytes of epidermal origin was screened with anti-SCCE rabbit polyclonal antibodies. One of the antibodies gave a high background signal and was excluded from the extensive screening study at an early stage. Using another polyclonal antibody (D-5), a number of immunoreactive plaques were enriched as anticipated for true positive plaques. No reactivity with the monoclonal antibodies moAb 4 and moAb 9 was, however, observed for any of the plaques. An extensive restriction enzyme characterization and PCR characterization of eleven isolated plaques revealed that no similarities between the various plaques could be detected. Based on this failure to define a "fingerprint" of a probable SCCE CDNA sequence, the strategy had to be modified.

Despite the preferential detection of SCCE immunoreactive material in the suprabasal keratinocytes, a cDNA library prepared from cultured human keratinocytes was used for screening of SCCE cDNA. Such a library may be expected to contain cDNA from basal keratinocytes only. This attempt was based on the observation of a weak, but probably significant immuno-staining using SCCE monoclonal antibodies also of basal keratinocytes.

The plaques were screened using a synthetic 17-mer oligonucleotide probe designed on the basis of the most reliable part of the amino acid sequence, Ile-Ile-Asp-Gly-Ala-Pro (SEQ ID NO:8, aa 1–aa 6) of the experimentally determined amino-terminal sequence of the native SCCE enzyme as described in Example 4. Due to the uncertainty within the experimentally determined amino acid sequence, this hexapeptide was judged to represent one of the most reliable parts. In addition, the possible codons encoding this hexapeptide resulted in the lowest possible degeneration of the DNA probe. The longer experimentally determined sequence Gln-Val-Ala-Leu-Leu-Ser-Gly-Asn-Gln-Leu (SEQ ID NO:3, aa 15–aa 24) was excluded due to the high degree of degeneration of a sequence encoding this peptide sequence. Fourteen positive plaques were identified in the primary screening. These positive plaques were re-screened using the same probe and methods as described above. After the re-screening procedure two positive plaques were identified. The two selected plaques were purified once more, and the size of the inserts was determined by PCR using SYM 1600 and SYM 1601, which were complementary to the two phage arms, as primers and isolated phages as templates. This cloned fragment was subjected to a partial sequence analysis.

Translation of the obtained DNA sequence resulted in an amino acid sequence which was homologous to the experimentally determined protein sequence. However, the sequence lacked a translational start codon. To isolate a full-length cDNA, the obtained DNA fragment was separated on agarose gel and used as a probe allowing hybridization under stringent conditions. To obtain a full-length cDNA, the cDNA library was re-screened twice with this probe using the same methods as described above, except that the hybridization was under stringent conditions, at 65° C. These experiments resulted in the identification and isolation of 45 individual positive plaques which were initially screened by PCR analysis using SYM 1600 or SYM 1601 in combination with SYM 3208 as PCR primers for identification of a plaque containing the entire 5' open reading frame.

After further screening and sequence analysis, the resulting PCR amplified fragments derived from these phages were cloned as described in detail in Example 6 and the results indicated that one of the phages, 205.2.1, contained a full-length insert. The complete nucleotide sequence of the cDNA fragment was determined. The nucleotide sequence (SEQ ID NO:1) contained an open reading frame sufficient to encode the entire amino acid sequence of an SCCE precursor protein consisting of 253 amino acids including a signal peptide and a prepolypeptide (SEQ ID NO:2).

Example 7 describes the detection in human epidermis of two SCCE mRNA-species which was able to hybridize with cDNA probes prepared on the basis of an SCCE cDNA sequence.

Example 8 describes the expression of recombinant SCCE in *E. coli*. The results show that it is possible to produce recombinant SCCE in bacteria.

Example 9 describes the expression of recombinant human SCCE in mammalian cells. Three proteins which show reaction with all available polyclonal rabbit and chicken SCCE antibodies as well as with the deposited monoclonal antibodies are produced. The recombinant proteins which are reactive with the antibodies raised against native SCCE show an apparent molecular weight that is about 1 kDa larger than purified native human SCCE. The recombinant protein does not show any proteolytic activity.

The purification, activation and further characterization of recombinant SCCE is described in Example 10. The inactive pro-form of recombinant SCCE can be activated by proteolytic cleavage with trypsin or endopeptidase Lys-C. It is contemplated that a number of other proteases which cleave a peptide after a basic amino acid, such as endoproteinase Lys-C, papain and plasmin, will be able to activate pro-SCCE into active SCCE. It has been found that the signal peptide consists of 22 amino acids and based on the N-terminal amino acid sequence of native active SCCE, the propeptide consists of seven amino acids. Furthermore it is shown that the produced recombinant SCCE exists in two N-glycosylated forms and one non-glycosylated form which is analogous with the results obtained with active native SCCE.

By the term "stratum corneum chymatryptic enzyme (SCCE)" or "a polypeptide having SCCE activity" is, in its broadest aspect, meant a serine protease or a proform thereof, such as a proenzyme (pro-SCCE) or a fusion protein which can be activated by proteolytic cleavage, said enzyme in its active form being inhibited by the same inhibitors and in a similar manner as the spontaneous cell dissociation that can be induced in model systems with samples of cornified layer of skin incubated at neutral or near neutral pH at physiological temperature.

More specifically, the term "a polypeptide having SCCE activity" thus defines a polypeptide which is different from chymotrypsin and cathepsin G and which in its active form is capable of decomposing the substrate MeO-Suc-Arg-Pro-Tyr-pNA (S-2586), the decomposition by the polypeptide being inhibited by aprotinin, chymostatin and zinc sulphate essentially as described in Examples 3 and 13 and illustrated in FIG. 9 and Table 5.

Even more specifically, the term "a polypeptide having SCCE activity" comprises a polypeptide which is capable of causing the proteolytic degradation of the desmosomal protein desmoglein I during in vitro incubation of plantar stratum corneum.

Such a polypeptide will generally also react with antibodies raised against native SCCE which has been purified from an extract of dissociated plantar stratum corneum cells. Examples of such antibodies are the polyclonal antibodies produced as described in 5.2 and the monoclonal antibodies TE4b and TE9b produced as described in Example 5.1. The monoclonal antibodies are produced by the hybridomas TE4b and TE9b deposited at the European Collection of Animal Cell Cultures, Porton Down, Salisbury, Wiltshire SP4 OJG, United Kingdom, under the accession numbers ECACC 93061817 and ECACC 93061816, respectively, in accordance with the provisions of the Budapest Treaty.

The cloning and sequencing of a cDNA encoding human SCCE is described in Example 6. A nucleotide sequence containing an open reading frame sufficient to encode the entire amino acid sequence of an SCCE precursor protein consisting of 253 amino acids including a signal peptide and a prepolypeptide has been found. The nucleotide sequence is shown in SEQ ID NO:1 and the deduced amino acid sequence of "stratum corneum chymotryptic enzyme (SCCE)" is shown in SEQ ID NO:2.

By the term "pro-SCCE or an analogue or variant thereof" is meant a polypeptide having the amino acid sequence SEQ ID NO:2 or an analogue or variant of said sequence which is produced when a nucleotide sequence of the invention is expressed in a suitable expression system and which upon proteolytic activation gives rise to a serine proteinase which can be inhibited by the same inhibitors as the spontaneous cell dissociation that can be induced in model systems with samples of cornified layer of skin incubated at neutral or near neutral pH at physiological temperature, i.e. about 37° C. Generally, the protein will react with antibodies raised against purified native or recombinant SCCE.

By the term "a SCCE or an analogue or variant thereof" is meant a polypeptide having the amino acid sequence SEQ ID NO:2 or an analogue or variant of said sequence which is produced when a nucleotide sequence of the invention is expressed in a suitable expression system and which is a serine proteinase which can be inhibited by the same inhibitors as the spontaneous cell dissociation that can be induced in model systems with samples of cornified layer of skin incubated at neutral or near neutral pH at physiological temperature, i.e. about 37° C. Generally, the protein will react with antibodies raised against purified native or recombinant SCCE.

By the term "an analogue or variant thereof" is thus meant a polypeptide not having exactly the amino acid sequence shown in SEQ ID NO:2, but still having "SCCE activity" as defined above. Generally, such polypeptides will be polypeptides which vary e.g. to a certain extent in the amino acid composition, or the post-translational modifications e.g. glycosylation or phosphorylation, as compared to the SCCE protein described in the examples.

The term "analogue" or "variant" is thus used in the present context to indicate a protein or polypeptide of a similar amino acid composition or sequence as the characteristic amino acid sequence SEQ ID NO:2 derived from the SCCE protein as described in Example 6, allowing for minor variations that alter the amino acid sequence, e.g. deletions, site directed mutations, insertions of extra amino acids, or combinations thereof, to generate SCCE protein analogues. These modifications may give interesting and useful novel properties of the analogue. The analogous polypeptide or protein may be derived from an animal or a human or may be partially or completely of synthetic origin. The analogue may also be derived through the use of recombinant DNA techniques.

An important embodiment of the present invention thus relates to a polypeptide in which at least one amino acid residue has been substituted with a different amino acid residue and/or in which at least one amino acid residue has been deleted or added so as to result in a polypeptide comprising an amino acid sequence being different from the amino acid sequence shown in SEQ ID NO:2 or a subsequence of said amino acid sequence as defined in the following, but essentially having SCCE activity as defined above.

An interesting embodiment of the invention relates to a polypeptide which is an analogue or subsequence of the polypeptide of the invention comprising from 50 to 250 amino acids, e.g. at least 70 amino acids, at least 100 amino acids, at least 150 amino acids or at least 200 amino acids.

Particular important embodiments of the invention are the polypeptide having the amino acid sequence −7–224 in SEQ ID NO:2 (pro-SCCE) and the polypeptide having the amino acid sequence 1–224 in SEQ ID NO:2 (SCCE).

The term "enzymatically active subsequence" designates a polypeptide sequence which comprises only a part of the polypeptide sequence shown in SEQ ID NO:2 and which has enzymatic activity. Included are also polypeptide subsequences which have been analogized by modifications as explained herein. The specific polypeptide (or polypeptides) which comprises the enzymatically active site is considered particularly interesting.

The predicted amino acid sequence SEQ ID NO:2 has been compared with the amino acid sequences of the enzymes human chymotrypsin (Toulta et al., 1989), human cathepsin G (Salvesen et al., 1987) and human mast cell chymase (Caughey et al., 1991). Although the deduced amino acid sequence contains the conserved active regions of serine proteases, the degree of homology is quite low, about 33–38%. In this respect, it thus appears that SCCE only has moderate similarity with previously known serine proteinases. On the other hand, SCCE is a typical serine proteinase as regards the histidine, aspartate, and serine residues of the active site and conserved regions close to these sites. This is also true for most of the cysteine residues and other highly conserved regions of serine proteinases. At the bottom of the primary specificity pouch (residue 189 in chymotrypsin) there is a serine residue in human chymotrypsin, mast cell chymase, and prostate-specific antigen and an alanine residue in human cathepsin G. In SCCE, on the other hand, this position is occupied by an asparagine residue. This could explain the finding that although SCCE undoubtedly has chymotryptic activity, its relative activity toward various chromogenic peptide substrates differs from chymotrypsin and cathepsin G, as does the inhibitory efficiency of chymostatin, a low molecular mass inhibitor of chymotrypsin-like enzymes.

A comparison between the sequences of human chymotrypsin, human cathepsin G and human mast cell chymase and that of SCCE is shown in the following alignment of the sequences.

```
SCCE      IIDGAPCARGSHPWQVALLSGNQLHH...CGGVLVNERWVLTAAHCKMN
HUMCTRP   IVNGEDAVPGSWPWQVSLQDKTGFHF...CGGSLISEDWVVTAAHCGVR
HUMCHTG   IIGGRESRPHSRPYMAYLQIQSPAGQS.RCGGFLVREDFVLTAAHCWGS
HUMCHYM   IIGGTECKPHSRPYMAYLEIVTSNGPSKFCGGFLIRRNFVLTAAHCAGR
                            .                        .
                           20                       50
SCCE      EYTV..HLGSDTLGDRRA..QRIKASKSFR.HPGYSTQTHVNDLMLVKLN
HUMCTRP   TSDVVVAGEFDQGSDEENI.QVLKIAKVFK.NPKFSILTVNNDITLLKLA
HUMCHTG   NINV..TLGAHNIQRRENT.QQHITARRAIRHPQYNQRTIQNDIMLLQLS
HUMCHYM   SITV..TLGAHNITEEEDTWQKLEVIKQF.RHPKYNTSTLHHDIMLLKLK
```

-continued

```
                        80
SCCE     SQARLSSMVKKVRLPSRC..E..PPGTTCTVSGWGTTTSPDVTFPSDLMC
HUMCTRP  TPARFSQTVSAVCLPSADDDF..PAGTLCATTGWGKTKYNANKTPDKLQQ
HUMCHTG  RRVRRNRNVNPVALPRAQ..EGLRPGTLCTVAGWGRVSMRRGTDTLREVQ
HUMCHYM  EKASLTLAVGT..LPFPSQFNFVPPGRMCRVAGWGRTGVLKPGSDTLQEV 110                        140
SCCE     VDVKLISPQDCTEVYKDLLENSMLCAGIPDSKKNA.CNGDSGGPLVCRGT
HUMCTRP  AALPLLSNAECKKSWGRRITDVMICAGA...GVSS.CMGDSGGPLVCQKD
HUMCHTG  LRVQRDRQ..CLRIFGSYDPRRQICVGDRRERKAAFK.GDSGGPLLCNNV
HUMCHYM  KLRLMDPQA.CSHFRDFDHNL.QLCVGNPRKTKSAFK.GDSGGPLLCAGV

170                   ↑    200
                                  *
SCCE     LQ....GLVSWGTFPCGQ.PNDPGVYTQVCKFTKWINDTMKKHR (SEQ ID NO:12)
HUMCTRP  GAWTLVGIVSWGSDTCST.SS.PGVYARVTKLIPWVQKILAAN (SEQ ID NO:13)
HUMCHTG  AH....GIVSYGKSSGVP....PEVFTRVSSFLPWIRTTMRSFKLLDOMETPL (SEQ ID NO:14)
HUMCHYM  AQ....GIVSYGRSDAKP....PAVFTRISHYRPWINQILQAN (SEQ ID NO:15)

230
```

Aligning carried out manually.

| | |
|---|---|
| HUMCTRP = | human chymotrypsin (Touita et al., BBRC 158:569–575, 1989) |
| HUMCHTG = | human cathepsin G (Salvesen et al., Biochemistry 26:2289–2293, 1987) |
| HUMCHYM = | human mast cell chymase (Caughey et al., J. Biol. Chem. 266:12956–12963, 1991) |

Homologies:

HUMCTRP/SCCE: 85/224 = 38%
HUMCHTG/SCCE: 74/224 = 33%
HUMCHYM/SCCE: 74/224 = 33%
HUMCHTG/HUMCHYM: 109/226 = 48%

Numbering refers to chymotrypsinogen
Underlinings:
Conserved regions near the active site (Ile 15, His 57, Asp 102, Ser 195 in chymotrypsin) and of the primary specificity pocket of chymotrypsin (Ser 189, Ser 213-Trp 215, Gly 226 in chymotrypsin).
Asterisk: Possible N-glycosylation site in SCCE An important embodiment of the present invention thus relates to a polypeptide having an amino acid sequence from which a consecutive string of 20 amino acids is homologous to a degree of at least 80% with a string of amino acids of the same length selected from the amino acid sequence shown in SEQ ID NO:2.

Polypeptide sequences of the invention which have a homology of at least 80% such as at least 85%, e.g. 90%, with the polypeptide shown in SEQ ID NO:2 constitute important embodiments. As the sequence shown in SEQ ID NO:2 seems to be quite unique, the scope of the invention comprises polypeptides for which the degree of homology to a similar consecutive string of 20 amino acids selected from the amino acid sequence shown in SEQ ID NO:2 may not be more than 55%, although preferably not more than 70%. Such sequences may be derived from similar proteins from other species, e.g. other mammals such as mouse, rat, rabbit, guinea pig, pig or cow. As minor parts of the sequence may show considerable similarities with other serine proteases, the scope of the invention also includes peptides with a degree of homology of at least 95%, and most preferably at least 99% homology to a similar consecutive string of 20 amino acids selected from the amino acid sequence shown in SEQ ID NO:2.

By the term "sequence homology" is meant the identity in sequence of amino acids in segments of two or more amino acids in the match with respect to identity and position of the amino acids of the polypeptides.

The term "homologous" is thus used here to illustrate the degree of identity between the amino acid sequence of a given polypeptide and the amino acid sequence shown in SEQ ID NO:2. The amino acid sequence to be compared with the amino acid sequence shown in SEQ ID NO:2 may be deduced from a nucleotide sequence such as a DNA or RNA sequence, e.g. obtained by hybridization as defined in the following, or may be obtained by conventional amino acid sequencing methods. The degree of homology is preferably determined on the amino acid sequence of a mature polypeptide, i.e. without taking any leader sequence into consideration. Generally, only coding regions are used when comparing nucleotide sequences in order to determine their internal homology.

In the present context the term "polypeptide which is recognized by at least one of the deposited antibodies" is intended to include an amino acid sequence which comprises amino acids constituting a substantially consecutive stretch in terms of linear or spatial conformation of any subsequence of the polypeptide shown in SEQ ID NO:2 which is recognized by at least one of the deposited antibodies. As it is well-known within the art, also secondary or tertiary conformation may have interesting and useful properties and may constitute epitopes. The deposited antibodies TE4b and TE9b seem to recognize conformational epitopes of SCCE.

It has been shown that a polyclonal rabbit antibody prepared as described in Example 5.2.2 produced a granular staining of the stratum granulosum and a rather diffuse staining of the lower stratum corneum in immunofluorescence microscopy.

Antibodies raised against purified native or recombinant SCCE will generally bind to suprabasal cells in keratinized (cornified) human squamous epithelium but not to epithelial cells in non-cornified squamous epithelium. These antibodies will also bind to the intercellular space of the cornified layer of human skin.

Antibodies reactive with the polypeptides of the invention are suitable for a number of purposes as listed in the following:

For purification of proteins:
The antibodies can be used to purify the polypeptide(s) or its analogues from the biological samples, using the affinity chromatography or the immuno-precipitation techniques.

For diagnosis and therapy:

The monoclonal antibodies against the polypeptide(s) or its analogues can be used in the diagnosis and therapy of disease conditions in animals and humans. The diagnostic agent may be an antibody with the specificity for the polypeptide of the invention. The antibody can be coupled to another protein or a solid support and/or can be used in the agglutination tests or the colour developing tests. Such antibodies can also be used to quantitate SCCE polypeptides or analogues thereof in biological samples using the standard histochemistry or immunochemistry techniques.

In one of its aspects, the invention relates to a nucleotide sequence encoding a polypeptide of the invention as defined above. In particular, the invention relates to a nucleotide sequence comprising substantially the sequence shown in SEQ ID NO:1. Other important embodiments relate to a nucleotide sequence encoding a polypeptide having a subsequence of the amino acid sequence SEQ ID NO:2 such as a nucleotide sequence which encodes a polypeptide comprising amino acid sequence −7–224 of SEQ ID NO:2 or a polypeptide which comprises amino acid sequence 1–224 of SEQ ID NO:2.

The present invention also relates to a nucleotide sequence which hybridizes with the nucleotide sequence shown in SEQ ID NO:1 under high stringency conditions as described in Examples 7 and Example 9.

In another aspect, the invention relates to a nucleotide sequence having the nucleotide sequence shown in SEQ ID NO:1 or an analogue or subsequence thereof which 1) has a homology with the sequence shown in SEQ ID NO:1 of at least 90%, and/or
2) encodes a polypeptide, the amino acid sequence of which is at least 80% homologous with the amino acid sequence shown in SEQ ID NO:2, and/or
3) encodes a polypeptide which is bound by the monoclonal antibody produced by the hybridoma cell line TE4b which was deposited on 18 Jun. 1993 at ECACC and has obtained the provisional deposition number ECACC 93061817 or the monoclonal antibody produced by the hybridoma cell line TE9b which was deposited on 18 Jun. 1993 at ECACC and has obtained the provisional deposition number 93061816, and/or
4) encodes a polypeptide which is bound by a polyclonal antiserum raised against native SCCE which has been purified from an extract of dissociated plantar stratum corneum cells.

Within the scope of the present invention is also a modified nucleotide sequence which differs from a nucleotide sequence as defined above in that at least one nucleotide has been deleted, substituted or modified or at least one additional nucleotide has been inserted so as to result in a nucleotide sequence which encodes a polypeptide having SCCE activity.

In the present specification and claims, the term "subsequence" designates a sequence which preferably has a size of at least 15 nucleotides, more preferably at least 18 nucleotides, and most preferably at least 21 nucleotides. In a number of embodiments of the invention, the subsequence or analogue of the nucleotide sequence of the invention will comprise at least 48 nucleotides, such as at least 75 nucleotides or at least 99 nucleotides. The "subsequence" should conform to at least one of the criteria 1)–4) above or should hybridize with the nucleotide sequence shown in SEQ ID NO:1.

It is well known that small fragments are useful in PCR techniques as is described herein. Such fragments and subsequences may among other utilities be used as probes in the identification of mRNA fragments of the nucleotide sequence of the invention as described in Example 7.

The term "analogue" with regard to the DNA fragments of the invention is intended to indicate a nucleotide sequence which encodes a polypeptide identical or substantially identical to the polypeptide encoded by a DNA fragment of the invention. It is well known that the same amino acid may be encoded by various codons, the codon usage being related, inter alia, to the preference of the organisms in question expressing the nucleotide sequence. Thus, one or more nucleotides or codons of the DNA fragment of the invention may be exchanged by others which, when expressed, result in a polypeptide identical or substantially identical to the polypeptide encoded by the DNA fragment in question.

Also, the term "analogue" is used in the present context to indicate a DNA fragment or a DNA sequence of a similar nucleotide composition or sequence as the characteristic DNA sequence SEQ ID NO:1 encoding the amino acid sequence constituting SCCE polypeptides, allowing for minor variations which do not have a significant adverse effect on the enzymatic activity of the analogue as compared to the activity of native SCCE protein as described in Example 3. By the term "significant adverse effect" is meant that the enzymatic activity of the analogue should be at least 50%, more preferably at least 60%, even more preferably at least 70% such as at least 75% of the enzymatic activity of native SCCE, when determined e.g. as described in Example 3. The analogous DNA fragment or DNA sequence may be derived from an organism such as an animal or a human or may be partially or completely of synthetic origin. The analogue may also be derived through the use of recombinant DNA techniques.

Furthermore, the terms "analogue" and "subsequence" are intended to allow for variations in the sequence such as substitution, insertion (including introns), addition and rearrangement of one or more nucleotides, which variations do not have any substantial adverse effect on the polypeptide encoded by the DNA fragment or a subsequence thereof.

The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "rearrangement" is intended to mean that two or more nucleotide residues have been exchanged within the DNA or polypeptide sequence, respectively. The DNA fragment may, however, also be modified by mutagenesis either before or after inserting it into the organism.

The terms "fragment", "sequence", "subsequence" and "analogue", as used in the present specification and claims with respect to fragments, sequences, subsequences and analogues according to the invention, should of course be understood as not comprising these phenomena in their natural environment, but rather, e.g., in isolated, purified, in vitro or recombinant form.

In one embodiment of the invention, detection and/or quantitation of SCCE polypeptide mRNA may be obtained by extracting RNA from cells or tissues and converting it into cDNA for subsequent use in the polymerase chain reaction (PCR). The PCR primer(s) may be synthesized based on a DNA fragment of the invention such as the DNA fragment shown in SEQ ID NO:1. This method for detection and/or quantitation may be used as a diagnostic method for diagnosing a disease condition in which an SCCE MRNA is expressed in higher or lower amounts than normally.

Also within the scope of the present invention is a diagnostic agent comprising a nucleotide probe which is capable of detecting a nucleotide sequence of the invention as well as a method for diagnosing diseases in which the SCCE expression is deregulated and/or diseases where the SCCE gene is mutated, comprising subjecting a sample from a patient suspected of having a disease where a higher amount of SCCE than normally is present or a mutated form of SCCE, to a PCR analysis in which the sample is contacted with a diagnostic agent as described above, allowing any nucleotide sequence to be amplified and determining the presence of any identical or homologous nucleotide sequences in the sample.

The polypeptides of the invention can be produced using recombinant DNA technology. An important embodiment of the present invention relates to an expression system comprising a nucleotide sequence of the invention.

The organism which is used for the production of the polypeptide of the invention may be a higher organism, e.g. an animal, or a lower organism, e.g. a microorganism such as *E. coli*. Irrespective of the type of organism used, the DNA fragment of the invention is introduced into the organism either directly or by means of a suitable vector. Alternatively, the polypeptides may be produced in the mammalian cell lines by introducing the DNA fragment or an analogue or a subsequence thereof of the invention either directly or by means of an expression vector.

The DNA fragment or an analogue or a subsequence thereof can also be cloned in a suitable stable expression vector and then put into a suitable cell line. The cells producing the desired polypeptides are then selected based on levels of productivity under conditions suitable for the vector and the cell line used. The selected cells are grown further and form a very important and continuous source of the desired polypeptides.

An example of a specific analogue of the DNA sequence of the invention is a DNA sequence which comprises the DNA sequence shown in SEQ ID NO:1 or a part thereof and which is particularly adapted for expression in *E. coli*. This DNA sequence is one which, when inserted in *E. coli* together with suitable regulatory sequences, results in the expression of a polypeptide having substantially the amino acid sequence shown in SEQ ID NO:2 or a part thereof. Thus, this DNA sequence comprises specific codons recognized by *E. coli*. An example of this embodiment is described in Example 8.

In the present context, the term "gene" is used to indicate a DNA sequence which is involved in producing a polypeptide chain and which includes regions preceding and following the coding region (5'-upstream and 3'-downstream sequences) as well as intervening sequences, introns, which are placed between individual coding segments, exons, or in the 5'-upstream or 3'-downstream region. The 5'-upstream region comprises a regulatory sequence which controls the expression of the gene, typically a promoter. The 3'-downstream region comprises sequences which are involved in termination of transcription of the gene and optionally sequences responsible for polyadenylation of the transcript and the 3'-untranslated region.

In line with the above, the invention relates to an expression system comprising a nucleotide sequence as described above encoding a polypeptide of the invention, the system comprising a 5'-flanking sequence capable of mediating expression of said nucleotide sequence.

In particular, the invention relates to a replicable expression vector which carries and is capable of mediating the expression of a nucleotide sequence according to the invention. A specific embodiment of the present invention relates to a replicable expression vector designated pS507 which has been deposited on 11 May 1993 with the collection of Deutsche Sammlung von Mikroorganismen und Zellkulturen GmbH (DSM) under the accession number DSM 8282 in accordance with the provisions of the Budapest Treaty, and expression vectors expressing nucleotide sequences which differ from the nucleotide sequence of the said deposited expression vector, but which code for the same polypeptide or an analogue or variant thereof which has SCCE activity.

In other words, the scope of the invention also comprises a replicable expression vector as described above, wherein the nucleotide sequence expressed is one which differs from the nucleotide sequence of the deposited vector in that at least one nucleotide has been deleted, substituted or modified or at least one additional nucleotide has been inserted so as to result in a nucleotide sequence which encodes a polypeptide having SCCE activity.

Moreover, the invention relates to a plasmid designated pS500, which has been deposited on 11 May 1993 with the collection of Deutsche Sammlung von Mikroorganismen und Zellkulturen GmbH (DSM) under the accession number DSM 8281 in accordance with the provisions of the Budapest Treaty, and plasmids having a nucleotide sequence which differs from the nucleotide sequence shown in SEQ ID NO:1, but which codes for the polypeptide shown in SEQ ID NO:2 or an analogue or variant thereof which has SCCE activity, or which hybridizes with the nucleotide sequence shown in SEQ ID NO:1 or a part thereof under stringent hybridization conditions.

Within the scope of the present invention is also a non-human organism which carries an expression system according to the invention. Organisms which may be used in this aspect of the invention comprise a microorganism such as a bacterium of the genus Bacillus, Escherichia or Salmonella, a yeast such as Saccharomyces, Pichia, a protozoan, or cell derived from a multicellular organism such as a fungus, an insect cell, a plant cell, a mammalian cell or a cell line. If the organism is a bacterium, it is preferred that the bacterium is of the genus Escherichia, e.g. *E. coli*.

The invention furthermore relates to a plasmid vector containing a DNA sequence coding for a polypeptide of the invention or a fusion polypeptide as defined herein. In one particular important embodiment, the DNA fragment or an analogue or subsequence thereof of the invention or a fusion DNA fragment of the invention as defined herein may be carried by a replicable expression vector which is capable of replicating in a host organism or a cell line.

The vector may in particular be a plasmid, phage, cosmid, mini-chromosome or virus. In an interesting embodiment of the invention, the vector may be a vector which, when introduced in a host cell, is integrated in the host cell genome.

If a higher organism is used, transgenic techniques may be employed for the production of the polypeptides. Examples of suitable animals are sheep, cattle, pigs, etc. A DNA fragment encoding a polypeptide of the invention is expressed in the desired tissue under control of tissue specific regulatory elements. The resulting protein may then be subjected to post-translational modifications so as to obtain the polypeptide of the invention.

The transgenic non-human mammals of the invention are produced by introducing a "transgene" into an embryonal target cell of the animal of choice. In one aspect of the invention, a transgene is a DNA sequence which is capable of producing a desirable phenotype when contained in the genome of cells of a transgenic non-human mammal. In specific embodiments, the transgene comprises a DNA sequence encoding a polypeptide of the invention, the transgene being capable of being expressed to produce the polypeptide.

The incorporation of the expression system into the germline of the mammal may be performed using any suitable technique, e.g. as described in Hogan et al., 1986 or in WO 93/04172.

In one particular aspect of the invention, the nucleotide sequence of the invention may comprise another nucleotide sequence encoding a polypeptide different from or identical to the polypeptide of the invention fused in frame to a nucleotide sequence of the sequence shown in SEQ ID NO:1 or an analogue thereof encoding a SCCE polypeptide with the purpose of producing a fused polypeptide which polypeptide constitutes yet another interesting aspect of the invention, see e.g. Example 8. When using recombinant DNA technology the fused DNA sequences may be inserted into a suitable vector or genome. Alternatively, one of the nucleotide sequences is inserted into the vector or genome already containing the other nucleotide sequence. A fusion polypeptide can also be made by inserting the two nucleotide sequences separately and allowing the expression to occur. The host organism, which may be of eukaryotic or prokaryotic origin, is grown under conditions ensuring expression of fused sequences. The fused polypeptide is then purified and the polypeptide of the invention separated from its fusion partner using a suitable method.

One aspect of the invention thus relates to a method of producing a polypeptide of the invention, comprising the following steps of:

(a) inserting a nucleotide sequence of the invention into an expression vector, (b) transforming a suitable host organism with the vector produced in step (a), (c) culturing the host organism produced in step (b) under suitable conditions for expressing the polypeptide, (d) harvesting the polypeptide, and (e) optionally subjecting the polypeptide to post-translational modification.

Within the scope of the present invention is also a method as described above wherein the polypeptide produced is isolated by a method comprising one or more steps like affinity chromatography using immobilized native or recombinant SCCE polypeptide or antibodies reactive with said polypeptide and/or other chromatographic and electrophoretic procedures.

The polypeptide produced as described above may be subjected to post-translational modifications as a result of thermal treatment, chemical treatment (formaldehyde, glutaraldehyde etc.) or enzyme treatment (peptidases, proteinases and protein modification enzymes). The polypeptide may be processed in a different way when produced in an organism as compared to its natural production environment. As an example, glycosylation is often achieved when the polypeptide is expressed by a cell of a higher organism such as yeast or preferably a mammal. Glycosylation is normally found in connection with amino acid residues Asn, Ser, Thr or hydroxylysine. It may or may not be advantageous to remove or alter the processing characteristics caused by the host organism in question.

Subsequent to the expression according to the invention of the polypeptide in an organism or a cell line, the polypeptide can either be used as such or it can first be purified from the organism or cell line. If the polypeptide is expressed as a secreted product, it can be purified directly. If the polypeptide is expressed as an associated product, it may require the partial or complete disruption of the host before purification. Examples of the procedures employed for the purification of polypeptides are: (i) immunoprecipitation or affinity chromatography with antibodies, (ii) affinity chromatography with a suitable ligand, (iii) other chromatography procedures such as gel filtration, ion exchange or high performance liquid chromatography or derivatives of any of the above, (iv) electrophoretic procedures like polyacrylamide gel electrophoresis, denaturating polyacrylamide gel electrophoresis, agarose gel electrophoresis and isoelectric focusing, (v) any other specific solubilization and/or purification techniques.

The present invention also relates to a substantially pure SCCE polypeptide. In the present context, the term "substantially pure" is understood to mean that the polypeptide in question is substantially free from other components, e.g. other polypeptides or carbohydrates, which may result from the production and/or recovery of the polypeptide or otherwise be found together with the polypeptide. The purity of a protein may be assessed by SDS gel electrophoresis performed as described in Example 3.

The polypeptide may be purified as described in Example 4 by SBTI affinity chromatography or by affinity chromatography on an immobilized antibody, such as the antibody TE4b, according to procedures known to those skilled in the art. A high purity of the polypeptide of the invention may be advantageous when the polypeptide is to be used in a pharmaceutical or cosmetic composition. Also due to its high purity, the substantially pure polypeptide may be used in a lower amount than a polypeptide of a conventional lower purity for most purposes.

In one aspect of the invention, the pure polypeptide may be obtained from a suitable cell line which expresses a polypeptide of the invention as described in Example 9. Also, a polypeptide of the invention may be prepared by the well known methods of liquid or solid phase peptide synthesis utilizing the successive coupling of the individual amino acids of the polypeptide sequence. Alternatively, the polypeptide can be synthesized by the coupling of individual amino acids forming fragments of the polypeptide sequence which are later coupled so as to result in the desired polypeptide. These methods thus constitute another interesting aspect of the invention.

A very important aspect of the invention relates to a pharmaceutical composition, a cosmetic composition or a skin care composition comprising a polypeptide having SCCE activity and a pharmaceutically and/or cosmetically acceptable excipient. The composition may comprise purified native protein or a recombinant polypeptide of the invention, or a proenzyme or fusion protein form of the polypeptide of the invention which can be activated by proteolytic cleavage. The proenzyme form of the polypeptides of the invention may be regarded as a "prodrug", i.e. a compound which upon appropriate proteolytic cleavage is converted to the active form.

Particularly, but not exclusively, the present invention relates to compositions suitable for topical application, e.g. application onto the skin.

Pharmaceutical compositions of the invention suitable for topical administration may be creams, ointments, lotions, liniments, gels, solutions, suspensions, pastes, sticks, sprays, shampoos, soaps, hair conditioners or powders.

The topical administration may be an administration onto or close to the parts of the body presenting the pathological changes in question, e.g. onto an exterior part of the body such as a skin surface. The application may be a simple smearing on of the composition, or it may involve any device suited for enhancing the establishment of contact between the composition and the pathological lesions such as the use of occlusive dressings, e.g. occlusion plasters provided with the composition of the invention. The compositions may be impregnated or distributed onto pads, plasters, strips, gauze, sponge materials, cotton wool pieces, etc. Optionally, a form of injection of the composition into or near the lesions may be employed.

The topical compositions according to the present invention may comprise 1–80% of the active compound by weight, based on the total weight of the preparations, such as 0.001–25% w/w of the active compound, e.g., 0.1–10%, 0.5–5%, or 2–5%. More than one active compound may be incorporated in the composition; i.e. compositions comprising SCCE, pro-SCCE or an SCCE inhibitor in combination with other pharmaceutical and/or cosmetic compounds are also within the scope of the invention. The composition is conveniently applied 1–10 times a day, depending on the type, severity and localization of the lesions.

For topical application, the preparation may be formulated in accordance with conventional pharmaceutical practice with pharmaceutical excipients conventionally used for topical applications. The nature of the vehicle employed in the preparation of any particular composition will depend on the method intended for administration of that composition. Vehicles other than water that can be used in compositions can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

solvents, such as water, methylene chloride, isopropanol, castor oil, ethylene glycol monoethyl ether, diethylene glycol monobutyl ether, diethylene glycol monoethyl ether, dimethyl sulfoxide, tetrahydrofuran, vegetable and animal oils, glycerol, ethanol, propanol, propylene glycol, and other glycols or alcohols, fixed oils;

humectants or moistening agents, such as glycerin, sorbitol, sodium 2-pyrrolidone-5-carboxylate, soluble collagen, dibutyl phthalate, gelatin;

powders, such as chalk, talc, kaolin, starch and derivatives thereof, gums, colloidal silicon dioxide, sodium polyacrylate, chemically modified magnesium aluminium silicate, hydrated aluminium silicate, carboxyvinyl polymer, sodium carboxymethyl cellulose, ethylene glycol monostearate;

gelling or swelling agents, such as pectin, gelatin and derivatives thereof, cellulose derivatives such as methyl cellulose, carboxymethyl cellulose or oxidised cellulose, cellulose gum, guar gum, acacia gum, karaya gum, tragacanth gum, bentonite, agar, alginates, carbomer, gelatine, bladderwrack, ceratonia, dextran and derivatives thereof, ghatti gum, hectorite, ispaghula husk, xanthan gum;

polymers, such as polylactic acid or polyglycolic acid polymers or copolymers thereof, paraffin, polyethylene, polyethylene oxide, polyethylene glycol, polypropylene glycol, polyvinylpyrrolidone;

surfactants, such as non-ionic surfactants, e.g. glycol and glycerol esters, macrogol ethers and esters, sugar ethers and esters, such as sorbitan esters, ionic surfactants, such as amine soaps, metallic soaps, sulfated fatty alcohols, alkyl ether sulfates, sulfated oils, and ampholytic surfactants and lecitins;

buffering agents, such as sodium, potassium, aluminium, magnesium or calcium salts (such as the chloride, carbonate, bicarbonate, citrate, gluconate, lactate, acetate, gluceptate or tartrate).

For topical application, the pH of the composition may in principle be within a very broad range such as 3–9. In a preferred embodiment of the invention, a pH at which a suitable proteolytic activity of the polypeptide is obtained, e.g. a pH of about 4 to 8 is preferred. Conventional buffering agents as described above may be used to obtain the desired pH.

The preparation of the invention may also contain other additives such as stabilizing agents, preservatives, solubilizers, colouring agents, chelating agents, gel forming agents, ointment bases, pH-regulators, anti-oxidants, perfumes and skin protective agents, etc. If the composition is in the form of a shampoo or soap, the composition may further comprise foaming agents, pearling agents and/or conditioners.

Typical preservatives include the parabens, formaldehyde, Kathon CG, Bronidox, Bronopol, p-chloro-m-cresol, chlorhexidine, benzalkonium chloride, etc.

Conventional ingredients may be used where the compositions of the invention are in the form of a shampoo or a soap, and typical soap and shampoo bases include such components as betaine, sodium lauryl sulphate, nonylphenol, imidazole, sulphosuccinate, refattening agents, humectants and conditioners.

Furthermore, it may be advantageous to provide modified release preparations in which the active compound is incorporated into a polymer matrix, or nanoparticles, or liposomes or micelles, or adsorbed on ion exchange resins, or carried by a polymer.

Compositions may be formulated according to conventional pharmaceutical practice and may be:

Semisolid formulations: Gels, pastes, mixtures.

Liquid formulations: Solutions, suspensions, drenches, emulsions.

As indicated, a pharmaceutical composition of the invention may comprise a polypeptide of the invention itself or a functional derivative thereof, or a combination of such compounds. Examples of suitable functional derivatives include pharmaceutically acceptable salts, particularly those suitable for use in a cutaneous environment. Examples include pharmaceutically acceptable salts of the amino function, for example salts with acids yielding anions which are pharmaceutically acceptable, particularly in a cutaneous environment. Examples include phosphates, sulphates, nitrate, iodide, bromide, chloride, borate as well as anions derived from carboxylic acids including acetate, benzoate, stearate, etc.

Other derivatives of the amino function include amides, imides, ureas, carbamates, etc.

Other suitable derivatives include derivatives of the carboxyl group of a polypeptide of the invention, including salts, esters and amides. Examples include salts with pharmaceutically acceptable cations, e.g. lithium, sodium, potassium, magnesium, calcium, zinc, aluminium, ferric, ferrous, ammonium and lower($C_{1-6}$)-alkylammonium salts. Esters include lower alkyl esters.

The examples of compositions in Example 11 illustrate examples of pharmaceutical cosmetic and skin-care formulations according to the present invention, but should not in any way be limiting the scope of the compositions of the invention.

It is contemplated that cosmetic compositions or skin care compositions comprising native or recombinant SCCE are active against acne, xeroderma or other hyperkeratotic conditions such as callosities and keratosis pilaris. There are different stages in acne vulgaris. It is contemplated that it is useful to administer SCCE in the stages wherein there is a disturbed keratinization in the ducts of the sebaceous glands which leads to the formation of comedones and plugging whereas it might be advantageous to administer a substance which inhibits SCCE in the stages wherein an inflammatory acne lesion is the predominant feature.

One aspect of the invention thus relates to the use of a polypeptide for the treatment or prophylaxis of acne, xeroderma or other hyperkeratotic conditions such as callosities and keratosis pilaris.

Based upon the scientific findings described above, it is contemplated that pharmaceutical compositions comprising native or recombinant SCCE are useful for treatment or prophylaxis of the various ichthyoses, acne, psoriasis or other inflammatory skin diseases such as eczemas with hyperkeratosis, microbial infections and wound healing, particularly when applied topically.

Another aspect of the invention relates to the use of a polypeptide having SCCE activity for the manufacture of a pharmaceutical composition for treatment or prophylaxis of the various ichthyoses, acne, psoriasis or other inflammatory skin diseases with hyperkeratosis such as eczemas.

A further aspect of the invention relates to a method of treating and/or preventing the various ichthyoses, acne, psoriasis or other inflammatory skin diseases with hyperkeratosis such as eczemas, the method comprising administering to a patient in need thereof a therapeutically or prophylactically effective amount of a polypeptide having SCCE activity. The treatment may be prophylactic, palliative or curative.

It is contemplated that a "cascade system" of proteolytic enzymes exists in the cutaneous environment which is similar to the plasminogen activation system. SCCE is presumed to be one of the end products of this system. It is contemplated that the activity of SCCE can be inhibited by means of an "SCCE inhibitor".

In a number of skin diseases, such as autoimmune pemphigus diseases or acantholytic diseases, e.g. familiar pemphigus and Darier's disease, there is impaired cohesion between keratinocytes in the non-cornified viable epidermal layer (see Disorders of cell cohesion in viable epidermis). It is contemplated that this process is mediated by proteinases and thus, that it may be treated by administering a compound which is capable of inhibiting the enzymatic activity of native SCCE. It might also be advantageously to administer an SCCE inhibitor for the treatment of psoriasis and other inflammatory skin diseases in conditions where an inflammatory component is the predominant feature.

In another aspect, the present invention thus relates to the use of a SCCE inhibitor which has an inhibitory effect on the enzymatic activity of native SCCE for the manufacture of a pharmaceutical composition for treatment or prophylaxis of autoimmune pemphigus diseases or acantholytic diseases such as familiar pemphigus and Darier's disease.

In the present context, the term "SCCE inhibitor" refers to an existing or novel compound which is able to interact with an enzymatically active polypeptide sequence or subsequence of the invention or an analogue thereof in such a way that the SCCE activity is decreased. A decrease can be measured e.g. by performing an experiment as outlined in Example 3.2 using the potential SCCE inhibitor as inhibitor. Said compounds can be organic molecules, small peptides or large polypeptides or derivatives of any of the above. Such an approach can find use in a drug screening programme for identifying SCCE inhibitors.

A further embodiment of the present invention thus relates to a method for identification of a compound which has an effect on the enzymatic activity of native SCCE comprising use of a recombinant polypeptide according to the invention.

In particular, the present invention relates to a method for identification of a compound which has an inhibitory effect on the enzymatic activity of native SCCE.

In another aspect, the present invention relates to a method for identification of a compound which is capable of enhancing the enzymatic activity of native or recombinant SCCE.

An important use of the recombinant polypeptides of the present invention is in a drug screening assay. The polypeptides of the invention can be used in a drug screening system. The invention thus also relates to a method for identification of a compound which is capable of converting the proenzyme form of SCCE into active SCCE comprising use of a polypeptide of the invention.

Within the concept of this invention is also the use of an amino acid sequence as defined above for the deduction of the three-dimensional structure of an SCCE polypeptide for use in the design of a substance capable of binding to the SCCE polypeptide, in particular for use in the design in a drug substance which binds to the active site of the enzyme.

Important aspects of the invention are finally various methods of regulating the activity exerted by an SCCE polypeptide. This activity may have important implication for various disease conditions as described above.

A DNA or RNA fragment complementary to at least part of the mRNA corresponding to the polypeptide of invention or an analogue thereof may be effective in arresting the translation of the SCCE mRNAs in human cells and thereby inhibiting the synthesis of the polypeptide(s). This approach, which may be of interest in disease states wherein a higher than normal expression of SCCE is found such as autoimmune pemphigus diseases or acantholytic diseases such as familiar pemphigus and Darier's disease, is more commonly known as antisense oligo therapy and thus, the present invention comprises such approaches.

EXAMPLES

Example 1

Evidence that cell shedding from the surface of the cornified surface layer of the skin involves degradation of desmosomal proteins and that the responsible enzyme seems to be a chymotrypsin-like serine proteinase which can be inhibited by zinc ions 1.1. Desquamation in the stratum corneum The aim of the study was to elucidate the nature of the mechanisms responsible for cell cohesion and surface cell dissociation (desquamation) in the cornified layer of skin, the stratum corneum. A flake of stratum corneum, 0.3–0.6 mm thick, was cut parallel to the skin surface from under a heel of a volunteer with normal skin. The tissue piece was soaked in phosphate buffered saline with 0.1% sodium azide for 3 hours at room temperature and the loosely attached cells from the surface that had faced outwards in vivo were scraped off. One mm thick slices cut perpendicular to the tissue surface were then placed in a medium containing 0.1 M tris-HCl pH 8, 5 mM EDTA 0.1% sodium azide, and 0.45% agarose, just before gelling of the medium due to the presence of the agarose. After incubation times 0, 5 and 15 hours at 37° C. gel pieces with tissue were frozen on dry ice. 20 μm cryostat sections were cut perpendicular to the skin surface in a cryostat, mounted, and examined in a phase contrast microscope. A continuous unipolar shedding of cells from pieces of plantar stratum corneum incubated in vitro was observed (FIG. 1). Cells were shed only from the tissue surface that had faced outwards in vivo. The observed process thus mimicked desquamation.

1.2. Effects of temperature, pH, and enzyme inhibitors

Figure 2:
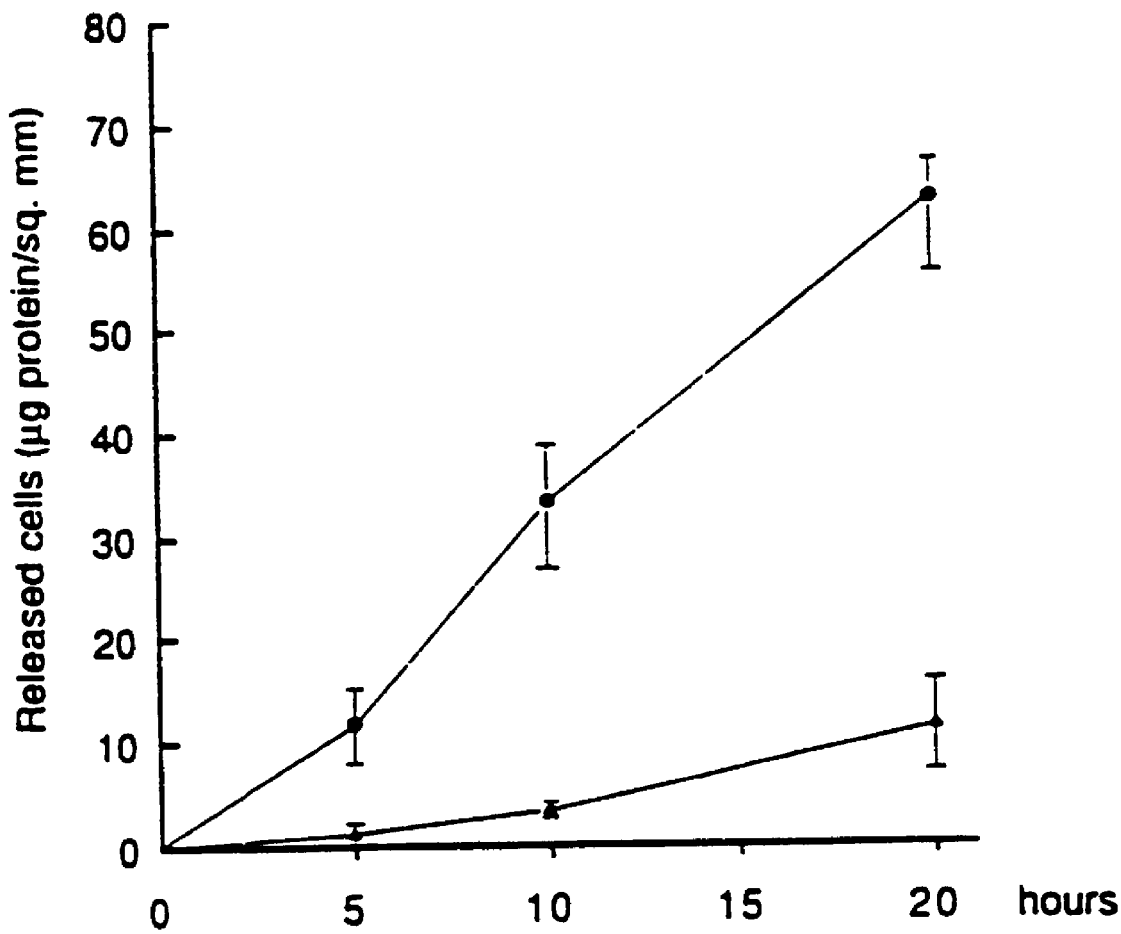

A method to quantify the cell shedding was then developed, which allowed studies on the effects of various parameters such as temperature, pH, and enzyme inhibitors. Cylinders of plantar stratum corneum with diameter 3 mm were prepared with a biopsy punch from flakes of tissue taken and freed from loosely attached surface cells as described above in 1.1. The cylinders (with a defined are a of the surface that had faced outwards in vivo) were incubated in 0.5 ml of medium containing 0.1 M tris-HCl pH 8, 5 mM EDTA, 0.1% sodium azide and with or without aprotinin ($4 \times 10^{-6}$ mol/l) (Boehringer Mannheim, Germany) in 1.5 ml Eppendorf tubes at 370° C. for 5, 10 and 20 hours and then agitated for 10 sec on a Vortex mixer to release dissociated surface cells. The remaining tissue was removed and placed in fresh media for continued incubation. Tubes with released cells were centrifuged for 2 min at 5000 g to collect the cells. The cell pellets were washed once with 0.5 ml of phosphate buffered saline and then treated at 600° C. for 1.5 hours with 0.6 ml of 1 M sodium hydroxide. The alkali soluble protein was quantified according to Lowry et al., 1951, and taken as a measure of the amount of released cells. The results are shown in FIG. 2.

In a similar manner, the effect of various potential inhibitors (aprotinin, soybean trypsin inhibitor, pepstatin (Boehringer Mannheim, Germany) and iodoacetamide (Sigma, St. Louis, Mo.) was investigated. Single 2 mm tissue cylinders were prepared and incubated with medium with or without various potential inhibitors in concentrations as indicated in Table 1 below for 16 hours at 37° C., and released cells were quantified as described above. Note that EDTA (which is an inhibitor of metalloproteinases) was included in the incubation medium to give optimal cell release rates.

TABLE 1

Effect of protease inhibitors on cell release from *plantar stratum corneum* in vitro.
Mean and SD for five incubated tissue pieces.

| Inhibitor | Concentration (mol/l) | Inhibition (%) |
|---|---|---|
| None | — | 0 ± 8 |
| Aprotinin (Trasylol ®) | $1.5 \times 10^{-7}$ | 18 ± 8 |
| Aprotinin (Trasylol ®) | $4 \times 10^{-6}$ | 53 ± 13 |
| Aprotinin (Trasylol ®) | $1.5 \times 10^{-6}$ | 90 ± 5 |

TABLE 1-continued

Effect of protease inhibitors on cell release from *plantar stratum corneum* in vitro.
Mean and SD for five incubated tissue pieces.

| Inhibitor | Concentration (mol/l) | Inhibition (%) |
|---|---|---|
| Aprotinin (Trasylol ®) | $4 \times 10^{-6}$ | 98 ± 2 |
| Soybean trypsin inhibitor | $5 \times 10^{-6}$ | 81 ± 9 |
| Pepstatin | $1 \times 10^{-4}$ | 8 ± 4 |
| Iodoacetamide | $1 \times 10^{-3}$ | 6 ± 13 |

It was found that the serine proteinase inhibitors aprotinin and soybean trypsin inhibitor efficiently inhibited the cell shedding (FIG. 2 and Table 1 above). Since these two substances were inhibitory, but inhibitors of metalloproteinases (EDTA), thiol proteinases (iodoacetamide), and aspartic proteases (pepstatin) were not, it was concluded that a serine protease takes part in the process observed. It was also concluded that cell cohesion in the stratum corneum is dependent on protein structures and that a mechanism similar to that observed in vitro must be operating also during desquamation in vivo (Lundström and Egelrud 1988).

In further studies of the cell shedding in vitro from plantar stratum corneum it was found that the process could be separated into two separate steps. The first step takes place irrespective of whether or not EDTA is present in the incubation medium. The second step occurs only in the presence of EDTA. The first step could be inhibited by chymostatin and zinc ions, in addition to aprotinin. The second step could be inhibited by aprotinin and chymostatin. (Lundström and Egelrud 1990 a). Chymostatin is a low molecular weight inhibitor of proteinases with chymotrypsin-like substrate specificity. It has furthermore been found (Lundström and Egelrud 1990 a) that leupeptin, a low molecular weight inhibitor of proteinases with trypsin-like substrate specificity, had no effect on the in vitro cell shedding.

The protein structures most likely to be responsible for cell cohesion in the stratum corneum and thus possible candidates for being degraded in the desquamation-like cell shedding described above, are the desmosomes. A desmosome consists of two symmetrical halves which are located in contiguous cells. The two halves are connected in the extracellular space by transmembrane proteins called desmogleins.

1.3. Fate of desmoglein I (DG I) during cell shedding in vitro

The fate of desmoglein I (DG I) during cell shedding in vitro from plantar stratum corneum was studied. Plantar stratum corneum was incubated as described above in 1.1, and still cohesive tissue was separated from dissociated cells. Cells and tissue were extracted in a buffer containing 0.1 M Tris-HCl pH 9, 9 M urea, 2% sodium dodecylsulphate, 1% mercaptoethanol, 1 ml buffer per 20 mg of tissue, for 15 hours at 37° C. The extracts were prepared for polyacrylamide gel electrophoresis in 7.5% gels in the presence of sodium dodecyl sulphate (SDS-PAGE) according to Laemmli (Laemmli, 1970), followed by electrophoretic transfer (Towbin et al., 1979) to a nitrocellulose membrane (Bio-Rad, Richmond, Calif.) which was probed with a rabbit polyclonal antiserum prepared against DG I purified from bovine muzzles (Gorbsky et al. 1985). Bound antibodies were detected with alkaline phosphatase conjugated goat anti-rabbit immunoglobulins (Bio-Rad, Richmond, Calif.) (Blake et al. 1984).

Figures 3A, 3B:
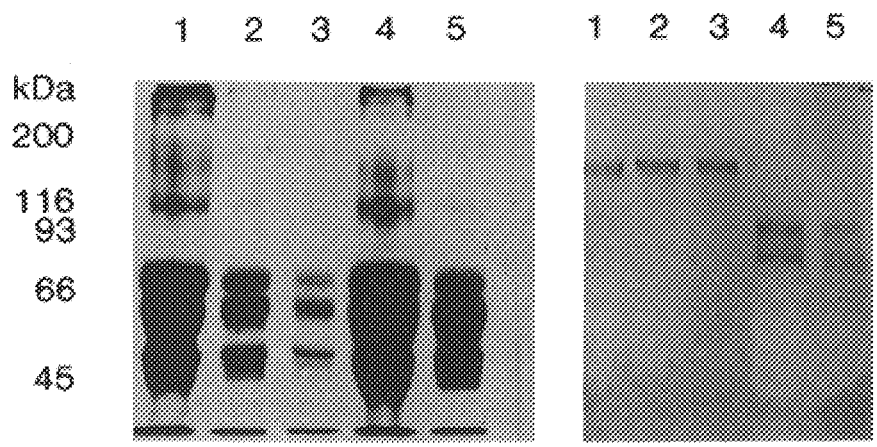

The results are shown in FIG. 3. The amounts of sample added to the immunoblot were adjusted to give approximately the same protein concentrations (as estimated by visual inspection of Coomassie blue stained SDS-PAGE gels) for coherent tissue and dissociated cells. Several dilutions of the extracts were run to make possible a semi-quantitative comparison of the amounts of the different anti-DG I reactive components in coherent stratum corneum and dissociated cells.

When still cohesive tissue and dissociated cells were extracted separately, it was found that whereas the still cohesive tissue contained only apparently intact DG I, dissociated surface cells contained only putative degradation products of this protein (FIG. 3).

Figure 5B:
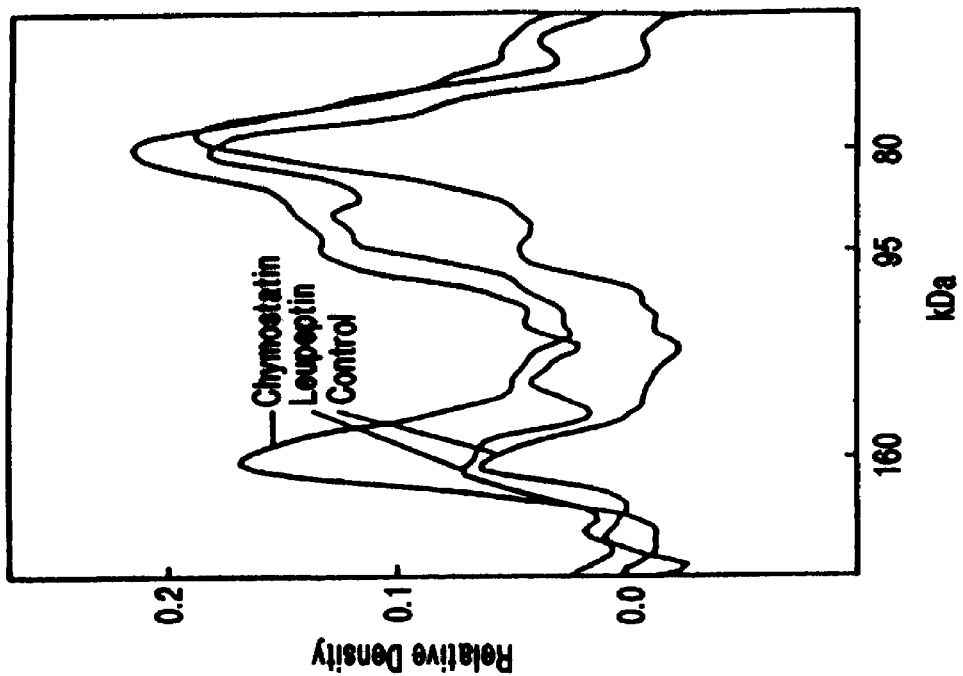
Figure 5A:
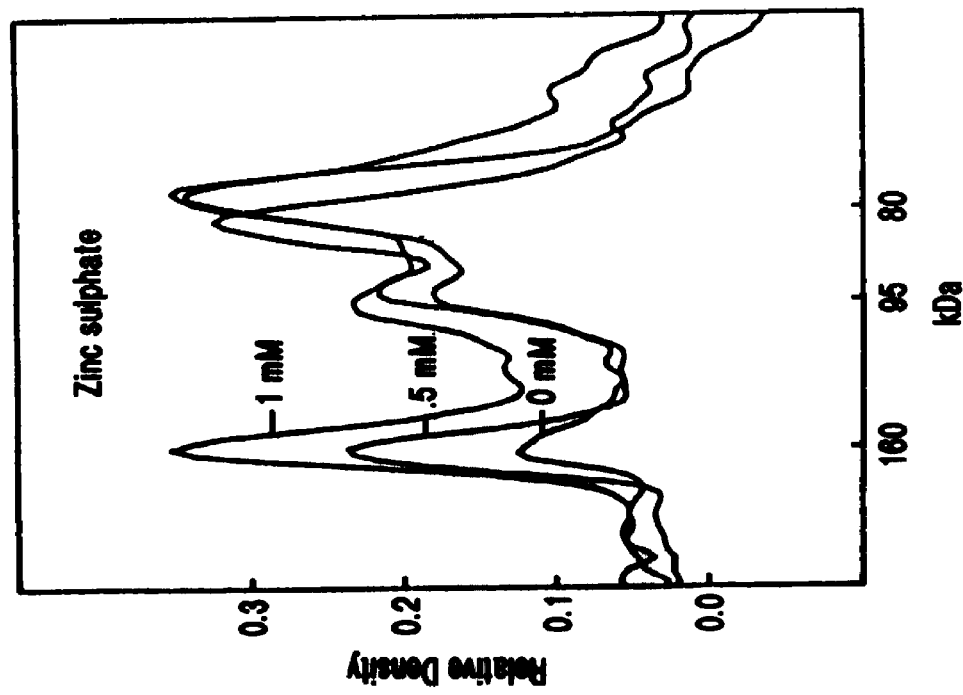

In FIG. 4 and 5 are shown the effects of aprotinin, zinc ions, chymostatin (Boehringer, Mannheim, Germany) and leupeptin (Boehringer, Mannheim, Germany) on the degradation of DG I during in vitro cell shedding from plantar stratum corneum.

First, the time course and the effect of aprotinin on the degradation of desmoglein I (DG I) in plantar stratum corneum undergoing cell shedding in vitro was investigated. Extracts of plantar stratum corneum were incubated as described above in 1.2 (but without separation of coherent tissue from dissociated cells before extraction) in the absence or presence of aprotinin (15 $\mu$M) and extracted after 0, 6, 12 or 24 hours. SDS-PAGE and immunoblotting was performed as described above. Densitometric scannings of the immunoblots were carried out in a Shimadzu CS-9000 flying spot scanner (Shimadzu, Kyoto, Japan) with reflected light at 560 nm in the zigzag mode. The results are shown in FIG. 4. Note the efficient inhibition by aprotinin on the degradation of DG I.

Then, the effect of zinc ion, chymostatin and leupeptin on the degradation of desmoglein I (DG I) in plantar stratum corneum during cell shedding in vitro was investigated. The experimental design was as outlined above. The incubations were carried out for 24 hours with zinc sulphate at concentrations 0, 1 or 5 mM, and with chymostatin or leupeptin at concentration 330 $\mu$M. The results showed inhibition of the transformation of the anti-DG I positive components from 160 kD to 95 and 80 kD by zinc ions and chymostatin, but not by leupeptin.

It is evident from these results that aprotinin, zinc ions, and chymostatin were inhibitory, whereas leupeptin was not. Thus the inhibitory profile for the degradation of DG I was the same as for the cell shedding from plantar stratum corneum in vitro (Lundström and Egelrud 1990 b).

It was considered important to demonstrate that mechanisms similar to those responsible for cell shedding from palmo-plantar stratum corneum are present also in the stratum corneum of skin from other body sites than palms and soles. Takahashi et al. (Takahashi et al. 1987) had reported that a mixture of the detergents N,N,-dimethyldodecylamine oxide (Sigma, St. Louis, Mo.) and sodium dodecylsulphate (Bio-Rad, Richmond, Calif.) in a molar ratio of 8:2 caused cell dissociation in non-palmoplantar stratum corneum prepared by trypsinization of whole epidermis. To avoid contamination by exogenous trypsin punch biopsies of normal human skin from the gluteal region were incubated at pH 8 with the abovementioned detergent mixture and EDTA (Egelrud and Lundström 1990). It was found that under these conditions the cornified layer dissociated to single cells. The addition of aprotinin to the incubation medium prevented this cell dissociation. It was concluded that also in non-palmo-plantar stratum corneum cell cohesion is dependent on protein structures, that desquamation in this tissue is dependent on proteolysis, and that the tissue contains a proteinase which can catalyze this proteolysis. Since the cell dissociation involved only the stratum corneum and not the deeper, non-cornified epidermal layers, it was concluded that the responsible proteinase resides in the deeper layers in an inactive or inhibited state.

Example 2

The discovery of stratum corneum chymotryptic enzyme (SCCE): a proteinase which fulfills criteria of being responsible for the degradation of intracellular cohesive structures in the stratum corneum in vitro and possibly also in vivo From the experiments presented in Example 1, it was concluded that the proteinase responsible for the unipolar surface cell dissociation in the in vitro model of desquamation in plantar stratum corneum should have the following properties:

1. It must be present in the stratum corneum.
2. It must be a serine proteinase.
3. It should have a chymotrypsin-like substrate specificity and an inhibitor profile similar to that observed for the in vitro cell shedding and for the associated degradation of desmoglein I.
4. It should have an extracellular localization in the stratum corneum.
5. It should have a pH-dependency allowing it to be active under physiological conditions, the pH of the stratum corneum being around 4.5–6.
6. Since the cell shedding from plantar stratum corneum in vitro proceeds continuously during prolonged incubation times even if the volume of the incubation medium is very large in comparison to the volume of the incubated tissue pieces, or if the incubation medium is repeatedly changed during the incubation, it seemed reasonable to assume that the responsible enzyme is bound to the tissue in a way that does not allow it to be extracted into the incubation medium during the incubation.

The following two experiments led to the discovery of SCCE (Egelrud and Lundström 1991):
2.1. Enzyme activity associated with the dissociated plantar corneocytes Dissociated plantar stratum corneum cells (corneocytes) were prepared by means of incubation of plantar stratum corneum as described in Example 1. The cells were filtered through a nylon net with mesh size 100 $\mu$m and then washed three times in ten volumes of 0.1 M Tris-HCl pH 8, 5 mM EDTA and three times in 0.1 M Tris-HCl pH 8. The cells were then incubated with two types of chromogenic proteinase substrates S-2288 or S-2586 (Kabi Diagnostica, Stockholm, Sweden): Ile-Pro-Arg-p-nitroanilide (S-2288) is split by a broad range of serine proteinases with arginine specificity (e.g. trypsin). Arg-Pro-Tyr-p-nitroanilide (S-2586) is a substrate for chymotrypsin-like proteinases.

In a total volume of 120 $\mu$l each reaction mixture contained 0.07 M Tris-HCl pH 8, 0.1% sodium azide, 1, 2.5, 5 or 10 $\mu$l of a 25% suspension of washed plantar corneocytes and 1.04 mM (S-2586) or 1.25 mM (S-2288) substrate. After incubation for 5 hours at 37° C. in microtiter plates the reaction was halted by the addition of 125 $\mu$l of 10% acetic acid. The cells were allowed to sediment and 200 $\mu$l of each supernatant transferred to new wells. Hydrolysis of the two substrates were followed by means of measuring the change in absorbance at 405 nm after the cells had been removed in a Behring Elisa Processor (Behringwerke, Marburg, Germany).

Figure 6:
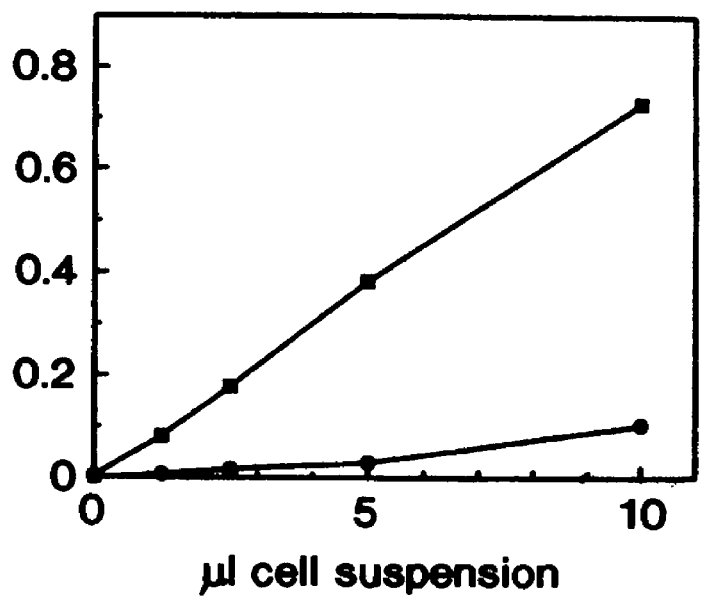

As shown in FIG. 6 there was an enzyme activity associated with the dissociated plantar corneocytes that catalyzed the hydrolysis of S-2586. In comparison the activity towards S-2288 was low.

Figure 7:
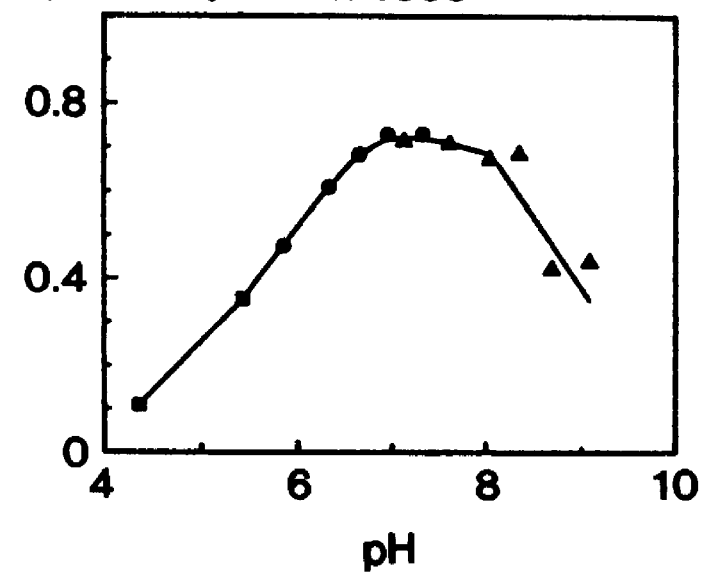

The pH-dependency of the S-2586 hydrolyzing activity was then investigated. The experimental design was as outlined above using 10 μl of a 25% suspension of washed plantar corneocytes and buffers with various pH (sodium acetate, sodium phosphate or Tris-HCl). Final buffer concentrations were 0.07 M. The results are shown in FIG. 7 from which it appears that the activity was optimal at pH 7–8, but significant also at pH 5.5.

In a further experiment, the effects of EDTA, metal ions and proteinase inhibitors on the hydrolysis of S-2586 at pH 8 by the proteinase associated with suspended plantar stratum corneum cells was investigated. The experimental design was as outlined above and in Table 2.

TABLE 2

Effects of EDTA, metal ions and proteinase inhibitors on the hydrolysis of S-2586 by the proteinase associated with *plantar stratum corneum* cells (enzyme source: suspended cells)

| Inhibitor | Concentration | Activity (%) (±SD, n = 3) |
|---|---|---|
| None | — | 100 |
| EDTA[a] | 4.2 mM | 109 ± 1 |
| PMSF[b] | 1 mM | 8 ± 3 |
| Aprotinin[a] | 3 μM | 10 ± 1 |
| Soybean trypsin inhibitor[a] | 0.16 μM | 6 ± 1 |
| Chymostatin[a,c] | 11 μM | 66 ± 9 |
|  | 55 μM | 32 ± 0 |
|  | 275 μM | 15 ± 3 |
| Leupeptin[a,c] | 325 μM | 93 ± 3 |
| ZnSO$_4$[a] | 100 μM | 10 ± 3 |
| HgCl$_2$[a] | 100 μM | 84 ± 2 |
| CuSO$_4$[a] | 100 μM | 85 ± 2 |

[a]Substance present in the assay mixture.
[b]A 25% suspension of *plantar stratum corneum* cells prepared as described in the text were preincubated for 1 hour at room temperature in the presence of 1 mM PMSF (Sigma, St. Louis, MO) dissolved in 2-propanol (final concentration of 2-propanol 4% v/v). Controls were preincubated with 4% 2-propanol only.
[c]Inhibitor dissolved in dimethyl sulphoxide (DMSO). All media, including controls, contained 5% (v/v) DMSO.

As shown in Table 2 above, phenylmethylsulphonyl fluoride (PMSF; a general inhibitor of serine proteinases), aprotinin, soybean trypsin inhibitor, chymostatin (a chymotrypsin inhibitor), and zinc ions, but not leupeptin (a trypsin inhibitor) inhibited the S-2586 hydrolyzing activity. The inhibitor profile was thus very similar to that observed for the in vitro cell shedding and the associated degradation of desmoglein I.

2.2. Zymography of dissociated plantar stratum corneum

It was found that the enzyme responsible for the S-2586 hydrolyzing activity discovered in 2.1 could be solubilized when the corneocytes were extracted with 1 M KCl in 0.1 M Tris-HCl pH 8. Therefore experiments with zymography were performed. For this reason KCl extracts of corneocytes were prepared for electrophoresis according to Laemmli (Laemmli 1970) but with no reducing agent in the sample buffer and with no heating of the samples. Samples were also prepared by means of extraction of dissociated plantar corneocytes with Laemmli's sample buffer without reducing agent at room temperature. For zymography a modification of the procedure of Horie et al. (Horie et al. 1984) was adopted. Polyacrylamide gel elctrophoresis in the presence of sodium dodecyl sulphate (SDS-PAGE) was carried out according to Laemmli in 12.5% gels with 1% co-polymerized heat-denatured casein. After electrophoresis the gels were soaked in a buffer containing 2% Triton X-100 for 1 hour at room temperature to remove SDS and then incubated at 37° C. for 15 hours. The gels were then stained with Coomassie blue. Separated caseinolytic enzymes showed up as clear bands against a blue background. See also legend to FIG. 8 for experimental details.

Figures 8A, 8B, 8C:
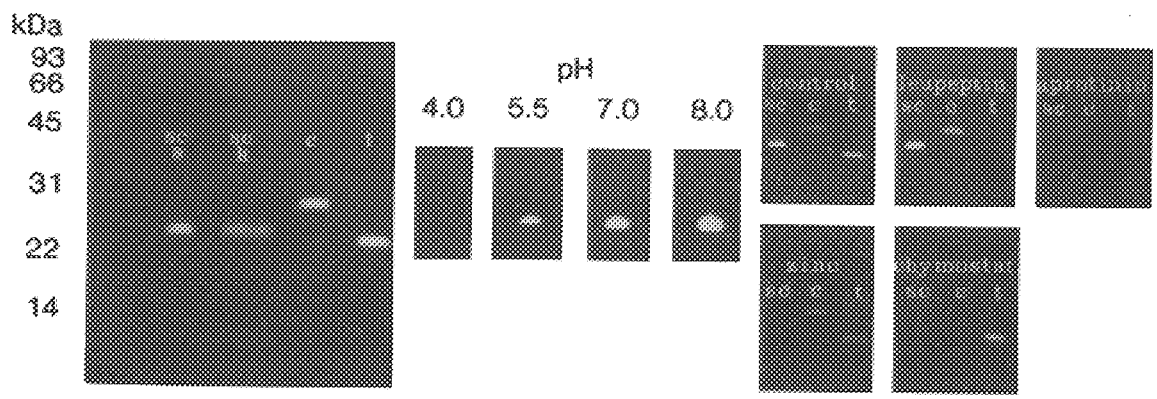

The results are shown in FIG. 8. The extracts of plantar corneocytes contained one major caseinolytic enzyme with apparent molecular weight around 25 kD. There were also minor caseinolytic enzymes with molecular weights around 30 kD. (These minor components are not clearly seen in the figure. It was later found that they could be inhibited by leupeptin but not by chymostatin). The 25 kD enzyme had significant acitivity at pH 5.5–8. It was inhibited by aprotinin, zinc ions, and chymostatin, but not by leupeptin. It thus had the same inhibitor profile as the S-2586 hydrolyzing activity described above. In experiments with gel exclusion chromatography (not shown) the 25 kD caseinolytic enzyme was found to co-chromatograph with the S-2586 hydrolyzing acitivity.

In further experiments (not shown) with the same technique as described above for 2.2 it was found that non-palmo-plantar stratum corneum contains an enzyme with properties apparently identical with the properties of the 25 kD proteinase associated with plantar corneocytes, from now on called stratum corneum chymotryptic enzyme (SCCE) (Lundström and Egelrud 1991).

It has also been possible to obtain evidence that SCCE is associated with plantar corneocytes in a way that allows it to be active in the stratum corneum extracellular space. This was done by first demonstrating that the dissociated corneocytes are impermeable for horseradish peroxidase (Mr 44 kD). It was then shown that human fibrinogen (Mr 340 kD) could be degraded by a suspension of corneocytes, and that this degradation could be inhibited by the same inhibitors as SCCE. It could be ruled out that the degradation of fibrinogen was due to solubilized enzyme (Egelrud 1992).

Example 3

Partial purification of stratum corneum chymotryptic enzyme (SCCE) and proteinase assays with chromogenic substrates 3.1. Preparation of KCl extracts of plantar corneocytes The production of dissociated plantar corneocytes as described in Example 1 was scaled up and KCl-extracts of washed plantar corneocytes containing SCCE as described in Example 2 were prepared.

The preparation of KCl extracts of plantar corneocytes is schematically outlined in Table 3 below. Hyperplastic human plantar stratum corneum was collected through a cooperation with the Society for Swedish Pedicyrists. Only material obtained by means of clippings or cuttings was used. Material was not collected from feet with scaling disorders. Before being mailed the stratum corneum was air dried and packeted in plastic bags. In the laboratory it was stored at −20° C. until used.

TABLE 3

Schematic outline of the preparation of SCCE-containing KCl-extracts of dissociated plantar corneocytes.

```
                    Plantar stratum corneum
                            50 g
                ┌──────────────────────────────┐
                │ Incubate at 37° C. for 24 hours│
                │ in 1000 ml of 0.1 M Tris-HCl pH 8,│
                │ 5 mM EDTA, 0.1% Na-azide     │
Supernatant ────│ Centrifuge 740 × g; 5 min.   │
                │                              │
                │ Wash pellet with 5 × 600 ml  │
Washings ───────│ of 0.1 M Tris-HCl pH 8.      │
                │ Centrifuge as above          │
                └──────────────────────────────┘
                ┌──────────────────────────────┐
                │ Extract pellet with 1 volume of│
                │ 2 M KCl in 0.1 M Tris-HCl pH 8│
                │ 30 min at 4° C.              │──── Extract 1
                │ Centrifuge as above          │    (about 250 ml)
                │                              │
                │ Wash pellet with 1 volume of │
                │ 1 M KCl in 0.1 M Tris-HCl pH 8│──── Extract 2
                │ Centrifuge as above          │    (about 150 ml)
Pellet ─────────┘
```

For each subsequent affinity chromatography step, extracts 1 and 2 from two preparations from 50 g each of plantar stratum corneum were pooled.

3.2. Proteinase assays with chromogenic substrates

A comparison of SCCE, bovine chymotrypsin, and human cathepsin G as regards effects of inhibitors aprotinin, chymostatin, zinc sulphate and substrate specificity was made.

Stock solution of MeO-Suc-Arg-Pro-Tyr-pNA (S-2586) was prepared in distilled water, of Suc-Ala-Ala-Pro-Phe-pNA (SEQ ID NO:15) (Boehringer, Mannheim, Germany) in 1-methyl-2-pyrrolidone (final concentration of solvent in incubation mixtures 4%) and of chymostatin in dimethyl sulphoxide (final concentra- tion of solvent in incubation mixtures 1%). Cathepsin G from purulent human sputum was obtained from E. Lotti, Geneva, Switzerland. The source of SCCE was KCl-extract of dissociated plantar corneocytes prepared as described above. The sources of the inhibitors aprotinin, chymostatin and zinc sulphate were as described above.

Incubations were performed at 37° C. in microtiter plates. The total incubation volume was 135 µl. Each incubation mixture contained Tris-HCl pH 8.0 (final concentration 0.08 M), KCl (final concentration 0.2 M), 100 µl substrate solution, 25 µl enzyme source (appropriately diluted in 0.1 M Tris-HCl pH 8.0, 1.0 M KCl) and 10 µl inhibitor solution.

In FIG. 9, A–C, MeO-Suc-Arg-Pro-Tyr-pNA (S-2586, initial concentration 1.2 mM) was used as substrate. In D the initial concentration of both substrates was 1.2 mM.

At the end of the incubations (1.5 hour) 125 µl of 10% acetic acid were added to each well and the absorbance read at 405 nm with incubation mixtures without added enzymes as blanks. The amounts of added enzymes were adjusted to give a change in absorbance at 405 nm at the end of the incubations of 0.3–0.7.

The results are summarized in FIG. 9, A–D. For the studies on the effects of inhibitors S-2586 was used as substrate. The efficiency of aprotinin as an inhibitor of SCCE and chymotrypsin was high and approximately the same for the two enzymes. The effect on cathepsin G, on the other hand, was much less (FIG. 9 A). Chymostatin caused inhibition of all three enzymes, but the inhibitor concentration that caused 50% inhibition was more than three orders of magnitude higher for SCCE than for chymotrypsin and cathepsin G (FIG. 9 B). Zinc sulphate was an efficient inhibitor of SCCE, but not of chymotrypsin and cathepsin G (FIG. 9 C). The activity of the three enzymes against the substrates MeO-Suc-Arg-Pro-Tyr-pNA (S-2586) and Suc-Ala-Ala-Pro-Phe-pNA (SEQ ID NO:11) are compared in FIG. 9 D. Since the object was to find similarities or differences between the enzymes examined, these experiments were carried out only at one initial concentration for each substrate. Whereas Suc-Ala-Ala-Pro-Phe-pNA (SEQ ID NO:11) appeared to be a significantly better substrate than S-2586 for chymotrypsin and cathepsin G, the reverse was found for SCCE.

Example 4

Purification N-terminal amino acid sequence determination of stratum corneum chymotryptic enzyme 4.1. Purification of SCCE from KCl-extracts of corneocytes by means of affinity chromatography on insolubilized soybean trypsin inhibitor (SBTI)

FIG. 10 shows the results of the affinity chromatography on SBTI. The affinity gel was prepared by linking 50 mg of SBTI (Boehringer, Mannheim, Germany) to 12 ml sedimented Affigel 15 (BioRad, Richmond, Calif.) according to the recommendations of the manufacturer. Remaining active groups on the gel were blocked with ethanolamine. Combined KCl-extracts from 100 g (dry weight) of plantar stratum corneum (total volume 700 ml) were run through a 0.8×2 cm bed of SBTI-Affigel 15 packed in a glass column, flow rate 42 ml/h, with continuous recording of the absorbance of the eluate at 280 nm. The column was washed with 0.1 M Tris-HCl pH 8, 1 M KCl, until the absorbance of the eluate was below 0.01, and then with 10 ml of 0.1 M Tris-HCl pH 8. Stepwise elution of bound material was carried out with HCl at 1, 10, and 100 mM. The eluant was changed when the absorbance of the eluate had decreased to below 0.01. 3 ml fractions were collected in test tubes which contained Tris-HCl pH 8, total volume 0.4 ml, in an amount calculated to be enough to adjust the pH of the eluate to above 7. The pH of each fraction was immediately checked and, if necessary, adjusted to about 7 with small volumes of 1 M Tris-HCl, pH 8. Analyses of peptide hydrolyzing activity with S-2586 (substrate for SCCE) and S-2288 (substrate for trypsin-like enzymes) were carried out as described in Example 2.1. The initial concentration of both substrates in the assay-mixtures was 1.1 mM. Approximately 90% of the S-2586 hydrolyzing activity was bound to the gel. Upon stepwise elution of the washed gel with 10–100 mM HCl approximately 60% of the total S-2586 hydrolyzing activity in the applied KCl-extract could be recovered. Of the total S-2288 hydrolyzing activity around 20% was bound to the affinity gel and 10% could be recovered in the eluate.

Figures 11A, 11B:
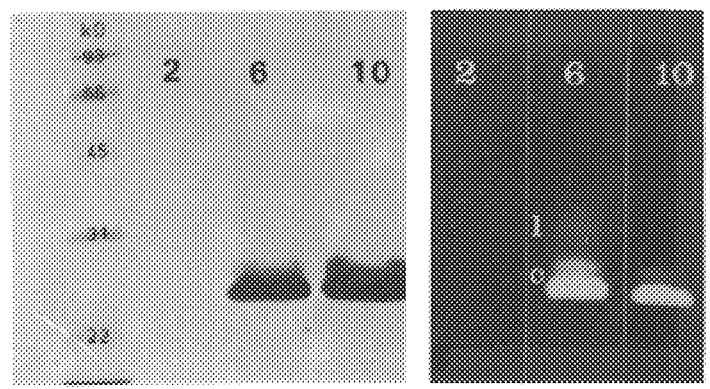

FIG. 11 shows analyses of the eluate from the SBTI-affinity chromatography with polyacrylamide gel electrophoresis in the presence of SDS (SDS-PAGE) and with zymography. Unreduced samples on 12.5% gels were run. See also Egelrud and Lundström 1991 and Example 2, 2.2 for experimental details. Before being prepared for electrophoresis the samples had been concentrated about 20-fold in A by means of centrifugal filtration with Ultrafree-MC-filters (cut off 10 kD; Millipore, Bedford, Mass.), and diluted 10-fold in B.

Figure 12:
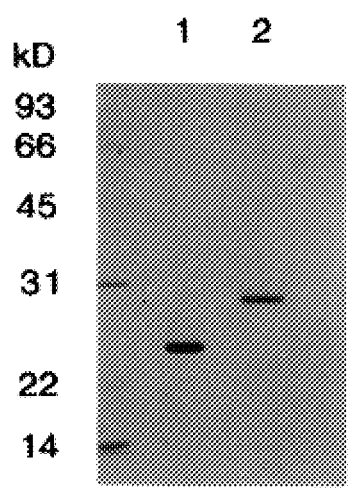

In FIG. 12 is shown a comparison by SDS-PAGE of an un-reduced and a reduced sample from the SBTI-affinity chromatography. As shown in FIGS. 10 and 11 the SBTI-affinity chromatography yielded a protein that was more than 90% pure (as judged from Coomassie blue-stained SDS-PAGE gels), with apparent molecular weight around 25 kD in un-reduced form and around 28 kD in reduced form. In addition there was a minor Coomassie blue-positive component with apparent molecular weight approximately 1 kD larger than the major component. On zymography gels there was one major and one minor band with the same electrophoretic mobilities as the two bands detected on Coomassie-blue stained gels with un-reduced samples. Both these caseinolytic components could be inhibited by chymostatin. In addition zymography showed minor components with apparent molecular weights around 30 kD, which could be inhibited by leupeptin. It was concluded that the major purified protein was SCCE.

4.2 Analysis of the N-terminal amino acid sequence of SCCE

Two hundred microliters of a fraction from a chromatogram with SBTI-Affigel 15, $A_{280nm}$ 0.2, were prepared for SDS-PAGE with or without reduction and run on a 12.5% polyacrylamide gel (thickness 1 mm, slot width 73 mm). After electrophoresis separated proteins were transferred electrophoretically to an Immobilon filter (Millipore) and stained with Coomassie blue according to Matsuidaira, 1987. The major protein band was cut out and processed in an Applied Biosystems 477A pulsed liquid-phase amino acid sequence analyser with an on-line PTH 120A analyzer (Applied Biosystems Inc., Foster City, Calif., USA). Sequencing was performed with regular cycle programs and chemicals from the manufacturer. Initial and repetitive yields, calculated from standard proteins, were 25% and 97% respectively.

The yields of amino acid derivatives were compatible with only one peptide being sequenced. With unreduced samples the yields were good in steps 1–6, but dropped to zero in steps 7 and 9. The yields in subsequent steps were markedly decreased. Also with reduced samples no amino acid derivatives could be detected in steps 7 and 9, but for subsequent steps where derivatives could be detected there were no steep drops in yields. These results suggest that there are cystines in positions 7 and 9. It was not possible, however, to detect carboxymethylated cystein in steps 7 and 9 after reduction and treatment with iodoacetic acid (100 mM). The sequence obtained (FIG. 13, SEQ ID NO:3) was identical for reduced and un-reduced samples.

Example 5

5.1. The preparation of SCCE-specific monoclonal antibodies

BALB/c mice (Bomholtgaard, Denmark) were given approximately 30 μg of native SCCE, purified as described in Example 4.1, in Freund's complete adjuvant (Difco Laboratories, Detroit, Mich.) as subcutaneous injections. The injections with the same amount of SCCE in Freund's incomplete adjuvant (Difco Laboratories, Detroit, Mich.) were repeated after one month. Four months after the first injection, one mouse was given intravenous booster injections on 3 consecutive days, 30 μg of antigen per injection. Hybridomas were produced by the method described in Carlsson et al., 1985, with cells of the SP2/0 myeloma cell line (ATCC CRL 1581). The identification of antibodies reacting with the purified SCCE-preparation was carried out with an ELISA technique. Culture supernatants from positive clones were further analysed by means of immunoblotting after SDS-PAGE. Clones producing antibodies reacting with SCCE in this test were propagated in mouse ascites fluid, and antibodies were purified by Protein A affinity chromatography and classified by the method described in Carlsson et al. 1985. Two useful antibodies were obtained, moab TE4b and moab TE9b, both of which were classified as $IgG_1$-kappa.

Figure 14A:
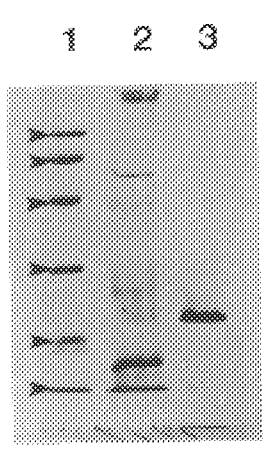
Figure 14B:
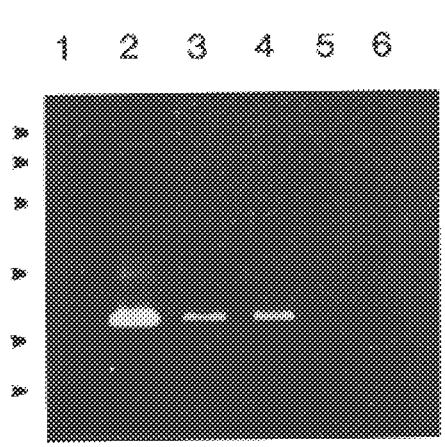
Figure 14C:
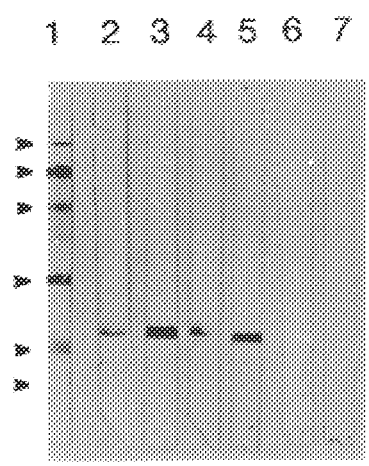

The characterization of moabs TE4b and TE9b by means of immunoprecipitation and immunoblotting is shown in FIG. 14. FIG. 14a (lane 2) shows a Coomassie-stained SDS-PAGE gel with a concentrated KCl-extract of dissociated plantar corneocytes, prepared as described in Example 3.1. The sample was dialyzed 4 hours against 0.1 M sodium acetate, pH 4, and concentrated approximately 100-fold by ultrafiltration before being prepared for electrophoresis. FIG. 14a (lane 3) shows a preparation of SCCE, purified as described in Example 4.1.

FIG. 14 b shows the results of an immunoprecipitation experiment where antibodies had been incubated with a KCl-extract of corneocytes, and then recovered with insolubilized Protein A. Resolubilized and dissociated antigen-antibody complexes were analyzed by zymography as described in Example 2.

250 μl of a KCl-extract of dissociated plantar corneocytes, which had been concentrated 5-fold by ultrafiltration, dialyzed against phosphate buffered saline, and to which bovine serum albumin (Sigma, St. Louis, Mo.) had been added to a final concentration of 10 mg per ml, were mixed with 10 μl of antibody solution or phosphate buffered saline and incubated 15 hours at 4° C. 25 μl of sedimented Protein A Sepharose (Pharmacia, Uppsala, Sweden) was then added to the tubes and the incubations continued with gentle shaking at room temperature for 2 hours. The gel was recovered by centrifugation and washed five times with 1 ml of 0.05% Tween 20 (Sigma, St. Louis, Mo.) in 0.05 M Tris-HCl, pH 7.5, 0.5 M NaCl. After the final wash the gel was extracted with 100 μl of Laemmli's sample buffer without reducing agent for 1 hour at room temperature. The extracts were cleared by centrifugation and applied on the gel.

Moabs TE4b and TE9b both precipitated a caseinolytic enzyme with the same Mr as purified SCCE and the corresponding major caseinolytic enzyme in the KCl-extract. The antibodies did not precipitate minor caseinolytic enzymes in the extract with Mr around 30 kDa, which have been shown to be inhibited by leupeptin, an inhibitor of trypsin-like serine proteinases. In addition to the 25 kDa caseinolytic enzyme the antibodies seemed to bind to a minor proteolytic component with Mr around 80 kDa. This component is usually present in KCl-extracts of plantar corneocytes prepared from tissue that has been dried prior to preparation, but is not found in preparations of fresh tissue (T. Egelrud, unpublished observation). It is not present in SCCE-preparations purified by affinity chromatography and may represent an aggregation product. It has not been possible to detect a corresponding component reacting with the antibodies on immunoblots.

On immunoblots of SDS-PAGE gels run under non-reducing conditions (FIG. 14c) moabs TE4b and TE9b reacted with a component present in KCl-extracts of plantar corneocytes (FIG. 14c lanes 2 and 4) and in the purified SCCE-preparation (FIG. 14c lanes 3 and 5), both of which had the same Mr as the major purified protein and the major caseinolytic component on zymograms. The antibodies were unreactive with samples that had been reduced in the presence of SDS, suggesting that they are directed against conformation-dependent epitopes.

In addition to the major protein with Mr around 25 kD in non-reduced form, the purified SCCE-preparation contains a minor Coomassie-positive component with Mr around 26 kD (non-reduced; see Example 3). On zymograms a corresponding caseinolytic component is present and can be inhibited by chymostatin in a way similar to the major 25 kD caseinolytic component (see Example 3). At higher concentrations of moabs TE4b and TE9b (results not shown) also this minor component could be seen to react with the antibodies on immunoblots. Similar results (not shown) have been obtained with a polyclonal rabbit antibody raised against the major Coomassie-positive component purified by preparative electrophoresis. The exact relationship between the two proteins with SCCE-like activity and apparent immunological cross-reaction is not known.

5.2. Polyclonal SCCE-specific antibodies 5.2.1. Chicken anti-SCCE

45 µg of SCCE, purified by SBTI-affinity chromatography as described in Example 4.1, in 0.2 ml of 0.1 M Tris-HCl was heat-denatured for 60 minutes at 60° C. and homogenized in an equal volumen of Freund's complete adjuvant (Difco Laboratories). The emulsion obtained was injected subcutaneously into Derco chicken, approximately 20 weeks old, from which a sample of blood for the preparation of pre-immune serum had been drawn. The chickens were given additional subcutaneous injections of emulsions prepared as described above but with Freund's incomplete adjuvant and with 30 µg of purified, heat-denatured SCCE (total volume of each emulsion 250 µl) after 3, 5 and 7 weeks. The chicken were bled 2 weeks after the last injection. The blood was immediately mixed with 2 volumes of Alsever's solution (per 100 ml: 100 ml 1.87 g of glucose, 0.8 g of sodium citrate, 0.62 g of sodium chloride, citric acid to pH 6.1) and centrifuged. The chicken anti-SCCE chosen for further studies was used in dilution 1/2000 in experiments with immunoblotting. See FIG. 17, Example 8 for an illustration of the specificity of the antiserum.

5.2.2. Rabbit anti-SCCE

SCCE purified by SBTI-affinity chromatography was subjected to SDS-PAGE without reduction as described in Example 4.1 on gels with a thickness of 15 mm according to Laemmli 1970. The major protein band previously shown to be SCCE was visualized with the copper chloride staining method according to Lee et al. 1987) and cut out. After removal of the copper chloride with EDTA according to Lee et al., the gel slices were homogenized in phosphate buffered saline. Samples of homogenized gel slices were suspended in equal volumes of Freund's adjuvant. Approximately 30 µg of pure SCCE prepared in this manner in complete adjuvant was given subcutaneously to a rabbit. After 3, 5 and 7 weeks, the injection was repeated with the same amount of SCCE, but with incomplete adjuvant. The rabbit was bled two weeks after the last injection.

The rabbit anti-SCCE obtained (D-5) was used in dilution 1/500–1/1000 in immunoblot experiments with alkaline phosphatase conjugated anti-rabbit immunoglobulins as second antibody.

In all immunoblotting experiments, bound second antibodies were detected according to Blake et al. 1984 (refers to Examples 5, 8 and 9).

The rabbit anti-SCCE Bo-1 was prepared in the same manner, but with SCCE that had been reduced prior to SDS-PAGE as antigen.

5.3. Immunohistochemical studies with the monoclonal antibodies

In immunohistochemical studies with SCCE-specific monoclonal antibodies, SCCE could be detected in high suprabasal cells of human keratinizing squamous epithelia (epidermis, inner root sheet of hair follicles, hard palate) but not in nonkeratinizing squamous epithelia (inner root sheet of hair follicle, lip and buccal mucosa). Thus SCCE may be specifically expressed in keratinizing squamous epithelia. Furthermore, SCCE was found to be expressed in high supra-basal cells of human epidermis reconstructed in vitro and grown at the air-water interface. When retinoic acid was added to the medium at a concentration that stimulated keratinocyte proliferation but inhibited the formation of a stratum corneum, SCCE was no longer expressed. This suggests that SCCE-expression may be part of the epidermal differentiation program.

Results from immunoelectrommicroscopical experimetns with SCCE-specific monoclonal antibodies are compatible with a role of SCCE in desmosomal degradation and thus in desquamation. The antibodies specifically labelled lamellar bodies undergoing secretion to the intercellular space between the uppermost granular cells and the lowermost stratum corneum cells, whereas in the stratum corneum the antibodies recognized epitopes in close association with desmosomes in the extracellular space.

Example 6

Cloning and sequencing of CDNA encoding human SCCE

Restriction enzymes were obtained from Promega, Madison, Mich., and TAQ-polymerase from Perkin-Elmer-Cetus, Norwalk, CT. A µgt11 human keratinocyte cDNA library prepared from MRNA derived from adult human keratinocytes of epidermal origin was obtained from Clontech Laboratories, Palo Alto, Calif. (Catalog # HL 1045 b). Initially, the library was screened with the anti-SCCE rabbit polyclonal sera D-5 and Bo-1 (see Example 5.2.2). Since Bo-1 polyclonal anti-SCCE serum gave high background signals, it was excluded from the extensive screening study at an early stage. Using the D-5 antiserum, a number of immunoreactive plaques were enriched as anticipated for true positive plaques. No reactivity with the monoclonal antibodies moAb 4 and moAb 9 was observed for any of the plaques. An extensive restriction enzyme characterization and PCR characterization of eleven isolated plaques revealed that no similarities between the various plaques could be detected. The presence of such partial similarities indicates that the plaques contain homologous DNA insert from the same cDNA sequence. Based on the failure to define a "fingerprint" of a probable SCCE cDNA sequence, the strategy was modified.

The plaques were screened in E. coli Y 1090 (Clontech) by plaque hybridization using a degenerated synthetic oligonucleotide as a probe. The oligonucleotide probe was designed based on the experimentally determined aminoterminal sequence of the native SCCE enzyme as described in Example 4.2. The most reliable part of the amino acid sequence, Ile-Ile-Asp-Gly-Ala-Pro (SEQ ID NO:3, aa 1–aa 6), was selected for construction of a synthetic 17-mer oligonucleotide probe 5'-ATHATHGAYGGNGCNCC-3' (H=A or C or T; Y=C or T; N=A or C or G or T), designated SYM3067, SEQ ID NO:4. The oligonucleotide probe was synthesized using a Beckman 200A DNA synthesizer using phosphoramidite technique according to the vendor's instructions.

E. coli Y 1090 bacteria were grown overnight in LB medium (Sambrook et al. 1989) containing 0.2% maltose and 10 mM $MgSO_4$. 0.4 ml of the culture was then mixed with diluted library phage stock and adsorbed for 20 minutes at 37° C. The infected culture was mixed with 6 ml soft agarose (0.75% agarose in LB and 10 mM $MgSO_4$). The soft agarose mixture was poured onto ten 150 mm LA plates. The plates were incubated at 37° C. for 5 hours, and placed at 40° C. overnight. In total, the plates contain approximately $4 \times 10^5$ plaques.

For immobilization of plaques each plate was overlaid with NEN DuPont Colony/Plaque Screen membranes (DuPont, Wilmington, Del.) for two minutes. The membranes were soaked for 2 times 2 minutes in 0.5 M NaOH, 2 times two minutes in Tris-HCl pH 7.5, and allowed to air dry. These membranes were then used in a hybridization experiment as described below. The membranes were pre-hybridized in 10% dextrane sulfate, 1 M NaCl, 1% SDS solution containing 100 mg/ml denatured herring sperm DNA (Sigma, St. Louis, Mo.) for 5 hours at 65° C. The probe, SYM 3067, was [$\mu$-$^{32}$P] DATP labelled using T4 polynucleotide kinase (Promega, Madison, Wis.) and added to the prehybridization mixture. Hybridization was carried out for 12–18 hours at 420° C.

After hybridization the membranes were washed for four times 5 minutes in 2xSSC at room temperature, two times 30 minutes in 2xSSC, 1% SDS at 42° C., and finally in 0.1 SSC at room temperature for 30 minutes. The membranes were autoradiographed on X-ray film (Hyperfilm-MP, Amersham, UK). Fourteen positive plaques were identified in the primary screening. These positive plaques were re-screened using the same probe and methods as described above. After the re-screening procedure two positive plaques were identified. The two selected plaques were purified for another time and the size of the inserts were determined by PCR using SYM 1600 and SYM 1601 as primers and isolated phages as templates. These two primers are complementary to $\mu$gt 11 phage left and right arms, respectively. The amplified DNA fragment of approximately 0.9 kb generated from phage A 6.2.2 was then digested with EcoRI and cloned into EcoRI digested pUC19 (Pharmacia, Uppsala, Sweden), pS496. This cloned fragment was subjected to a partial sequence analysis using sequence primers complementary to pUC19. The nucleotide sequence was determined using T7 sequencing kits (Pharmacia, Uppsala, Sweden or USB, Cleveland, Ohio).

Translation of the obtained DNA sequence resulted in an amino acid sequence which was homologous to the experimentally determined protein sequence. However, the sequence lacked a translational start codon. To isolate a full-length cDNA, the obtained DNA fragment was separated on agarose gel and used as a probe allowing hybridization under stringent conditions. This probe was $^{32}$P-labelled using multiprime DNA labelling system (Amersham, UK) by the following procedure. Water was added at a ratio of 3 ml per gram of gel, and placed in a boiling water bath for seven minutes to melt the gel and denature the DNA. The tube was then transferred to a water bath at 37° C. for at least 10 minutes. A volume of DNA/agarose solution containing approximately 25 ng of DNA was added to the labelling reaction, according to the supplier's instructions.

To obtain a full-length cDNA, the CDNA library was rescreened two times with this probe using the same methods as described above, except that the hybridization was under stringent conditions, at 65° C. These experiments resulted in the identification and isolation of 45 individual positive plaques which were initially screened by PCR analysis using SYM 1600 (5'-GTG GCG ACG ACT CCT GGA GCC-3'; SEQ ID NO:5) or SYM 1601 (5'-ACA CCA GAC CAA CTG GTA ATG-3'; SEQ ID NO:6) in combination with SYM 3208 as PCR primers for identification of a plaque containing the entire 5 'open reading frame. SYM 3208, 5'-TGGGTGGGAGCCTCTTGCACA-3', SEQ ID NO:7, which is at least partially complementary to the 5'part of SCCE cDNA, was designed based on the DNA sequence information achieved from pS496. After this screening four phages were selected for further analysis. For sequence analysis the resulting PCR amplified fragments derived from these phages were cloned into pUC19, as described above. The obtained results indicated that one of the phages, 205.2.1, contained a full-length insert.

DNA from phage isolate 205.2.1 was prepared according to Sambrook et al. 1989, and the DNA preparation was digested with EcoRI. The digested DNA was separated by agarose electrophoresis and a fragment of about 1 kb was isolated and cloned into EcoRI digested pUC19. The resulting plasmid was designated pS500 (FIG. 15). The complete nucleotide sequence of the cDNA fragment was determined as described above. As primers for sequencing reactions, specific oligonucleotides complementary to pUC19 or SCCE sequences were used. The nucleotide sequence (SEQ ID NO:1) contained an open reading frame sufficient to encode the entire amino acid sequence of an SCCE precursor protein consisting of 253 amino acids including a signal peptide and a prepolypeptide (SEQ ID NO:2).

Another phage called 106.1.2. was found to contain an SCCE cDNA sequence that lacks the 5'-untranslated sequence and the first three codons. This insert was isolated as a 954 bp EcoRI fragment and cloned into EcoRI linearized pUC19, resulting in plasmid pS498. This plasmid was partially sequenced.

A third phage designated 108.1.2 was found to contain an SCCE cDNA sequence that also lacks the 5'-untranslated sequence and seven nucleotides of the translated region. This cDNA insert has longer variant of the 3'-untranslated region, extending 1057 bp downstream of the stop codon. This 1884 bp EcoRI fragment was isolated and cloned into EcoRI linearized pUC19. The resulting plasmid was completely sequenced and designated pS501.

Example 7

Detection of SCCE mRNA in human epidermis
Preparation of total RNA from human epidermis This was carried out according to Chomczynski and Sacchi, 1987. Non-diseased human abdominal skin was obtained from plastic surgery. Immediately after removal it was chilled on ice. Within less than 15 minutes the epidermis was recovered by means of firm scraping with a scalpel, immersed in solution D (Chomczynski and Sacchi, 1987) and homogenized with a glass homogenizer. The protocol described by Chomczynski and Sacchi was then followed. Pelleted total RNA was stored at −20° C. in 70% ethanol until further analyzed.
Preparation of messenger RNA Five hundred micrograms of total epidermis RNA were processed with the Poly A Tract-kit (Promega) according to the instructions of the supplier.
RNA-eletrophoresis and blotting The agarose gels (1.4%) were prepared with 0.66 M formaldehyde in 1 x MOPS buffer and 0.6 g/ml ethidium bromide (Sigma, St. Louis, Mo.). mRNA corresponding to 100 $\mu$g of total RNA was dissolved in RNA-sample buffer (50% formamide, 2.2 M formaldehyde, 3% Ficoll, 1 x MOPS) and heated at 60° C. for 5 minutes before application. RNA-markers (BRL, Gaithersburg, Md.) were similarly treated. After the electrophoresis the gels were soaked in distilled water for 5 minutes followed by 50 mM NaOH for 30 minutes and 0.1 M Tris-HCl pH 7.5 for 30 minutes. Blotting to GeneScreen Plus membranes (NEN DuPont, Wilmington, Del.) was carried out with the Vacu-Gene equipment (Pharmacia, Uppsala, Sweden) for 1 hour in 10 x SSC. The membranes were then washed in 3 x SCC, dried overnight, and baked for 2 hours at 80° C. RNA was visualized on the membranes under UV-light.

cDNA-probes

The plasmid pS501, prepared as described in Example 6, was digested with HincII and BglII. This cDNA contains one HincII-site at bp No 1060 and one BglII site at bp No 1715. The 1070 bp fragment (HincII-site in pUC19 multiple cloning site—endogenous HincII-site) contains the SCCE encoding region except for 7 bp at the 5' end, and an untranslated region, including the polyadenylation site at bp 944–951, which is common to all SCCE-cDNAs that have been isolated. The 655 bp HincII-BglII fragment, which does not contain the poly A-tail, is unique for the SCCE cDNA 108-1-2. The fragments were purified by agarose electrophoresis and used for the preparation of $^{32}$PdCTP-labelled probes with the Multiprime DNA labelling kit (Amersham, Buckinghamshire, UK).

Hybridization

Membranes were boiled for 30 min in 1% SDS in 1x TE and prehybridized at 60° C. in 1% SDS, 1 M NaCl, 10% dextran sulphate, herring sperm DNA 0.1 mg/ml for 3 hours. Hybridization was carried out in the same solution at 60° C. overnight. Washings were carried out 2×30 min at 60° C. in 1% SDS in 2×SCC, and 3 hours in 0.1×SCC at room temperature. The membranes were then subjected to autoradiography.

Figure 16:
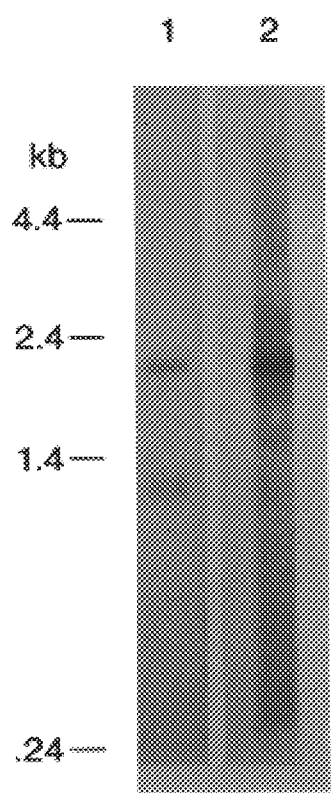

Results:

The presence in human epidermis of two mRNA-species with sizes around 1.2 kb and 2.0 kb respectively, could be demonstrated (FIG. 16). This is in good agreement with the evidences obtained from the cloning experiments where two types of cDNA were found.

Example 8

Expression of recombinant SCCE in *E. coli*

Construction of pGEX-2T/SCCE-plasmids

1. Sense PCR-primers 1.a CGTGGATCCATCGAAGGTCGTATTAT-TGATGGCGCCCCATGT (SYM 3367; SEQ ID NO:8, underlined 3'-part encoding the N-terminal amino acids IIDGAPC (SEQ ID NO:8) of active native SCCE, 5'-part with BamHI-site and an additional sequence encoding the factor Xa site IEGR.

1.b CGTGGATCCATCGAAGGTCGTTTG-GAAACTGCAGGAGAAGAA (SYM 3368; SEQ ID NO:9, underlined 3'-part corresponding to base pairs 76–96 in complete SCCE-cDNA-sequence encoding the amino acid sequence LETAGEE, (SEQ ID NO:9) 5'-part as in 1a.

2. Anti-sense PCR-primers.

TGATCCTCTGAGCTCTCCTG (SYM 3371; (SEQ ID NO:16) complementary to base pairs 285–304 in complete SCCE-cDNA-sequence, SEQ ID NO:1, with the SacI-site at bp 294).

A sequence of pS498 (Example 6) was PCR-amplified with the primers 1a/2 and 1b/2. The products obtained were purified by phenol extraction and ethanol precipitation, digested with BamHI/SacI, and purified by agarose electrophoresis. They were then cloned in TG2-cells into pGEX-2T (Pharmacia) digested with BamHI/EcoRI together with the 3' 673 base pairs of SCCE 106-1-2 obtained by digestion of pS498 with SacI and EcoRI. From bacterial clones used for expression studies plasmids (pS510 encoding native N-terminal next to factor Xa site, and pS511 encoding proposed propeptide next to factor Xa site) were isolated, and the nucleotide sequences corresponding to the inserts derived from PCR-products were checked by the dideoxy chain termination method using a T7 sequencing kit (Pharmacia, Uppsala, Sweden).

Expression studies

Overnight cultures of TG 2 cells with pS510 and pS511 in LB medium containing 50 μg/ml Carbenicillin (Sigma, St. Louis, Mo.) were diluted tenfold in fresh media and grown for 3 hours at 37° C. IPTG (Sigma, St. Louis, Mo.) was added to a final concentration of 0.1 mM and the cultures were grown at 37° C. for an additional 3 hours. Bacterial pellets were sonicated in PBS 1% Triton X-100 (Sigma, St. Louis, Mo.). After centrifugation at 10 000×g for 15 minutes, supernatants and pellets were analyzed by SDS-PAGE and immunoblotting with a polyclonal SCCE-specific chicken antiserum.

Figure 17A:
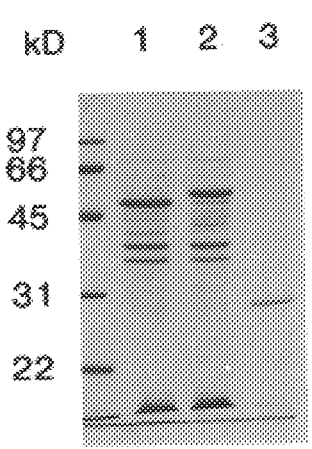
Figure 17B:
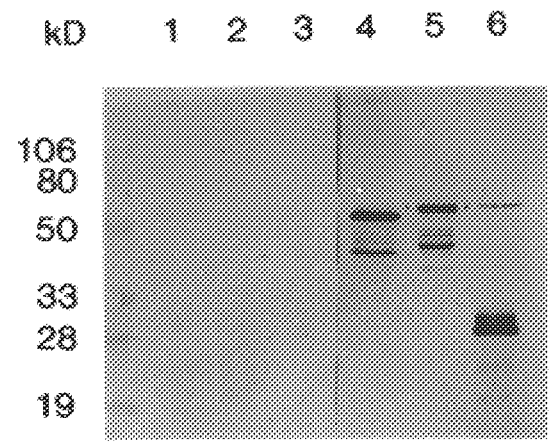

Large amounts of IPTG-inducable proteins with Mr approximately 50 kD (pS510) and 52 kD (pS511) with SCCE-like immuno-reactivity were found in the pellets insoluble in PBS-Triton X-100 (see FIG. 17).

The supernatants after sonication in PBS-Triton X-100 contained GST/SCCE fusion proteins with the same size as in the insoluble pellets, but the amounts were low in comparison to the insoluble pellets.

These results show that it is possible to express SCCE as a fusion protein with GST and sequences corresponding to specific protease cleavage site in the pre-pro-SCCE amino acid sequence will make it possible to repeat this experiment with the intention to produce recombinant SCCE in bacteria. The produced protein can be solubilized in urea or guanidinium hydrochloride and then purified by cationic ion exchange chromatography due to the high isoelectric point of SCCE. The purified protein can be renatured by dialysis against buffers with lower concentration of denaturating agent and then cleaved with Factor Xa to release the GST polypeptide from SCCE or pro-SCCE. The GST/SCCE fusion proteins will also be used as immunogens for the production of SCCE-specific antibodies, and as immunosorbents in antibody purification.

Example 9

Expression of recombinant human SCCE in mammalian cells

In order to generate an expression vector for production of recombinant SCCE human cDNA sequences were isolated from the plasmid pS500 as a 897 bp EcoRI/DraI fragment. mhis fragment was subcloned into EcoRI and SmaI digested pUC19, resulting in pS502. The plasmid pS502 was then digested with EcoRI and SalI to isolate SCCE cDNA sequences as a 0.9 kb fragment, which was again subcloned into a pUC19 variant lacking HindIII site, resulting in plasmid pS503. This pUC19 variant was generated by digestion of pUC19 with HindIII, fill-in using Klenow enzyme and religation. In order to facilitate cloning into an expression vector, a HindIII site was introduced in the 5'end of SCCE cDNA. This was done by digestion of pS503 with EcoRI and insertion of a linker which converts the site to HindIII, SYM3603 5'-AATTGTGGAAGCTTCCAC-3', SEQ ID NO:10. The resulting plasmid which harbors the protein encoding part of the SCCE cDNA with a HindIII site at the 5'end and a SalI site at the 3'end, respectively, was designated pS505.

The final expression vector was obtained by ligation of three different DNA fragments. First, pS505 was digested with HindIII and SalI, and a 0.9 kb fragment was isolated.

Second, to provide the distal part of the murine metallothioneine upstream regulatory element, the bovine papilloma-virus sequences, the rabbit beta-globin genomic fragment providing mRNA processing signals and the plasmid sequences, pML2d, to allow selection and replication in

*E. coli* (Waldenström et al. 1992), the vector pS147 was digested with SacI and SalI and a fragment of about 12 kb was isolated.

Third, to isolate the proximal part of the murine metallothioneine promoter the plasmid pS42, in which the native BglII positioned in the leader sequence has been converted to a HindIII site, was digested with SacI and HindIII and an approximately 220 bp fragment was isolated.

The ligation of these three fragments resulted in the SCCE expression vector pS507 (see FIG. 18)

The expression vector pS507 was co-transfected with a vector containing the neomycin resistance gene driven by the Harvey sarcomavirus 5' long terminal repeat and with SV40 polyadenylation signals (Lusky and Botchan, 1984) into murine C127 cells (ATCC CRL 1616). Transfection experiments were carried out according to the calcium-phosphate precipitation method (Graham and Van der Eb, 1973). Cells were cultured in Ham's F12/Dulbecco's modified Eagle's medium (DMEM; Gibco BRL, Gaithersburg, Md.) (1:1) supplemented with 10% fetal calf serum (HyClone, Logan, Utah). Neomycin resistant cell clones were selected with 1.5 mg/ml of G418 (Gibco-BRL), and after 10–15 days of selection resistant cell clones were identified and isolated from the master plates and passaged for subsequent analysis.

To analyze the expression of recombinant SCCE genes total RNA was prepared from the isolated cell lines. Total RNA was prepared from C127 cells and separated on a 1% formaldehydeagarose gel, transferred to nitrocellulose membrane and hybridized to a $^{32}$P-labelled SCCE probe. The probe was the 1070 bp HincII fragment of the SCCE cDNA isolated by HincII digestion of pS500, and agarose electrophoresis. Experimental procedures were according to Ausubel et al., 1992. Northern blot experiments and hybridization with $^{32}$P-labelled SCCE cDNA showed that recombinant SCCE mRNA was detectable in several cell lines harboring the SCCE vector, pS507. No hybridization was found in control samples derived from from C127 cell lines containing an identical vector except for SCCE cDNA (FIG. 19). The size 1.4 kB corresponds to the expected size.

Figure 20:

Samples of conditioned cell culture medium were harvested and analyzed by immunoblotting. SDS-PAGE was performed according to Laemmli (1970) and for the immunoblotting, chicken antinative SCCE was used as detecting antibody. An alkaline phosphatase labelled anti-chicken IgG (Sigma, St. Louis, Mo.) was used for enzyme labelling. The results are shown in FIG. 20.

To analyze the expression of recombinant SCCE, total RNA was prepared from C127 cells transfected with the expression vector pS507. As control samples, total RNA was prepared from both non-transfected C127 cells and from C127 cells transfected with expression vector pS147. The vector pS147 is similar to pS507 except that it contains the cDNA for human bile salt-stimulated lipase (Nilsson et al., 1990) instead for the human SCCE cDNA. RNA was prepared according to Ausubel et al. (1992). Northern blot experiments and hybridization with $^{32}$P-labelled SCCE cDNA showed that recombinant SCCE mRNA of about 1.4 kb was detectable in C127 cells harbouring the SCCE vector, pS507 (FIG. 19). No hybridization was found in control samples derived from C127 cell lines containing pS147 or non-transfected C127 cells. The length of the recombinant SCCE mRNA is as expected.

Samples of conditioned cell culture medium were harvested and analyzed by SDS-PAGE and immunoblotting. The blot was developed as described in Blake et al. 1984.

The obtained results (see FIG. 20) show that C127 cells harbouring pS507 are producing three proteins which show reaction with all available polyclonal rabbit and chicken SCCE antibodies as well as with the anti-SCCE monoclonals prepared as described in Example 5. The recombinant SCCE reactive proteins show an apparent molecular weight that is about 1 kDa larger than purified native human SCCE. The recombinant protein does not show any proteolytic activity. By comparison of the deduced SCCE amino acid sequence with the experimentally determined NH-2 terminus of native human SCCE and with sequences of other chymotrypsin-like proteases, it can be concluded that the recombinant SCCE produced in C127 cells is in its pro-enzyme form. Sequence data indicate that this pro-enzyme can be activated by proteolytic cleavage at the C-terminal side of the lysine in the sequence . . . AQGDKIIDGAP. . . , (SEQ ID NO:17) the underlined sequence is the NH-2 sequence of active native human SCCE (SEQ ID NO:2, aa −5 to aa 6).

Example 10

Purification and characterization of recombinant SCCE

Figure 21A:
Figure 21B:
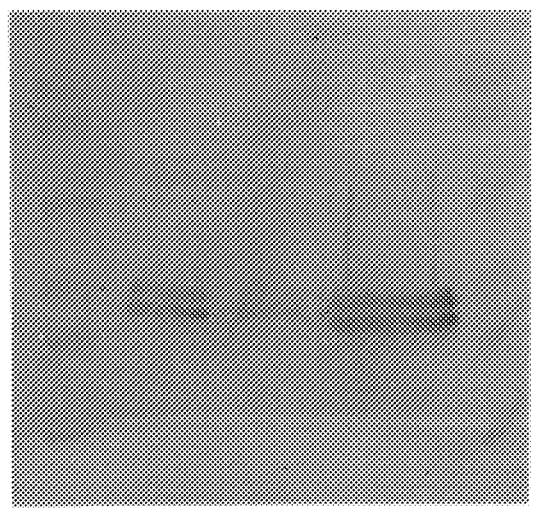

Purification 1.3 mg of the monoclonal antibody TE4b directed against native SCCE was coupled to 1.5 ml of CNBr-activated Sepharose (Pharmacia-LKB Biotech., Uppsala, Sweden) using the method described by the manufacturer. 40 ml of medium containing SCCE was filtered through a 0.45 μm filter and then applied to the column. The column was washed several times with 10 mm sodium phosphate, 150 mM NaCl, pH 7.2, and then eluted with 0.1 M glycine-HCl, pH 2.5. Eluted protein was immediately neutralized by adding 0.1 volume of 1 M Tris-HCl, pH 8.0. The results of the purification are seen in FIG. 21.

Activation

Figure 22:
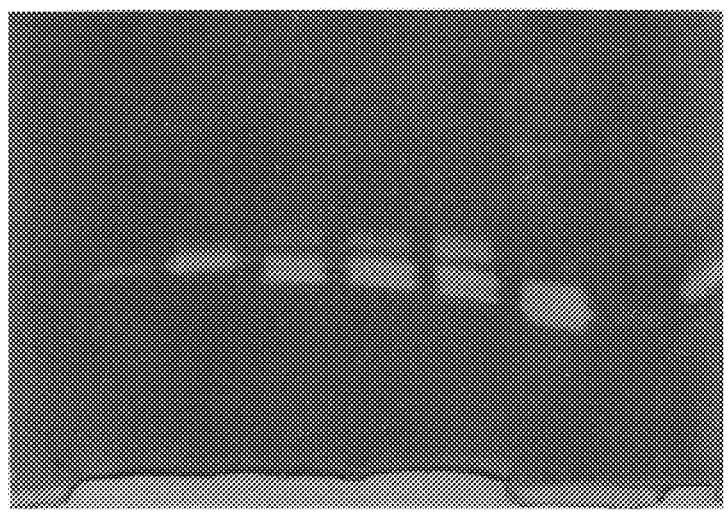

Recombinant SCCE (4.6 μg in 200 μl), purified using the gel with the monoclonal antibody coupled (see above) was digested with 4.6 μl of 0.1 mg/ml trypsin (mass ratio 10:1) at 37° C. Samples (50 μl) were withdrawn at 20 minutes, 1 hour, 3 hours and 20 hours, and 5 μl of 10 μM (4-amidinophenyl)methane-sulfonyl (APMSF; Boehringer Mannheim, Germany) was added to terminate the reaction. Activity of cleaved SCCE was assayed by non-reducing SDS-PAGE on casein gels as described in Example 2.2. Identity of the obtained cleaved forms of SCCE was assayed by reducing SDS-PAGE followed by immunoblotting using chicken anti-native SCCE followed by an alkaline phosphatase labelled anti-chicken IgG and nitro blue tetrazolium and 5-bromo-4-chloro-3-indolyl phosphate as substrate for alkaline phosphatase. The results are seen in FIG. 22.

N-terminal sequencing

Affinity purified (as described above) SCCE, approximately 35 μg, was slot-blotted using a Bio-Dot SF unit (Bio-Rad, Richmond, Calif.) onto an Immobilon• membrane (Millipore, Bedford, Md.). The membrane was then washed several times with distilled water to remove all Tris and glycine. The part of the membrane where the protein was bound was cut out and sequenced using an Applied Biosystems (Foster City, Calif.) 477A Pulsed Liquid Phase sequencer with an on-line PTH 120A Analyzer. Sequencing was performed with regular cycle programmes and chemicals from the manufacturer. The sequence obtained in the first six positions was glu-glu-ala-gln-gly-asp corresponding to amino acids −7-−2 of SEQ ID NO:2. As can be concluded from this result, the signal peptide consists of 22 amino acids and based on the N-terminal amino acid sequence of native active SCCE, the propeptide consists of seven amino acids.

Deglycosylation

Figure 23:
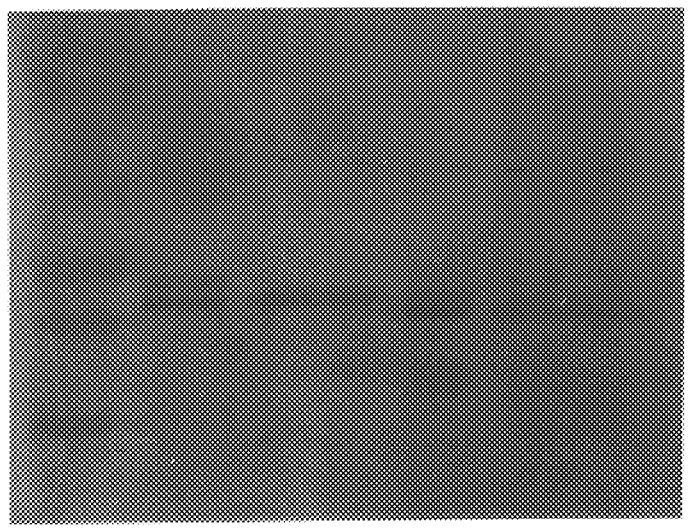

Purified recombinant SCCE (5 μg) and native SCCE (20 μg) were boiled for 3 minutes in 20 μl of 0.5% SDS and 0.1 M β-mercaptoethanol. The samples were diluted with sodium phosphate buffer, pH 8.6, and Nonidet P-40 to final concentrations of 0.2 M and 1.25%, respectively. N-Glycosidase F® (Boehringer Mannheim) was added (for recombinant protein 0.6 units and for native protein 1.2 units of enzyme) and the reaction mixture was incubated overnight at 37° C. The final concentration of SDS in the sample assay was 0.17%. N-Glycosidase F® treated SCCE was analyzed on 8–18% SDS-PAGE followed by immunoblotting as described above. The obtained results showed reduction in apparent molecular weight of the two upper bands while the apparent molecular weight of the lowest band was unchanged (FIG. 23). This shows that recombinant SCCE produced in C127 cells exists in two N-glycosylated forms and one non-glycosylated form. This result is analogous with what can be seen with active native SCCE (FIG. 23).

Example 11

Compositions comprising SCCE

The compositions may be prepared according to conventional pharmaceutical techniques including mixing the active compounds thoroughly with the other ingredients. All percentages are by weight.

Compositions which comprise more than one active compound are also within the scope of the invention. The following examples may thus be construed as also including more than one active substance. In a similar manner, the term "SCCE" may be replaced by "pro-SCCE". Compositions which comprise SCCE as well as pro-SCCE are thus also within the scope of the invention.

SCCE=native or recombinant stratum corneum chymotryptic enzyme, optionally in combination with other active compounds q.s.=quantum satis

| Cream o/w | % |
|---|---|
| SCCE | 0.01–20 |
| Polysorbate 80 | 0.5 |
| Emulsifying wax | 5 |
| Mineral oil | 4 |
| Dimethicone | 1 |
| Glyceryl stearate | 6 |
| Antioxidant | q.s. |
| EDTA | 0.1 |
| Preservative | q.s. |
| Glycerin 85% | 4 |
| Propylene glycol | 7 |
| pH regulating agent | 0.01–10 |
| Water | 65–76 |

Examples of variable factors: Antioxidants, chelating agents, preservatives, emulsifying systems (the proportion between the oily phase and the aqueous phase and the content of emulsifying agents and other relevant excipients).

| Cream w/o | % |
|---|---|
| SCCE | 0.01–20 |
| Cetyl alcohol | 0.5 |
| Lanolin | 5 |
| White petrolatum | 10 |
| Mineral oil | 45 |
| Antioxidant | q.s. |
| EDTA | 1 |
| pH regulating agent | 0.01–10 |
| Preservative | q.s. |
| Water | 15–25 |

Examples of variable factors: Antioxidants, chelating agents, preservatives, emulsifying systems (the proportion between the oily phase and the aqueous phase and the content of emulsifying agents and other relevant excipients).

| Ointment | % |
|---|---|
| SCCE | 0,01–20 |
| Lanolin | 15 |
| Petrolatum | 58–68 |
| Mineral oil | 15 |
| Dimeticone | 2 |
| Antioxidant | q.s. |

Examples of variable factors: antioxidants.

| Liniment | % |
|---|---|
| SCCE | 0.01–20 |
| Emulsifylng wax | 4 |
| Glyceryl stearate | 3 |
| Mineral oil | 15 |
| Polysorbate 80 | 0.6 |
| Glycerin 85% | 3 |
| Propylene glycol | 5 |
| Antioxidant | q.s. |
| EDTA | 0.1 |
| Preservative | q.s. |
| Water | 59–69 |

Examples of variable factors: Antioxidants, chelating agents, preservatives, emulsifying systems (the proportion between the oily phase and the aqueous phase and the content of emulsifying agents and other relevant excipients).

| Gel | % |
|---|---|
| SCCE | 0.01–20 |
| Triethanolamine | 1–5 |
| Ethyl alcohol | 10 |
| Cetyl alcohol | 10 |
| Cellulose gum | 5 |
| EDTA | 0.1 |
| Preservative | q.s. |
| Water | 59–74 |

Examples of variable factors: Gel forming agents, antioxidants, chelating agents, preservatives.

| Solution, Water | % |
|---|---|
| SCCE | 0.01–20 |
| pH regulating agent | 0.01–10 |
| Cetyl alcohol | 4 |
| Propylene glycol | 5 |
| Preservative | q.s. |
| Antioxidant | q.s. |

| Solution, Water | % |
| --- | --- |
| EDTA | 0.1 |
| Water | 37–89 |

Examples of variable factors: Antioxidants, chelating agents, preservatives, refattening agents, humectants.

| Solution, ethyl alcohol | % |
| --- | --- |
| SCCE | 0.01–20 |
| pH regulating agent | 0.01–10 |
| Propylene glycol | 5 |
| Cetyl alcohol | 3 |
| Antioxidant | q.s. |
| EDTA | 0.1 |
| Ethyl alcohol | 50–95 |

Examples of variable factors: Antioxidants, chelating agents, humectants.

| Suspension | % |
| --- | --- |
| SCCE | 0.01–20 |
| Carbomer | 0.5 |
| Cellulose gum | 0.5 |
| Polysorbate 80 | 0.1 |
| Propylene glycol | 5 |
| Ascorbic acid | 0.05 |
| Cetyl alcohol | 4 |
| Polysorbate | q.s. |
| EDTA | 0.1 |
| pH regulating agent | 0.01–10 |
| Water | 72–80 |

Examples of variable factors: Antioxidants, chelating agents, preservatives, suspending agents.

| Paste | % |
| --- | --- |
| SCCE | 0.01–20 |
| Petrolatum | 45–55 |
| Zinc oxide | 40 |
| Mineral oil | 5 |
| Antioxidant | q.s. |

Examples of variable factors: Antioxidants, paste bases.

| Stick | % |
| --- | --- |
| SCCE | 0.01–20 |
| Cutina LM | 70–80 |
| Myristyl alcohol | 5 |
| Castor oil | 2 |
| Beeswax, white | 10 |
| Petrolatum, white | 3 |
| Antioxidant | q.s. |

Examples of variable factors: Antioxidants, stick-bases.

| Spray - manual | % |
| --- | --- |
| SCCE | 0.01–20 |
| pH regulating agent | 0.01–10 |
| Ethyl alcohol | 30 |
| Glycerine 85% | 5 |
| Prolylene glycol | 5 |

| Spray - manual | % |
| --- | --- |
| Cetyl alcohol | 3 |
| Antioxidant | q.s. |
| EDTA | 0.1 |
| Preservative | q.s. |
| Water | 22–57 |

Examples of variable factors: Antioxidants, chelating agents, preservatives, refattening agents, humectants.

| Spray aerosol solution | % |
| --- | --- |
| SCCE | 0.01–20 |
| pH regulating agent | 0.01–10 |
| Isopropyl myristate | 3 |
| Propylene glycol | 5 |
| Ethyl alcohol | 48–92 |
| Propellant | q.s. |

Examples of variable factors: Refattening agents, humectants.

| Spray - aerosol foam | % |
| --- | --- |
| SCCE | 0.01–20 |
| Wax | 3 |
| Ethyl alcohol | 50–55 |
| Antioxidant | q.s. |
| EDTA | 0.1 |
| Water | 20–35 |
| Propellant | q.s. |

Examples of variable factors: Propellants, antioxidants, chelating agents.

| Spray aerosol emulsion | % |
| --- | --- |
| SCCE | 0.01–20 |
| Cellulose derivatives | 1–3 |
| Tween ® 60 | 1.0 |
| Glyceryl stearate | 2.5 |
| Potassium sorbate | 0.2 |
| Antioxidant | q.s. |
| EDTA | 0.1 |
| Preservative | q.s. |
| pH regulating agent | 0.01–10 |
| Water | 50–95 |
| Propellent | q.s. |

Examples of variable factors: Antioxidants, chelating agents, preservatives, emulsifying systems (the proportion between the oily phase and the aqueous phase and the content of emulsifying agents and other relevant excipients).

| Shampoo | % |
| --- | --- |
| SCCE | 0.01–20 |
| Sodium lauryl sulphate | 40 |
| Cetyl alcohol | 3 |
| Foaming agent or conditioner | 3 |
| Sodium chloride | 2 |
| Antioxidant | q.s. |
| EDTA | 0.1 |
| Preservative | q.s. |
| Water | 43–53 |

Examples of variable factors; Shampoo bases, antioxidants, chelating agents, preservatives, humectants, conditioners.

| Body Shampoo | % |
|---|---|
| SCCE | 0.01–20 |
| Sodium lauryl sulphate | 40 |
| Cetyl alcohol | 4 |
| Foaming agent or conditioner | 3 |
| Pearling agent | 10 |
| Preservative | q.s. |
| Antioxidant | q.s. |
| EDTA | 0.1 |
| Water | 40–50 |

Examples of variable factors: Shampoo bases, antioxidants, chelating agents, preservatives, additives, conditioners.

| Medicated Soap | % |
|---|---|
| SCCE | 0.01–20 |
| 1-Hydroxyethane-1,1-diphophoric acid | 0.2 |
| Glycerin | 0.8 |
| Sodium soap of coconut oil and tallow | 88–98 |
| Additives | 0.7 |

Examples of variable factors: Humectants, soap-bases.

| Powder | % |
|---|---|
| SCCE | 0.01–20 |
| Talc | 65–70 |
| Kaolin | 6 |
| Titanium dioxide | 2 |
| Calcium carbonate | 8 |
| Magnesium stearate | 3 |
| Corn or oat starch | 5–10 |

Examples of variable factors: Powder-bases, preservatives, mass ratios.

| Hair conditioner | % |
|---|---|
| SCCE | 0.01–20 |
| Cetyl alcohol | 2.2 |
| Alkyltrimethylammoniumchloride | 1.25 |
| Octyldodecanol | 1 |
| Citric acid | 1 |
| EDTA | 0.1 |
| Preservative | q.s. |
| Antioxidant | q.s. |
| Water | ad 100 |

Examples of variable factors: Conditioners, preservatives, chelating agents, antioxidants.

In a similar manner, topical compositions comprising a compound which is capable of inhibit or enhance the activity of SCCE can be prepared.

Example 12

Desmosome digestion activity of recombinant SCCE

Corneocytes containing intact desmosomes were removed from skin by tape stripping to the deeper layers of stratum corneum, and the squames were detached with hexane and dried down in aliquots. Corneocytes aliquots (3 mg) were extracted with 1 M sodium chloride at 4° C. to solubilise intrinsic proteases and then washed extensively with incubation buffer (0.1 M Tris/HCl pH 8.0) to remove endogenous proteolytic activity from the preparations. Incubations were performed in 0.1 M Tris pH 8.0 with or without 10 µg of recombinant SCCE for 24 hours at 37° C. Evidence of desmosomal digestion by the enzyme was demonstrated by measuring the levels of the desmosome marker protein desmoglein I (DG I). This was isolated from the squames by extraction in an 8 M urea/2%SDS/β-mercaptoethanol buffer with the subsequent purification of the DG I glycoprotein using concanavalin A affinity chromatography. The concanavalin A eluate was fractionated by SDS-PAGE and electrophoretically transferred to a PDVF membrane for immunoblotting. DG I was identified using a specific antiserum and detected using enhanced chemiluminescence. The results are shown in Table 4.

TABLE 4

|  | Control | + rSCCE, 10 µg |
|---|---|---|
| DG I (arbitrary units/mg squames) | 7950 ± 4992 | 4059 ± 2360 |

The results presented in Table 4 show that recombinant SCCE is able to degrade intracellular cohesive structures in the stratum corneum in an in vitro assay.

Example 13

Effects of inhibitors on the activity of recombinant SCCE

The effect of the inhibitors aprotinin, chymostatin and zinc sulphate on the S-2586 hydrolysing activity of rSCCE was investigated. The experimental design was as outlined in Example 3.2. The results are shown in Table 5.

TABLE 5

| Inhibitor | Concentration (µM) | Activity (%) |
|---|---|---|
| Aprotinin | 0 | 100 |
|  | 0.35 | 51.6 |
|  | 1.4 | 21.2 |
|  | 5.7 | 7.4 |
| Chymostatin | 0 | 100 |
|  | 0.64 | 74.9 |
|  | 2.56 | 33 |
|  | 41 | 1.9 |
| ZnSO$_4$ | 0 | 100 |
|  | 15.6 | 50.7 |
|  | 62.5 | 19.4 |
|  | 250 | 5.1 |

As shown in Table 5 above, aprotinin, chymostatin and zinc ions inhibited the S-2586 hydrolysing activity of recombinant SCCE in a similar manner as for the native enzyme.

REFERENCES

Ausubel et al. (1992). Current protocols in Molecular Biology. John Wiley & Sons
Blake et al. (1984). Anal Biochem 136: 175–179
Carlsson et al. (1985). Molec Immun 22: 1073–1080
Caughey et al. (1991). J Biol Chem 266: 12956–12963
Chomczynski and Sacchi (1987). Anal Biochem 162: 156–159
Egelrud and Lundström (1990). J Invest Dermatol 95: 456–459
Egelrud and Lundström (1991). Arch Derm Res 283: 108–112
Egelrud (1992). Eur J Dermatol 2: 50–55
Gorbsky et al. (1985). Proc Natl Acad Sci USA 82: 810–814

Graham and Van der Eb (1973). Virology 52: 456–467
Hogan, B., Constantini, F. and Lacy, E. (1986). Manipulating the Mouse Embryo. A Laboratory Manual. Cold Spring Harbor Press
Horie et al. (1984). Comp Biochem Physiol 77B: 349–354
Laemmli (1970). Nature 227: 680–685
Lee et al. (1987). Anal Biochem 166: 308–312
Lowry et al. (1951). J Biol Chem 193: 265–275
Lundström and Egelrud (1988). J Invest Dermatol 91: 340–343
Lundström and Egelrud (1990 a). Arch Derm Res 282: 234–237
Lundström and Egelrud (1990 b). J Invest Dermatol 94: 216–220
Lundström and Egelrud (1991). Acta Derm Venereol (Stockh) 71: 471–474
Lusky and Botchan (1984). Cell 36: 391–401
Matsudaira P (1987). J Biol Chem 262: 10035–10038
Mizutani et al. (1991). J Clin Invest 87: 1066–1071
Nilsson et al. (1990) Eur J Biochem 192: 543–550
Norris (1990). J Invest Dermatol 95: 371
Salvesen et al. (1987). Biochemistry 26: 2289–2293
Sambrook et al. (1989). Molecular Cloning, A Laboratory Manual. 2nd ed. Cold Spring Harbor
Schechter et al. (1983). J Biol Chem 258: 2973–2978
Schechter et al. (1989). J Biol Chem 264: 21308–21315
Schwartz et al. (1987). J Immunol 138: 2611–2615
Takahashi et al (1987). J Soc Cosmet Chem 38: 21–28
Toulta et al. (1989). BBRC 158: 569–575
Towbin et al. (1979). Proc Natl Acad Sci USA 76: 4350–4354
Waldenström et al. (1992) Gene 120: 175–181
Wintroub et al. (1986). J Clin Invest 77: 196–201
WO 93/04172 (filed by Symbicom Aktiebolag on 19 Aug. 1992)

---

|---|---|---|---|---|---|---|---|---|---|---|

We claim:

1. An isolated nucleic acid having a nucleotide sequence encoding a polypeptide comprising a human stratum corneum chymotryptic enzyme, or a proteolytically active fragment thereof, wherein said nucleotide sequence hybridizes under stringent conditions with the nucleic acid sequence set forth in SEQ ID NO: 1.

2. A nucleic acid according to claim 1 encoding a polypeptide having a subsequence of the amino acid sequence shown in SEQ ID NO: 2.

3. A nucleic acid according to claim 1 having a nucleotide sequence encoding a polypeptide having an amino acid sequence selected from the group consisting of the amino acid sequence of SEQ ID NO; 2 from position 1 through position 224, inclusive; the amino acid sequence of SEQ ID NO: 2 from position −7 through position 224, inclusive, and the amino acid sequence of SEQ ID NO: 2 from position −29 through position 224, inclusive.

4. A nucleic acid according to claim 1 having the nucleotide sequence set forth in SEQ ID NO: 1.

5. An expression system comprising a replicable expression vector which carries and is capable of mediating the expression of a nucleic acid as defined in any one of claims 2 and 1–3.

6. A replicable expression vector, designated pS507 and deposited on 11 May 1993 with the collection of Deutsche Sammlung von Mikroorganismen und Zelikulturen GmbH (DSM) under the accession number DSM 8282 in accordance with the provisions of the Budapest Treaty.

7. A plasmid, designated pS$^{500}$ and deposited on 11 May 1993 with the collection of Deutsche Sammlung von Mikroorganismen und Zellkulturen GmbH (DSM) under the accession number DSM 8281 in accordance with the provisions of the Budapest Treaty.

8. A transformed cell comprising an expression system according to claim 5 wherein the cell is selected from the group consisting of a bacterium, a yeast cell, a protozoan cell, a fungal cell, an insect cell, a plant cell, and a mammalian cell.

9. A transformed cell line comprising an expression system according to claim 5 wherein the cell line is a mammalian cell line.

10. A method of producing a polypeptide comprising a human stratum corneum chymotryptic enzyme, or a proteolytically active fragment thereof, comprising the following steps:

(a) preparing a vector comprising a nucleic acid comprising a nucleotide sequence as defined in any one of claims 2 and 1–3, (b) transforming a suitable host cell or mammalian cell line with the vector of step (a), (c) culturing the host cell or mammalian cell line of step (b) under conditions suitable for the expression of the encoded polypeptide, (d) isolating said polypeptide from the host cell or mammalian cell line of step (c) or from the culture medium of said host cell or mammalian cell line, and, (e) optionally, subjecting said polypeptide to post-translational modification.

11. A method of producing a substantially pure polypeptide having either an amino acid sequence from position −7 through position 224 of SEQ ID NO:2, inclusive, or an amino acid sequence from position 1 through position 224 of SEQ ID NO:2, inclusive, comprising the following steps:

(a) preparing a vector comprising a nucleic acid comprising a nucleotide sequence as defined in any one of claims 2 and 1–3, (b) transforming a suitable host cell or mammalian cell line with the vector of step (a), (c) culturing the host cell or mammalian cell line of step (b) under conditions suitable for the expression of the encoded polypeptide, (d) isolating said polypeptide from the host cell or mammalian cell line of step (c) or from the culture medium of said host cell or mammalian cell line, and, (e) optionally, subjecting said polypeptide to post-translational modification.

12. A method according to claim 10 or claim 11 wherein the polypeptide produced is isolated by a process comprising one or more procedures selected from the group consisting of immunoprecipitation with antibodies raised to a native or recombinantly-produced human stratum corneum chymotryptic enzyme, affinity chromatography with antibodies raised to a native or recombinantly-produced human stratum corneum chymotryptic enzyme, affinity chromatography with a ligand specific for a native human stratum corneum chymotryptic enzyme, chromatography based on relative molecular mass, chromatography based on relative molecular charge, high performance liquid chromatography, electrophoretic separation procedures, and specific solubilization techniques.

* * * * *

UNITED STATES PATENT AND TRADEMARK OFFICE
CERTIFICATE OF CORRECTION

PATENT NO. : 5,834,290
DATED : November 10, 1998
INVENTOR(S) : Egelrud et al.

It is certified that error appears in the above-identified patent and that said Letters Patent is hereby corrected as shown below:

Claim 3, col. 64, line 57, delete "SEQ ID NO," and insert therefor -- SEQ ID NO: --.

Claim 3, col. 64, line 59, delete "inclusive," and insert therefor -- inclusive; --.

Claim 5, col. 64, line 67, delete "2 and 1-3" and insert therefor -- 1-4 --.

Claim 6, col. 65, line 3, delete "Zelikulturen" and insert therefor -- Zellkulturen --.

Claim 7, col. 65, line 6, delete "pS$^{500}$" and insert therefor -- pS500 --.

Claim 10, col. 65, line 25, delete "claims 2 and 1-3" and insert therefor -- claims 1-4 --.

Claim 11, col. 66, line 8, delete "claims 2 and 1-3" and insert therefor -- claims 1-4 --.

Signed and Sealed this

Thirteenth Day of July, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO: 1:

( i ) SEQUENCE CHARACTERISTICS:
( A ) LENGTH: 986 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
( A ) ORGANISM: Homo sapiens ( i x ) FEATURE:
( A ) NAME/KEY: CDS
( B ) LOCATION: 25..786

( i x ) FEATURE:
( A ) NAME/KEY: sig_peptide
( B ) LOCATION: 25..90

( i x ) FEATURE:
( A ) NAME/KEY: mat_peptide
( B ) LOCATION: 112..783

( x i ) SEQUENCE DESCRIPTION: SEQ ID NO: 1:

```
GAATTCGCG GATTTCCGGG CTCC ATG GCA AGA TCC CTT CTC CTG CCC CTG           51
                          Met Ala Arg Ser Leu Leu Leu Pro Leu
                          -29             -25

CAG ATC CTA CTG CTA TCC TTA GCC TTG GAA ACT GCA GGA GAA GAA GCC         99
Gln Ile Leu Leu Leu Ser Leu Ala Leu Glu Thr Ala Gly Glu Glu Ala
-20              -15              Glu -10                      -5

CAG GGT GAC AAG ATT ATT GAT GGC GCC CCA TGT GCA AGA GGC TCC CAC         147
Gln Gly Asp Lys Ile Ile Asp Gly Ala Pro Cys Ala Arg Gly Ser His
                1                 5                     10

CCA TGG CAG GTG GCC CTG CTC AGT GGC AAT CAG CTC CAC TGC GGA GGC         195
Pro Trp Gln Val Ala Leu Leu Ser Gly Asn Gln Leu His Cys Gly Gly
        15                      20                  25

GTC CTG GTC AAT GAG CGC TGG GTG CTC ACT GCC GCC CAC TGC AAG ATG         243
```

| | | | | | | | | | | | | | | | |
|---|---|---|---|---|---|---|---|---|---|---|---|---|---|---|---|
| Val | Leu | Val | Asn | Glu | Arg | Trp | Val | Leu | Thr | Ala | Ala | His | Cys | Lys | Met |
| | | 30 | | | | 35 | | | | | 40 | | | | |

| AAT | GAG | TAC | ACC | GTG | CAC | CTG | GGC | AGT | GAT | ACG | CTG | GGC | GAC | AGG | AGA | 291 |
|---|---|---|---|---|---|---|---|---|---|---|---|---|---|---|---|---|
| Asn | Glu | Tyr | Thr | Val | His | Leu | Gly | Ser | Asp | Thr | Leu | Gly | Asp | Arg | Arg | |
| 45 | | | | | 50 | | | | | 55 | | | | | 60 | |

| GCT | CAG | AGG | ATC | AAG | GCC | TCG | AAG | TCA | TTC | CGC | CAC | CCC | GGC | TAC | TCC | 339 |
|---|---|---|---|---|---|---|---|---|---|---|---|---|---|---|---|---|
| Ala | Gln | Arg | Ile | Lys | Ala | Ser | Lys | Ser | Phe | Arg | His | Pro | Gly | Tyr | Ser | |
| | | | | 65 | | | | | 70 | | | | | 75 | | |

| ACA | CAG | ACC | CAT | GTT | AAT | GAC | CTC | ATG | CTC | GTG | AAG | CTC | AAT | AGC | CAG | 387 |
|---|---|---|---|---|---|---|---|---|---|---|---|---|---|---|---|---|
| Thr | Gln | Thr | His | Val | Asn | Asp | Leu | Met | Leu | Val | Lys | Leu | Asn | Ser | Gln | |
| | | | 80 | | | | | 85 | | | | | 90 | | | |

| GCC | AGG | CTG | TCA | TCC | ATG | GTG | AAG | AAA | GTC | AGG | CTG | CCC | TCC | CGC | TGC | 435 |
|---|---|---|---|---|---|---|---|---|---|---|---|---|---|---|---|---|
| Ala | Arg | Leu | Ser | Ser | Met | Val | Lys | Lys | Val | Arg | Leu | Pro | Ser | Arg | Cys | |
| | | 95 | | | | | 100 | | | | | 105 | | | | |

| GAA | CCC | CCT | GGA | ACC | ACC | TGT | ACT | GTC | TCC | GGC | TGG | GGC | ACT | ACC | ACG | 483 |
|---|---|---|---|---|---|---|---|---|---|---|---|---|---|---|---|---|
| Glu | Pro | Pro | Gly | Thr | Thr | Cys | Thr | Val | Ser | Gly | Trp | Gly | Thr | Thr | Thr | |
| | 110 | | | | | 115 | | | | | 120 | | | | | |

| AGC | CCA | GAT | GTG | ACC | TTT | CCC | TCT | GAC | CTC | ATG | TGC | GTG | GAT | GTC | AAG | 531 |
|---|---|---|---|---|---|---|---|---|---|---|---|---|---|---|---|---|
| Ser | Pro | Asp | Val | Thr | Phe | Pro | Ser | Asp | Leu | Met | Cys | Val | Asp | Val | Lys | |
| 125 | | | | | 130 | | | | | 135 | | | | | 140 | |

| CTC | ATC | TCC | CCC | CAG | GAC | TGC | ACG | AAG | GTT | TAC | AAG | GAC | TTA | CTG | GAA | 579 |
|---|---|---|---|---|---|---|---|---|---|---|---|---|---|---|---|---|
| Leu | Ile | Ser | Pro | Gln | Asp | Cys | Thr | Lys | Val | Tyr | Lys | Asp | Leu | Leu | Glu | |
| | | | | 145 | | | | | 150 | | | | | 155 | | |

| AAT | TCC | ATG | CTG | TGC | GCT | GGC | ATC | CCC | GAC | TCC | AAG | AAA | AAC | GCC | TGC | 627 |
|---|---|---|---|---|---|---|---|---|---|---|---|---|---|---|---|---|
| Asn | Ser | Met | Leu | Cys | Ala | Gly | Ile | Pro | Asp | Ser | Lys | Lys | Asn | Ala | Cys | |
| | | | 160 | | | | | 165 | | | | | 170 | | | |

| AAT | GGT | GAC | TCA | GGG | GGA | CCG | TTG | GTG | TGC | AGA | GGT | ACC | CTG | CAA | GGT | 675 |
|---|---|---|---|---|---|---|---|---|---|---|---|---|---|---|---|---|
| Asn | Gly | Asp | Ser | Gly | Gly | Pro | Leu | Val | Cys | Arg | Gly | Thr | Leu | Gln | Gly | |
| | | 175 | | | | | 180 | | | | | 185 | | | | |

| CTG | GTG | TCC | TGG | GGA | ACT | TTC | CCT | TGC | GGC | CAA | CCC | AAT | GAC | CCA | GGA | 723 |
|---|---|---|---|---|---|---|---|---|---|---|---|---|---|---|---|---|
| Leu | Val | Ser | Trp | Gly | Thr | Phe | Pro | Cys | Gly | Gln | Pro | Asn | Asp | Pro | Gly | |
| | 190 | | | | | 195 | | | | | 200 | | | | | |

| GTC | TAC | ACT | CAA | GTG | TGC | AAG | TTC | ACC | AAG | TGG | ATA | AAT | GAC | ACC | ATG | 771 |
|---|---|---|---|---|---|---|---|---|---|---|---|---|---|---|---|---|
| Val | Tyr | Thr | Gln | Val | Cys | Lys | Phe | Thr | Lys | Trp | Ile | Asn | Asp | Thr | Met | |
| 205 | | | | | 210 | | | | | 215 | | | | | 220 | |

| AAA | AAG | CAT | CGC | TAACGCCACA | CTGAGTTAAT | TAACTGTGTG | CTTCCAACAG | 823 |
|---|---|---|---|---|---|---|---|---|
| Lys | Lys | His | Arg | | | | | |
| | | | 225 | | | | | |

AAAATGCACA GGAGTGAGGA CGCCGATGAC CTATGAAGTC AAATTTGACT TTACCTTTCC 883

TCAAAGATAT ATTTAAACCT CATGCCCTGT TGATAAACCA ATCAAATTGG TAAAGACCTA 943

AAACCAAAAC AAATAAAGAA ACACAAAACC CTCAACGGAA TTC 986

( 2 ) INFORMATION FOR SEQ ID NO: 2:

( i ) SEQUENCE CHARACTERISTICS:
        ( A ) LENGTH: 253 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| Met | Ala | Arg | Ser | Leu | Leu | Leu | Pro | Leu | Gln | Ile | Leu | Leu | Leu | Ser | Leu |
|---|---|---|---|---|---|---|---|---|---|---|---|---|---|---|---|
| -29 | | | | -25 | | | | | -20 | | | | | -15 | |

| Ala | Leu | Glu | Thr | Ala | Gly | Glu | Glu | Ala | Gln | Gly | Asp | Lys | Ile | Ile | Asp |
|---|---|---|---|---|---|---|---|---|---|---|---|---|---|---|---|
| | | | -10 | | | | | -5 | | | | | | 1 | |

| Gly | Ala | Pro | Cys | Ala | Arg | Gly | Ser | His | Pro | Trp | Gln | Val | Ala | Leu | Leu |
|---|---|---|---|---|---|---|---|---|---|---|---|---|---|---|---|
| | | 5 | | | | | 10 | | | | | 15 | | | |

| Ser | Gly | Asn | Gln | Leu | His | Cys | Gly | Gly | Val | Leu | Val | Asn | Glu | Arg | Trp |
|---|---|---|---|---|---|---|---|---|---|---|---|---|---|---|---|
| 20 | | | | | 25 | | | | | 30 | | | | | 35 |

| Val | Leu | Thr | Ala | Ala | His | Cys | Lys | Met | Asn | Glu | Tyr | Thr | Val | His | Leu |
|||||40||||45|||||50||

| Gly | Ser | Asp | Thr | Leu | Gly | Asp | Arg | Arg | Ala | Gln | Arg | Ile | Lys | Ala | Ser |
||||55|||||60||||65|||

| Lys | Ser | Phe | Arg | His | Pro | Gly | Tyr | Ser | Thr | Gln | Thr | His | Val | Asn | Asp |
|||70|||||75|||||80|||

| Leu | Met | Leu | Val | Lys | Leu | Asn | Ser | Gln | Ala | Arg | Leu | Ser | Ser | Met | Val |
||85|||||90|||||95||||

| Lys | Lys | Val | Arg | Leu | Pro | Ser | Arg | Cys | Glu | Pro | Pro | Gly | Thr | Thr | Cys |
|100||||105|||||110|||||115|

| Thr | Val | Ser | Gly | Trp | Gly | Thr | Thr | Thr | Ser | Pro | Asp | Val | Thr | Phe | Pro |
|||||120||||125|||||130||

| Ser | Asp | Leu | Met | Cys | Val | Asp | Val | Lys | Leu | Ile | Ser | Pro | Gln | Asp | Cys |
||||135||||140||||145|||

| Thr | Lys | Val | Tyr | Lys | Asp | Leu | Leu | Glu | Asn | Ser | Met | Leu | Cys | Ala | Gly |
|||150||||155|||||160||||

| Ile | Pro | Asp | Ser | Lys | Lys | Asn | Ala | Cys | Asn | Gly | Asp | Ser | Gly | Gly | Pro |
||165||||170||||175|||||

| Leu | Val | Cys | Arg | Gly | Thr | Leu | Gln | Gly | Leu | Val | Ser | Trp | Gly | Thr | Phe |
|180||||185|||||190|||||195|

| Pro | Cys | Gly | Gln | Pro | Asn | Asp | Pro | Gly | Val | Tyr | Thr | Gln | Val | Cys | Lys |
|||||200||||205|||||210|

| Phe | Thr | Lys | Trp | Ile | Asn | Asp | Thr | Met | Lys | Lys | His | Arg | | | |
||||215||||220|||||||

( 2 ) INFORMATION FOR SEQ ID NO: 3:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Homo sapiens ( x i ) SEQUENCE DESCRIPTION: SEQ ID NO: 3:

| Ile | Ile | Asp | Gly | Ala | Pro | Cys | Ala | Cys | Gly | Ser | Xaa | Pro | Xaa | Gln | Val |
|1||||5||||10|||||15||

| Ala | Leu | Leu | Ser | Gly | Asn | Gln | Leu |
||||20|||||

( 2 ) INFORMATION FOR SEQ ID NO: 4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 4:

ATHATHGAYG GNGCNCC                                                            17

( 2 ) INFORMATION FOR SEQ ID NO: 5:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 5:

GTGGCGACGA CTCCTGGAGC C          21

( 2 ) INFORMATION FOR SEQ ID NO: 6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 6:

ACACCAGACC AACTGGTAAT G          21

( 2 ) INFORMATION FOR SEQ ID NO: 7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 7:

TGGGTGGGAG CCTCTTGCAC A          21

( 2 ) INFORMATION FOR SEQ ID NO: 8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 8:

CGTGGATCCA TCGAAGGTCG T ATT ATT GAT GGC GCC CCA TGT    42
                                 Ile Ile Asp Gly Ala Pro Cys
                                 1               5

( 2 ) INFORMATION FOR SEQ ID NO: 9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 9:

CGTGGATCCA TCGAAGGTCG T TTG GAA ACT GCA GGA GAA GAA    42
                                 Leu Glu Thr Ala Gly Glu Glu ( 2 ) INFORMATION FOR SEQ ID NO: 10:

( i ) SEQUENCE CHARACTERISTICS:
        ( A ) LENGTH: 18 base pairs

```
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 10:

AATTGTGGAA GCTTCCAC                                                                                           18

( 2 ) INFORMATION FOR SEQ ID NO: 11:

( i ) SEQUENCE CHARACTERISTICS:
        ( A ) LENGTH: 4 amino acids
        ( B ) TYPE: amino acids
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: /label=Xaa
                / note= "Succinylalanine"

( i x ) FEATURE:
        ( A ) NAME/KEY: Modified-site
        ( B ) LOCATION: 4
        ( C ) IDENTIFICATION METHOD: by experiment
        ( D ) OTHER INFORMATION: /label=Xaa
                / note= "phenylalanine-peptide nucleic acid"

( x i ) SEQUENCE DESCRIPTION: SEQ ID NO: 11:

Xaa   Ala   Pro   Xaa
1

( 2 ) INFORMATION FOR SEQ ID NO: 12:

( i ) SEQUENCE CHARACTERISTICS:
        ( A ) LENGTH: 225 amino acids
        ( B ) TYPE: amino acids
        ( C ) STRANDEDNESS: single
        ( D ) TOPOLOGY: linear ( i i ) MOLECULE TYPE: polypeptide ( x i ) SEQUENCE DESCRIPTION: SEQ ID NO: 12:

Ile   Ile   Asp   Gly   Ala   Pro   Cys   Ala   Arg   Gly   Ser   His   Pro   Trp   Gln   Val
1                       5                       10                          15

Ala   Leu   Leu   Ser   Gly   Asn   Gln   Leu   His   His   Cys   Gly   Gly   Val   Leu   Val
                  20                        25                          30

Asn   Glu   Arg   Trp   Val   Leu   Thr   Ala   Ala   His   Cys   Lys   Met   Asn   Glu   Tyr
            35                        40                        45

Thr   Val   His   Leu   Gly   Ser   Asp   Thr   Leu   Gly   Asp   Arg   Arg   Ala   Gln   Arg
      50                        55                        60

Ile   Lys   Ala   Ser   Lys   Ser   Phe   Arg   His   Pro   Gly   Tyr   Ser   Thr   Gln   Thr
65                        70                        75                              80

His   Val   Asn   Asp   Leu   Met   Leu   Val   Lys   Leu   Asn   Ser   Gln   Ala   Arg   Leu
                  85                        90                          95

Ser   Ser   Met   Val   Lys   Lys   Val   Arg   Leu   Pro   Ser   Arg   Cys   Glu   Pro   Pro
                  100                       105                         110

Gly   Thr   Thr   Cys   Thr   Val   Ser   Gly   Trp   Gly   Thr   Thr   Thr   Ser   Pro   Asp
            115                       120                       125

Val   Thr   Phe   Pro   Ser   Asp   Leu   Met   Cys   Val   Asp   Val   Lys   Leu   Ile   Ser
      130                       135                       140
```

|     |     |     |     |     |     |     |     |     |     |     |     |     |     |     |     |
|-----|-----|-----|-----|-----|-----|-----|-----|-----|-----|-----|-----|-----|-----|-----|-----|
| Pro 145 | Gln | Asp | Cys | Thr | Glu 150 | Val | Tyr | Lys | Asp | Leu 155 | Leu | Glu | Asn | Ser | Met 160 |
| Leu | Cys | Ala | Gly | Ile 165 | Pro | Asp | Ser | Lys | Lys 170 | Asn | Ala | Cys | Asn | Gly 175 | Asp |
| Ser | Gly | Gly | Pro 180 | Leu | Val | Cys | Arg | Gly 185 | Thr | Leu | Gln | Gly | Leu 190 | Val | Ser |
| Trp | Gly | Thr 195 | Phe | Pro | Cys | Gly | Gln 200 | Pro | Asn | Asp | Pro | Gly 205 | Val | Tyr | Thr |
| Gln | Val 210 | Cys | Lys | Phe | Thr | Lys 215 | Trp | Ile | Asn | Asp | Thr 220 | Met | Lys | Lys | His |
| Arg 225 |

(2) INFORMATION FOR SEQ ID NO: 13:

(i) SEQUENCE CHARACTERISTICS:
        (A) LENGTH: 229 amino acids
        (B) TYPE: amino acids
        (C) STRANDEDNESS: single
        (D) TOPOLOGY: linear (ii) MOLECULE TYPE: polypeptide (xi) SEQUENCE DESCRIPTION: SEQ ID NO: 13:

|     |     |     |     |     |     |     |     |     |     |     |     |     |     |     |     |
|-----|-----|-----|-----|-----|-----|-----|-----|-----|-----|-----|-----|-----|-----|-----|-----|
| Ile 1 | Val | Asn | Gly | Glu 5 | Asp | Ala | Val | Pro | Gly 10 | Ser | Trp | Pro | Trp | Gln 15 | Val |
| Ser | Leu | Gln | Asp 20 | Lys | Thr | Gly | Phe | His 25 | Phe | Cys | Gly | Gly | Ser 30 | Leu | Ile |
| Ser | Glu | Asp 35 | Trp | Val | Val | Thr | Ala 40 | Ala | His | Cys | Gly | Val 45 | Arg | Thr | Ser |
| Asp | Val 50 | Val | Val | Ala | Gly | Glu 55 | Phe | Asp | Gln | Gly | Ser 60 | Asp | Glu | Glu | Asn |
| Ile 65 | Gln | Val | Leu | Lys | Ile 70 | Ala | Lys | Val | Phe | Lys 75 | Asn | Pro | Lys | Phe | Ser 80 |
| Ile | Leu | Thr | Val | Asn 85 | Asn | Asp | Ile | Thr | Leu 90 | Leu | Lys | Leu | Ala | Thr 95 | Pro |
| Ala | Arg | Phe | Ser 100 | Gln | Thr | Val | Ser | Ala 105 | Val | Cys | Leu | Pro | Ser 110 | Ala | Asp |
| Asp | Asp | Phe 115 | Pro | Ala | Gly | Thr | Leu 120 | Cys | Ala | Thr | Thr | Gly 125 | Trp | Gly | Lys |
| Thr | Lys 130 | Tyr | Asn | Ala | Asn | Lys 135 | Thr | Pro | Asp | Lys | Leu 140 | Gln | Gln | Ala | Ala |
| Leu 145 | Pro | Leu | Leu | Ser | Asn 150 | Ala | Glu | Cys | Lys | Lys 155 | Ser | Trp | Gly | Arg | Arg 160 |
| Ile | Thr | Asp | Val | Met 165 | Ile | Cys | Ala | Gly | Ala 170 | Gly | Val | Ser | Ser | Cys 175 | Met |
| Gly | Asp | Ser | Gly 180 | Gly | Pro | Leu | Val | Cys 185 | Gln | Lys | Asp | Gly | Ala 190 | Trp | Thr |
| Leu | Val | Gly 195 | Ile | Val | Ser | Trp | Gly 200 | Ser | Asp | Thr | Cys | Ser 205 | Thr | Ser | Ser |
| Pro | Gly 210 | Val | Tyr | Ala | Arg | Val 215 | Thr | Lys | Leu | Ile | Pro 220 | Trp | Val | Gln | Lys |
| Ile 225 | Leu | Ala | Ala | Asn |

(2) INFORMATION FOR SEQ ID NO: 14:

(i) SEQUENCE CHARACTERISTICS:

(A) LENGTH: 235 amino acids
(B) TYPE: amino acids
(C) STRANDEDNESS: single
(D) TOPOLOGY: linear (ii) MOLECULE TYPE: polypeptide (xi) SEQUENCE DESCRIPTION: SEQ ID NO: 14:

| Ile | Ile | Gly | Gly | Arg | Glu | Ser | Arg | Pro | His | Ser | Arg | Pro | Tyr | Met | Ala |
|---|---|---|---|---|---|---|---|---|---|---|---|---|---|---|---|
| 1 | | | | 5 | | | | | 10 | | | | | 15 | |
| Tyr | Leu | Gln | Ile | Gln | Ser | Pro | Ala | Gly | Gln | Ser | Arg | Cys | Gly | Gly | Phe |
| | | | 20 | | | | | 25 | | | | | 30 | | |
| Leu | Val | Arg | Glu | Asp | Phe | Val | Leu | Thr | Ala | Ala | His | Cys | Trp | Gly | Ser |
| | | 35 | | | | | 40 | | | | | 45 | | | |
| Asn | Ile | Asn | Val | Thr | Leu | Gly | Ala | His | Asn | Ile | Gln | Arg | Arg | Glu | Asn |
| | 50 | | | | | 55 | | | | | 60 | | | | |
| Thr | Gln | Gln | His | Ile | Thr | Ala | Arg | Arg | Ala | Ile | Arg | His | Pro | Gln | Tyr |
| 65 | | | | | 70 | | | | | 75 | | | | | 80 |
| Asn | Gln | Arg | Thr | Ile | Gln | Asn | Asp | Ile | Met | Leu | Leu | Gln | Leu | Ser | Arg |
| | | | | 85 | | | | | 90 | | | | | 95 | |
| Arg | Val | Arg | Arg | Asn | Arg | Asn | Val | Asn | Pro | Val | Ala | Leu | Pro | Arg | Ala |
| | | | 100 | | | | | 105 | | | | | 110 | | |
| Gln | Glu | Gly | Leu | Arg | Pro | Gly | Thr | Leu | Cys | Thr | Val | Ala | Gly | Trp | Gly |
| | | 115 | | | | | 120 | | | | | 125 | | | |
| Arg | Val | Ser | Met | Arg | Arg | Gly | Thr | Asp | Thr | Leu | Arg | Glu | Val | Gln | Leu |
| | 130 | | | | | 135 | | | | | 140 | | | | |
| Arg | Val | Gln | Arg | Asp | Arg | Gln | Cys | Leu | Arg | Ile | Phe | Gly | Ser | Tyr | Asp |
| 145 | | | | | 150 | | | | | 155 | | | | | 160 |
| Pro | Arg | Arg | Gln | Ile | Cys | Val | Gly | Asp | Arg | Arg | Glu | Arg | Lys | Ala | Ala |
| | | | | 165 | | | | | 170 | | | | | 175 | |
| Phe | Lys | Gly | Asp | Ser | Gly | Gly | Pro | Leu | Leu | Cys | Asn | Asn | Val | Ala | His |
| | | | 180 | | | | | 185 | | | | | 190 | | |
| Gly | Ile | Val | Ser | Tyr | Gly | Lys | Ser | Ser | Gly | Val | Pro | Pro | Glu | Val | Phe |
| | | 195 | | | | | 200 | | | | | 205 | | | |
| Thr | Arg | Val | Ser | Ser | Phe | Leu | Pro | Trp | Ile | Arg | Thr | Thr | Met | Arg | Ser |
| | 210 | | | | | 215 | | | | | 220 | | | | |
| Phe | Lys | Leu | Leu | Asp | Gln | Met | Glu | Thr | Pro | Leu | | | | | |
| 225 | | | | | 230 | | | | | 235 | | | | | |

(2) INFORMATION FOR SEQ ID NO: 15:

(i) SEQUENCE CHARACTERISTICS:
(A) LENGTH: 226 amino acids
(B) TYPE: amino acids
(C) STRANDEDNESS: single
(D) TOPOLOGY: linear (ii) MOLECULE TYPE: polypeptide (xi) SEQUENCE DESCRIPTION: SEQ ID NO: 15:

| Ile | Ile | Gly | Gly | Thr | Glu | Cys | Lys | Pro | His | Ser | Arg | Pro | Tyr | Met | Ala |
|---|---|---|---|---|---|---|---|---|---|---|---|---|---|---|---|
| 1 | | | | 5 | | | | | 10 | | | | | 15 | |
| Tyr | Leu | Glu | Ile | Val | Thr | Ser | Asn | Gly | Pro | Ser | Lys | Phe | Cys | Gly | Gly |
| | | | 20 | | | | | 25 | | | | | 30 | | |
| Phe | Leu | Ile | Arg | Arg | Asn | Phe | Val | Leu | Thr | Ala | Ala | His | Cys | Ala | Gly |
| | | | 35 | | | | | 40 | | | | | 45 | | |
| Arg | Ser | Ile | Thr | Val | Thr | Leu | Gly | Ala | His | Asn | Ile | Thr | Glu | Glu | Glu |
| | 50 | | | | | 55 | | | | | 60 | | | | |
| Asp | Thr | Trp | Gln | Lys | Leu | Glu | Val | Ile | Lys | Gln | Phe | Arg | His | Pro | Lys |

| | | | | 65 | | | | | 70 | | | | | 75 | | | | | 80 |
|---|---|---|---|---|---|---|---|---|---|---|---|---|---|---|---|---|---|---|---|
| Tyr | Asn | Thr | Ser | Thr 85 | Leu | His | His | Asp | Ile 90 | Met | Leu | Leu | Lys | Leu 95 | Lys |
| Glu | Lys | Ala | Ser 100 | Leu | Thr | Leu | Ala | Val 105 | Gly | Thr | Leu | Pro | Phe 110 | Pro | Ser |
| Gln | Phe | Asn 115 | Phe | Val | Pro | Pro | Gly 120 | Arg | Met | Cys | Arg | Val 125 | Ala | Gly | Trp |
| Gly | Arg 130 | Thr | Gly | Val | Leu | Lys 135 | Pro | Gly | Ser | Asp | Thr 140 | Leu | Gln | Glu | Val |
| Lys 145 | Leu | Arg | Leu | Met | Asp 150 | Pro | Gln | Ala | Cys | Ser 155 | His | Phe | Arg | Asp | Phe 160 |
| Asp | His | Asn | Leu | Gln 165 | Leu | Cys | Val | Gly | Asn 170 | Pro | Arg | Lys | Thr | Lys 175 | Ser |
| Ala | Phe | Lys | Gly 180 | Asp | Ser | Gly | Gly | Pro 185 | Leu | Leu | Cys | Ala | Gly 190 | Val | Ala |
| Gln | Gly | Ile 195 | Val | Ser | Tyr | Gly | Arg 200 | Ser | Asp | Ala | Lys | Pro 205 | Pro | Ala | Val |
| Phe | Thr 210 | Arg | Ile | Ser | His | Tyr 215 | Arg | Pro | Trp | Ile | Asn 220 | Gln | Ile | Leu | Gln |
| Ala 225 | Asn |

( 2 ) INFORMATION FOR SEQ ID NO: 16:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: Yes ( x i ) SEQUENCE DESCRIPTION: SEQ ID NO: 16:

TGATCCTCTG AGCTCTCCTG 20

( 2 ) INFORMATION FOR SEQ ID NO: 17:

( i ) SEQUENCE CHARACTERISTICS:
        ( A ) LENGTH: 11 amino acids
        ( B ) TYPE: amino acids
        ( C ) STRANDEDNESS: single
        ( D ) TOPOLOGY: linear ( i i ) MOLECULE TYPE: peptide ( x i ) SEQUENCE DESCRIPTION: SEQ ID NO: 17:

| Ala 1 | Gln | Gly | Asp | Lys 5 | Ile | Ile | Asp | Gly | Ala 10 | Pro |